(12) United States Patent
Sligar et al.

(10) Patent No.: US 7,083,958 B2
(45) Date of Patent: Aug. 1, 2006

(54) MEMBRANE SCAFFOLD PROTEINS

(75) Inventors: Stephen G. Sligar, Urbana, IL (US);
Timothy H. Bayburt, Urbana, IL (US);
Mary A. Schuler, Urbana, IL (US);
Natanya R Civjan, Urbana, IL (US);
Yelena V. Grinkova, Urbana, IL (US);
Ilia G. Denisov, Urbana, IL (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 86 days.

(21) Appl. No.: 10/465,789

(22) Filed: Jun. 18, 2003

(65) Prior Publication Data

US 2004/0053384 A1   Mar. 18, 2004

Related U.S. Application Data

(63) Continuation-in-part of application No. 09/990,087, filed on Nov. 20, 2001.

(60) Provisional application No. 60/252,233, filed on Nov. 20, 2000.

(51) Int. Cl.
*C12N 9/00* (2006.01)
*C07K 14/435* (2006.01)

(52) U.S. Cl. ..................................... 435/183; 530/350
(58) Field of Classification Search ................ 435/188; 424/400, 94.3; 530/350
See application file for complete search history.

(56) References Cited

U.S. PATENT DOCUMENTS 6,172,262 B1   1/2001   McQuade et al. ........... 564/182
6,248,353 B1   6/2001   Singh ......................... 424/450

FOREIGN PATENT DOCUMENTS

WO   WO 93/17031       9/1993
WO   WO 00/75187      12/2000
WO   WO 01/02551 A2    1/2001

OTHER PUBLICATIONS

Barnes et al., A review of central 5-HT receptors and their function. 38:1083-1152, 1999.*
Dubois et al. (Jun. 2001) "Self-Assembly or Regular Hollow Icosahedra in Salt-Free Catanionic Solutions," *Nature* 411:672-675.
U.S. Appl. No. 09/990,087, filed Nov. 20, 2001, Sligar et al.
Atkinson, D. and Small, D.M. (1986) "Recombinant Lipoproteins:Implications for Structure and Assembly of Native Lipoproteins" *Ann. Rev. Biophys. Chem.* 15:403-456.
Bayburt, T.H. et al. (1998) "Reconstitution and Imaging of a Membrane Protein in a Nanometer-Size Phospholipid bilayer" *J. Struct. Biol.* 123:37-44.
Bayburt, T.H. et al. (Jun. 2000) "Single Molecule Height Measurements on a Membrane Protein in Nanometer-Scale Phospholipid Bilayer Disks" *Langmuir* 16(14):5993-5997.
Boguski, M.S. et al. (1986) "On computer-assisted analysis of biological sequences: proline punctuation, consensus sequences, and apolipoprotein repeats" *J. of Lipid Research* 27:1011-1034.
Borhani, D.W. et al. (1997) "Crystal structure of truncated human apolipoprotein A-I suggests a lipid-bound conformation" *Proc. Natl. Acad. Sci. USA* 94:12291-12296.
Brouillette, C.G. et al. (1984) "Structural Studies of Apolipoprotein A-I/Phosphatidylcholine Recombinants by High-Field Proton NMR, Nondenaturing Gradient Gel Electrophoresis, and Electron Microscopy" *Biochemistry* 23:359-367.
Carlson, J. W. et al. (Mar. 2000) "Nanopatterning Phospholipid Bilayers" *Langmuir* 16(8):3927-3931.
Carlson, J.W. et al. (Sep. 1997) "Imaging and Manipulation of High-Density Lipoproteins" *Biophys. J.* 73:1184-1189.
Dalton, M.B. and Swaney, J.B. (Sep. 15, 1993) "Structural and Functional Domains of Apolipoprotein A-I within High Density Lipoproteins" *J. Biol. Chem.* 268(26):19274-19283.
Durbin, D.M. and Jonas, A. (Dec. 1999) "Lipid-free apolipoproteins A-I and A-II promote remodeling of reconstituted high density lipoproteins and alter their reactivity with lecithin:cholesterol acyltransferase" *J. Lipid Research* 40(12):2293-2302.
Fidge, N.H. (Feb. 1999) "High density lipoprotein receptors, binding proteins, and ligands" *J. Lipid Research* 40(2):187-201.

(Continued)

*Primary Examiner*—Ruixiang Li
(74) *Attorney, Agent, or Firm*—Greenlee, Winner & Sullivan

(57) ABSTRACT

Membrane proteins are difficult to express in recombinant form, purify, and characterize, at least in part due to their hydrophobic or partially hydrophobic properties. The membrane scaffold proteins (MSP) of the present invention assemble with target membrane or other hydrophobic or partially hydrophobic proteins or membrane fragments to form soluble nanoscale particles which preserve their native structure and function; they are improved over liposomes and detergent micelles. In the presence of phospholipid, MSPs form nanoscopic phospholipid bilayer disks, with the MSP stabilizing the particle at the perimeter of the bilayer domain. The particle bilayer structure allows manipulation of incorporated proteins in solution or on solid supports, including for use with such surface-sensitive techniques as scanning probe microscopy or surface plasmon resonance. The nanoscale particles, which are robust in terms of integrity and maintenance of biological activity of incorporated proteins, facilitate pharmaceutical and biological research, structure/function correlation, structure determination, bio-separation, and drug discovery.

17 Claims, 12 Drawing Sheets

OTHER PUBLICATIONS

Fielding, P.E. and Fielding, C.J. (1991) "Dynamics of lipoprotein transport in the circulatory system" *Biochemistry of Lipids, Lipoproteins, and Membranes.* D.E. Vance and J. Vance. Amsterdam, Elsevier Press Chapter 15, pp. 427-459.

Forte, T.M. et al. (1971) "Electron microscopic study on reassembly of plasma high density apoprotein with various lipids" *Biochim. Biophys. Acta* 248:381-386.

Frank, P.G. et al. (1997) "Deletion of Central α-Helices in Human Apolipoprotein A-I: Effect on Phospholipid Association" *Biochemistry* 36:1798-1806.

Friis, E.P. et al. (Feb. 1999) "An approach to long-range electron transfer mechanisms in mettalloproteins: *in situ* scanning tunneling ,microscopy with submolecular resolution" *Proc. Natl. Acad. Sci. USA* 96:1379-1384.

Glomset, J.A. (1968) "The plasma lecithin:cholesterol acyltransferase reaction" *J. Lipid Research* 9:155-167.

Holvoet, P. et al. (1995) "Phospholipid Binding and Lecithin-Cholesterol Acyltransferase Activation Properties of Apolipoprotein A-I Mutants" (1995) *Biochemistry* 34:13334-13342.

Jin, L et al. (1995) "Surface Plasmon Resonance Biosensor Studies of Human Wild-Type and Mutant Lecithin Cholesterol Acyltransferase Interactions with Lipoproteins" *Biochemistry* 38(47):15659-15665.

Jonas, A. (1986) "Reconstitution of High Density Lipoproteins" *Methods Enzymol.* 128:553-582.

Jonas, A. (1991) "Lecithin-cholesterol acyltransferase in the metabolism of high-density lipoproteins" *Biochim,. Biophys. Acta* 1084:205-220.

Jonas, A. et al. (1989) "Defined Apolipoprotein A-I Conformation in Reconstituted High Density Lipoprotein Discs" *J. Biol. Chem.* 264(9):4818-4824.

Koppaka, V. et al. (May 1999) "The Structure of Human Lipoprotein A-I" *J. Biol. Chem.* 274(21):14541-14544.

Miller, J.P. et al. (1996) "X-ray Diffraction Analysis of Cytochrome P450 2B4 Reconstituted into Liposomes" *Biochemistry* 35:1466-1474.

Mukhopadhyay, R. et al. (Mar. 31, 2000) "A scanning tunneling microscopy study of *Clostridium pasteurianum* rubredoxin" *J. Inorg. Biochem.* 78:251-254.

Phillips, J.C. et al. (1997) "Predicting the Structure of Apolipoprotein A-I in Reconstituted High-Density Lipoprotein Disks" *Biophysics Journal* 73:2337-2346.

Robinson, C.R. and Sligar, S.G. (1998) "Changes in solvation during DNA binding and cleavage are critical to altered specificity of the *Eco*RI endonuclease" *Proc. Natl. Acad. Sci. USA* 95:2186-2191.

Robinson, C.R. and Sauer, R.T. (May 1998) "Optimizing the stability of single-chain proteins by linker length and composition mutagenesis" *Proc. Natl. Acad. Sci. USA* 95(11):5929-5934.

Rogers, D.P. et al. (1998) "Structural Analysis of Apolipoprotein A-I: Effects of Amino-and Carboxy-Terminal Deletions on the Lipid-Free Structure" Biochemistry 37:945-955.

Rogers, D.P. et al. (1998) "The Lipid-Free Structure of Apolipoprotein A-I: Effects of Amino-Terminal Deletions" Biochemistry 37(34):11714-11725.

Salamon, Z. (1997) "Coupled Plasmon—Waveguide Resonators: A New Spectroscopic Tool for Probing Proteolipid Film Structure and Properties" *Biophys. Journal* 73:2791-2797.

Schafmeister, C. et al. (1993) "Structure at 2.5 Å of a Designed Peptide That Maintains Solubility of Membrane Proteins" *Science* 262:734-738.

Segrest, J.P. et al. (Nov. 1999) "A Detailed Molecular Belt Model for Apolipoprotein A-I in Discoidal High Density Lipoprotein" *J. Biol. Chem.* 274(45):31755-31758.

Sklar, L.A. et al. (May 2000) "Solubilization and Display of G Protein-Coupled Receptors on Beads for Real-Time Fluorescence and Flow Cytometric Analysis" *BioTechniques* 28(5):976-985.

Tocanne, J.F. et al. (1994) "Lipid domains and lipid/protein interactions in biological membranes" *Chemistry and Physics of Lipids* 73:139-158.

Wald, J.H. et al. (1990) "Investigation of the Lipid Domains and Apolipoprotein Orientation in Reconstituted High Density Lipoproteins by Fluorescence and IR Methods" *J. Biol. Chem.* 265(32):20044-20050.

Wald, J. H. et al. (1990) "Structure of Apolipoprotein A-I in Three Homogeneous, Reconstituted High Density Lipoprotein Particles" *J. Biol. Chem.* 265(32):20037-20043.

Wang, M. et al. (1997) "Three -dimensional structure of NADPH-cytochrome P450 reductase: Prototype for FMN and FAD-containing enzymes" *Proc. Natl. Acad. Sci. USA* 94:8411-8416.

Wlodawer, A. et al. (1979) "High-Density Lipoprotein Recombinants: Evidence For A Bicycle Tire Micelle Structure Obtained By Neutron Scattering and Electron Microscopy" *FEBS Lett.* 104(2):231-235 Segr35.

Zuck, P. et al. (Sep. 1999) "Ligand-receptor binding measured by laser-scanning imaging" *Proc. Natl. Acad. Sci. USA* 96:11122-11127.

Bakker, E.P. and Caplan, S.R. (1982), "Phospholipid Substitution of the Purple Membrane," Methods in Enzymol. 88:26-30.

Bayburt, T.H. et al., (Dec. 2002) "Self-Assembly of Discoidal Phospholipid Bilayer Nanoparticles with Membrane Scaffold Proteins"; Nano Letters 2:853-856.

Bayburt, T.H. et. al., (May 2002) "Single Molecule Height Measurements on Microsomal Cytochrome P450 in nanometer-Scale Phospholipid Bilayer Disks"; *Proceedings of the National Academy of Sciences* 99:6725-6730.

Bayburt, T.H. et al. (Nov. 2003) "Self-Assembly of Single Integral Membrane Proteins into Soluble Nanoscale Phospholipid Bilayers"; Protein Science 12:2476-2481.

Bayley, H. et al. (1982), "Delipidation, Renaturation, and Reconstitution of Bacberiorhodopsin," Methods Enzymol. 88:74-81.

Brouillette, C. et al., (2001), "Structural modelsof human apolipoprotein A-I: a critical analysis and review," Biochim. Biophys. Acta 1531:4-46.

Carlson, J.W. et al., (1997) "Imaging and Manipulation of High-Density Lipoproteins"; *Biophysical J.* 73:1184-1189.

Carlson, J.W. et al. (Dec. 2000) "Nanopatterning Phospholipid Bilayers"; *Langmuir* 16:3927-3931.

Chen, J.S. et al., (2002) *Insect Molecular Biology* 11:175-186.

Civjan, N.R. et al., (2003) "Direct Solubilization of Heterologously Expressed Membrane Proteins by Incorporation into Nanoscale Lipid Bilayers"; *BioTechniques* 35:556-563.

Dencher, N.A. and Heyn, M.P. (1982) *Methods Enzymol.* 88:5-10.

Denisov, I.G.; et al. (Mar. 2004) "Directed Self Assembly of Monodisperse Phospholipid Bilayer Nanodiscs with Controlled Size"; *J. Am. Chem. Soc.,* In Press.

Duan, et al. (2004) Co-incorporation of Heterologously-Expressed *Arabidopsis* Cytochrome P450 and P450 Reductase into Soluble Nanoscale Lipid Bilayers'; *Archives Biochemistry and Biophysics,* In Press.

Heyn, M.P. et al. (1982) "Reconstitution of Monomeric Bacteriorhodopsin into Phospholipid Vesicles;" Methods Enzymol. 88:31-35.

Imaoka, S. et al., (1992), "Role of Phospholipids in Reconstituted Cytochrome P450 3A Form and Mechanism of Their Activation of Catalytic Activity," *Biochemistry* 31:6063-6069.

Korenbrot, J.I. (YEAR), "The Assembly of Bacteriorhodopsin-Containing Planar Membranes by the Sequential Transfer of Air-Water Interface Films," Methods Enzymol. 88:45-55.

Marheineke, K. et al., (1998), "Lipid composition of *Spodoptera frugiperda* (Sf9) and *Trichoplusia ni* (Tn) insect cells used for baculovirus infection," *FEBS Letters* 441:49-52.

McGregor, C-L. (Feb. 2003), "Lipopeptide detergents designed for the structural study of membrane proteins,"Nature Biotechnol. 21:171-176.

Rezaie et al. (1992), "Expression and Purification of a Soluble Tissue Factor Fusion Protein with an Epitope for an Unusual Calcium-Dependent Antibody," *Protein Expression and Purification* 3:453-460.

Savelli, G. et al. (2000), "Enzyme activity and stability control by amphiphilic self-organizing systems in aqueous solutions," *Curr. Opin. Colloid & Interface Science* 5:111-117.

Shaw, A.W. et al., (Jan. 2004) "Phospholipid Phase Transitions in Homogeneous Nanometer Scale Bilayer Discs"; *FEBS Letters* 556:260-264.

Skulachev, V.P. (1982), "A Single Turnover Study of Photoelectric Current-Generating Proteins," Methods Enzymol. 88:35-45.

Sligar, S. (2003) "Finding a Single-Molecule Solution for Membrane Proteins"; *Biochem. Biophys. Res. Comm.* 312:115-119.

Bruhn et al. (1991) "An Approach to the Functional Analysis of Lecithin-Cholesterol Acryltransferase. Activation by Recombinant Normal and Mutagenized Apolipoprotein AI," *Biological Chemistry Hoppee-Seyler* 372(3):225-234.

Burgess et al. (Nov. 2, 1999) "Deletion of the C-Terminal Domain of Apolipoprotein A-I Impairs Cell Surface Binding and Lipid Efflux in Macrophage," *Biochem.* 38(44):14524-14533.

Frank et al. (1998) "Importance of Central α-Helixes of Human Apolipoprotein A-I in the Maturation of High Density Lipoproteins," *Biochem.* 37(39):13902-13909.

Gillotte et al. (1996) "Apolipoprotein A-I Structural Modification and the Functionality of Reconstituted High Density Lipoprotein Particles in Cellular Cholesterol Efflux," *J. Biol. Chem.* 271(39):23792-23798.

Gillotte et al. (Jan. 1999) "Apolipoprotein-Mediated Plasma Membrane Microsolubilization. Role of Lipid Affinity and Membrane Penetration in the Efflux of Cellular Cholesterol and Phospholipid," *J. Biol. Chem.* 274(4):2021-2028.

Laccotripe et al. (1997) "The Carboxyl-Terminal Hydrophobic Residues of Apolipoprotein A-I Affect its Rate of Phospholipid Binding and its Association with High Density Lipoprotein," *J. Biol. Chem.* 272(28):17511-17522.

Liadaki et al. (Jul. 2000) "Binding of High Density Lipoprotein (HDL) and Discoidal Reconstituted HDL to the HDL Receptor Scavenger Receptor Class B Type I. Effect of Lipid Association and apoA-I Mutations on Receptor Binding," *J. Biol. Chem.* 275(28):21262-21271.

Marcel et al. (1998) "Definition of Apolipoprotein A-I Domains Involved in Reverse Cholesterol Transport," *International Congress Series* 1155:(Atherosclerosis XI)1149-1153.

McManus et al. (Feb. 2000) "Distinct Central Amphipathic α-Helices in Apolipoprotein A-I Contribute to the in Vivo Maturation of High Density Lipoprotein by Either Activating Lechithin-Cholesterol Acyltransferase or Binding Lipids," *J. Biol. Chem.* 275(7):5043-5051.

Minnich et al. (1992) "Site-Directed Mutagenesis and Structure-Function Analysis of the Human Apolipoprotein A-I. Relation Between Lecithin-Cholesterol Acyltransferase Activation and Lipid Binding," *J. Biol. Chem.* 267(23):16553-16560.

Reardon et al. (Oct. 2001) "In Vivo Studies of HDL Assembly and Metabolism Using Adenovirus-Mediated Transfer of ApoA-I Mutants in ApoA-I-Deficient Mice," *Biochem.* 40(45):13670-13680.

Rogers et al. (1997) "Truncation of the Amino Terminus of Human Apolipoprotein A-I Substantially Alters Only the Lipid-Free Conformation," *Biochem.* 36(2):288-300.

Rosseneu et al. (1992) "Contribution of Helix—Helix Interactions to the Stability of Apolipoprotein-Lipid Complexes," *International Congress Series* 1001:(High Density Lipoproteins Atheroscler. III)105-114.

Sorci-Thomas et al. (1998) "The Hydrophobic Face Orientation of Apolipoprotein A-I Amphipathic Helix Domain 143-164 Regulates Lecthin: Cholesterol Acyltransferase Activation," *J. Biol. Chem.* 273(19):11776-11782.

Sorci-Thomas et al. (1997) "Alteration in Apolipoprotein A-I 22-Mer Repeat Order Results in a Decrease in Lecithin: Cholesterol Acyltransferase Reactivity," *J. Biol. Chem.* 272(11):7278-7284.

Scott et al. (Dec. 2001) "The N-Terminal Globular Domain and the First Class A Amphipathic Helix of Apolipoprotein A-I are Important for Lecithin: Cholesterol Acyltransferase Activation and the Maturation of High Density Lipoprotein in Vivo," *J. Biol. Chem.* 276(52):48716-48724.

Sviridov et al. (Jun. 2000) "Identification of a Sequence of Apolipoprotein A-I Associated With the Activation of Lecithin: Cholesterol Acyltransferase," *J. Biol. Chem.* 275(26):19707-19712.

Sviridov et al. (1996) "Efflux of Cellular Cholesterol and Phospholipid to Apolipoprotein A-I Mutants," *J. Biol. Chem.* 271(52):33277-33283.

* cited by examiner

Liposomes  Detergent Micelles  Disks

- hydrophobic amino acids
○ more polar amino acids
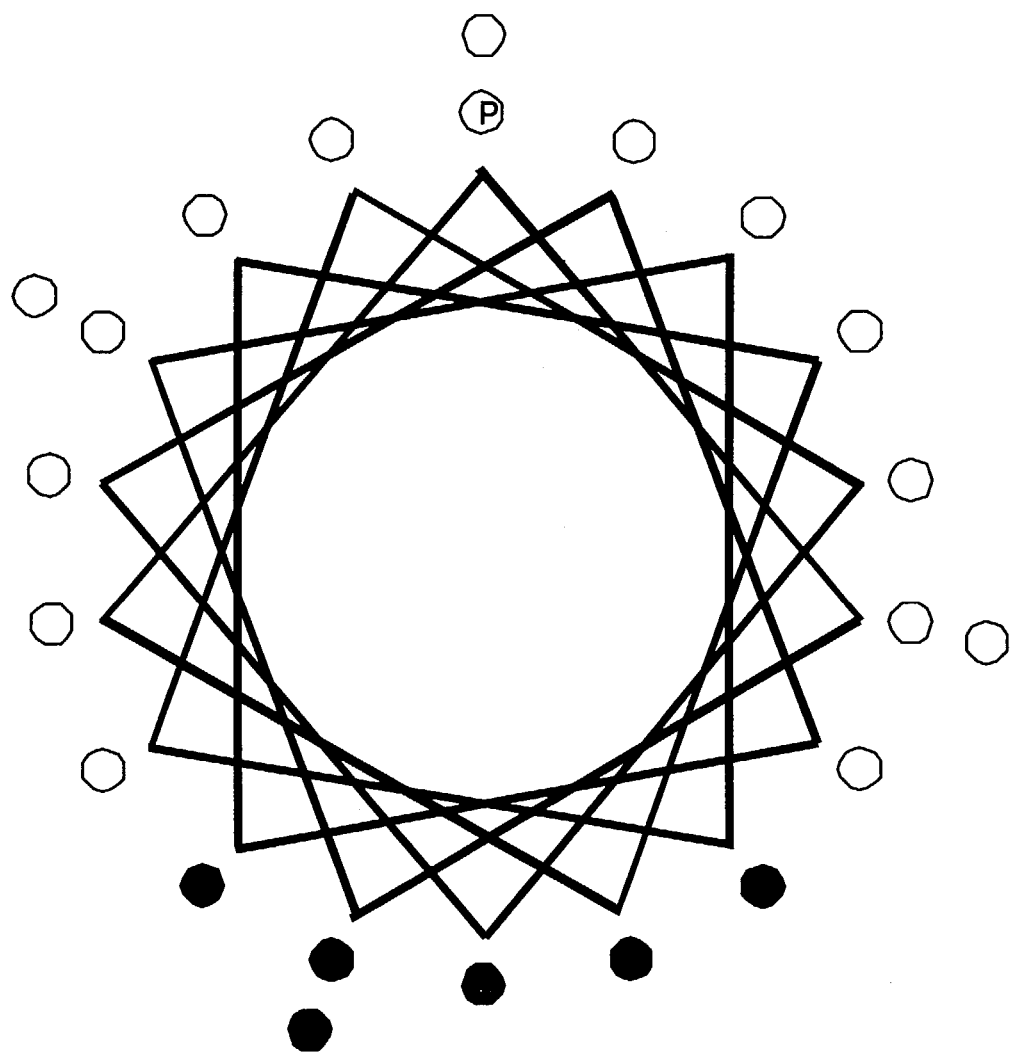
FIG. 2

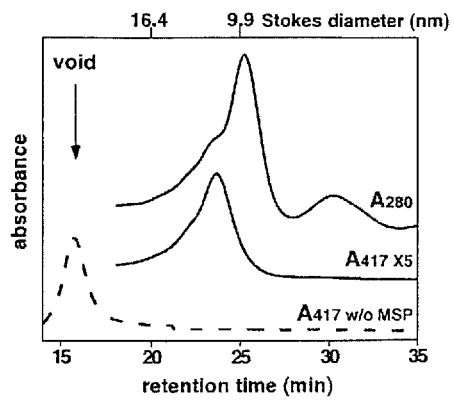
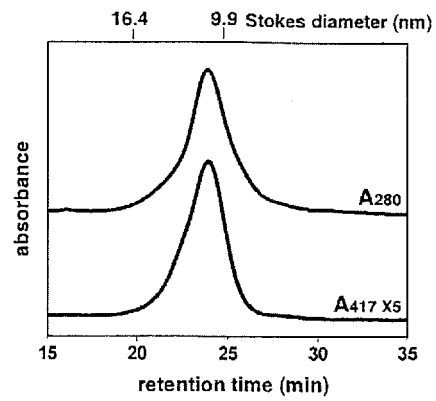
FIG. 16A  FIG. 16B
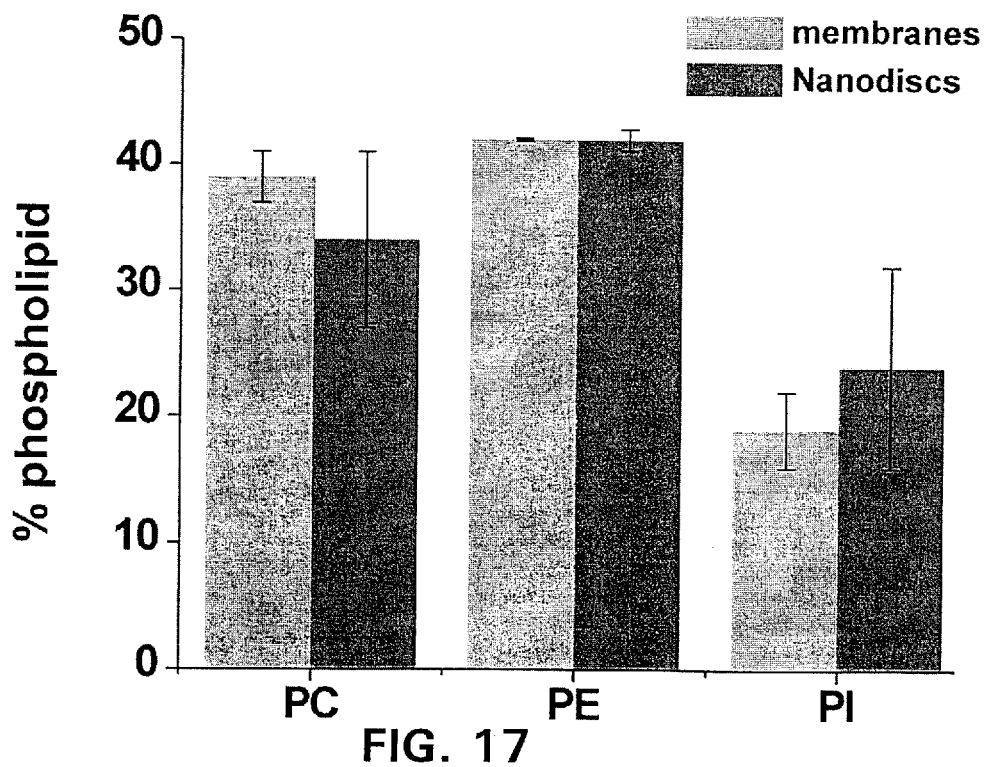
FIG. 17

SEQUENCE LISTING

<160> NUMBER OF SEQ ID NOS: 89

<210> SEQ ID NO 1
<211> LENGTH: 762
<212> TYPE: DNA
<213> ORGANISM: Homo sapiens

<400> SEQUENCE: 1

```
ccatggccca tttctggcag caagatgaac cccccagag ccctgggat cgagtgaagg      60 acctggccac tgtgtacgtg gatgtgctca aagacagcgg cagagactat gtgtcccagt    120
ttgaaggctc cgccttggga aaacagctaa acctaaagct ccttgacaac tgggacagcg    180
tgacctccac cttcagcaag ctgcgcgaac agctcggccc tgtgacccag gagttctggg    240
ataacctgga aaaggagaca gagggcctga ggcaagagat gagcaaggat ctggaggagg    300
tgaaggccaa ggtgcagccc tacctggacg acttccagaa gaagtggcag gaggagatgg    360
agctctaccg ccagaaggtg gagccgctgc gcgcagagct ccaagagggc gcgcgccaga    420
agctgcacga gctgcaagag aagctgagcc cactgggcga ggagatgcgc gaccgcgcgc    480
gcgcccatgt ggacgcgctg cgcacgcatc tggcccccta cagcgacgag ctgcgccagc    540
gcttggccgc gcgccttgag gctctcaagg agaacggcgg cgccagactg gccgagtacc    600
acgccaaggc caccgagcat ctgagcacgc tcagcgagaa ggccaagccc gcgctcgagg    660
acctccgcca aggcctgctg cccgtgctgg agagcttcaa ggtcagcttc ctgagcgctc    720
tcgaggagta cactaagaag ctcaacaccc agtaataagc tt                       762
```

<210> SEQ ID NO 2
<211> LENGTH: 250
<212> TYPE: PRT
<213> ORGANISM: Homo sapiens

<400> SEQUENCE: 2

```
Met Ala His Phe Trp Gln Gln Asp Glu Pro Pro Gln Ser Pro Trp Asp
1               5                   10                  15

Arg Val Lys Asp Leu Ala Thr Val Tyr Val Asp Val Leu Lys Asp Ser
                20                  25                  30

Gly Arg Asp Tyr Val Ser Gln Phe Glu Gly Ser Ala Leu Gly Lys Gln
            35                  40                  45

Leu Asn Leu Lys Leu Leu Asp Asn Trp Asp Ser Val Thr Ser Thr Phe
        50                  55                  60

Ser Lys Leu Arg Glu Gln Leu Gly Pro Val Thr Gln Glu Phe Trp Asp
65                  70                  75                  80

Asn Leu Glu Lys Glu Thr Glu Gly Leu Arg Gln Glu Met Ser Lys Asp
                85                  90                  95

Leu Glu Glu Val Lys Ala Lys Val Gln Pro Tyr Leu Asp Asp Phe Gln
                100                 105                 110

Lys Lys Trp Gln Glu Glu Met Glu Leu Tyr Arg Gln Lys Val Glu Pro
            115                 120                 125
```

```
Leu Arg Ala Glu Leu Gln Glu Gly Ala Arg Gln Lys Leu His Glu Leu
    130                 135                 140

Gln Glu Lys Leu Ser Pro Leu Gly Glu Glu Met Arg Asp Arg Ala Arg
145                 150                 155                 160

Ala His Val Asp Ala Leu Arg Thr His Leu Ala Pro Tyr Ser Asp Glu
                165                 170                 175

Leu Arg Gln Arg Leu Ala Ala Arg Leu Glu Ala Leu Lys Glu Asn Gly
            180                 185                 190

Gly Ala Arg Leu Ala Glu Tyr His Ala Lys Ala Thr Glu His Leu Ser
        195                 200                 205

Thr Leu Ser Glu Lys Ala Lys Pro Ala Leu Glu Asp Leu Arg Gln Gly
    210                 215                 220

Leu Leu Pro Val Leu Glu Ser Phe Lys Val Ser Phe Leu Ser Ala Leu
225                 230                 235                 240

Glu Glu Tyr Thr Lys Lys Leu Asn Thr Gln
                245                 250

<210> SEQ ID NO 3
<211> LENGTH: 61
<212> TYPE: DNA
<213> ORGANISM: Artificial Sequence
<220> FEATURE:
<223> OTHER INFORMATION: oligonucleotide primer

<400> SEQUENCE: 3
tataccatgg gccatcatca tcatcatcat atagaaggaa gactaaagct ccttgacaac    60
t                                                                   61

<210> SEQ ID NO 4
<211> LENGTH: 30
<212> TYPE: DNA
<213> ORGANISM: Artificial Sequence
<220> FEATURE:
<223> OTHER INFORMATION: oligonucleotide primer

<400> SEQUENCE: 4
gcaagcttat tactgggtgt tgagcttctt                                    30

<210> SEQ ID NO 5
<211> LENGTH: 654
<212> TYPE: DNA
<213> ORGANISM: Artificial Sequence
<220> FEATURE:
<223> OTHER INFORMATION: nucleotide sequence encoding HIS-tagged MSP1

<400> SEQUENCE: 5
tataccatgg gccatcatca tcatcatcat atagaaggaa gactaaagct ccttgacaac    60
tgggacagcg tgacctccac cttcagcaag ctgcgcgaac agctcggccc tgtgacccag   120
gagttctggg ataacctgga aaaggagaca gagggcctga ggcaggagat gagcaaggat   180
ctggaggagg tgaaggccaa ggtgcagccc tacctggacg acttccagaa gaagtggcag   240
gaggagatgg agctctaccg ccagaaggtg agccgctgc gcgcagagct ccaagagggc   300
gcgcgccaga gctgcacga gctgcaagag aagttgagcc cactgggcga ggagatgcgc   360
gaccgcgcgc gcgcccatgt ggacgcgctg cgcacgcatc tggccccta cagcgacgag   420 ctgcgccagc gcttggccgc gcgccttgag gctctcaagg agaacggcgg cgccagactg   480
gccgagtacc acgccaaggc caccgagcat ctgagcacgc tcagcgagaa ggccaaaccc   540
gcgctcgagg acctccgcca aggcctgctg cccgtgctgg agagcttcaa ggtcagcttc   600
```
ctgagcgctc tcgaggagta cactaagaag ctcaacaccc agtaataagc ttgc        654

<210> SEQ ID NO 6
<211> LENGTH: 212
<212> TYPE: PRT
<213> ORGANISM: Artificial Sequence
<220> FEATURE:
<223> OTHER INFORMATION: HIS-tagged MSP1

<400> SEQUENCE: 6

Met Gly His His His His His His Ile Glu Gly Arg Leu Lys Leu Leu
1               5                   10                  15

Asp Asn Trp Asp Ser Val Thr Ser Thr Phe Ser Lys Leu Arg Glu Gln
            20                  25                  30

Leu Gly Pro Val Thr Gln Glu Phe Trp Asp Asn Leu Glu Lys Glu Thr
        35                  40                  45

Glu Gly Leu Arg Gln Glu Met Ser Lys Asp Leu Glu Glu Val Lys Ala
    50                  55                  60

Lys Val Gln Pro Tyr Leu Asp Asp Phe Gln Lys Lys Trp Gln Glu Glu
65                  70                  75                  80

Met Glu Leu Tyr Arg Gln Lys Val Glu Pro Leu Arg Ala Glu Leu Gln
                85                  90                  95

Glu Gly Ala Arg Gln Lys Leu His Glu Leu Gln Glu Lys Leu Ser Pro
            100                 105                 110

Leu Gly Glu Glu Met Arg Asp Arg Ala Arg Ala His Val Asp Ala Leu
        115                 120                 125

Arg Thr His Leu Ala Pro Tyr Ser Asp Glu Leu Arg Gln Arg Leu Ala
    130                 135                 140

Ala Arg Leu Glu Ala Leu Lys Glu Asn Gly Gly Ala Arg Leu Ala Glu
145                 150                 155                 160

Tyr His Ala Lys Ala Thr Glu His Leu Ser Thr Leu Ser Glu Lys Ala
                165                 170                 175

Lys Pro Ala Leu Glu Asp Leu Arg Gln Gly Leu Leu Pro Val Leu Glu
            180                 185                 190

Ser Phe Lys Val Ser Phe Leu Ser Ala Leu Glu Glu Tyr Thr Lys Lys
        195                 200                 205

Leu Asn Thr Gln
    210

<210> SEQ ID NO 7
<211> LENGTH: 27
<212> TYPE: DNA
<213> ORGANISM: Artificial Sequence
<220> FEATURE:
<223> OTHER INFORMATION: oligonucleotide primer

<400> SEQUENCE: 7
taccatggca aagctccttg acaactg                                       27

<210> SEQ ID NO 8
<211> LENGTH: 619
<212> TYPE: DNA
<213> ORGANISM: Artificial Sequence
<220> FEATURE:
<223> OTHER INFORMATION: nucleotide sequence encoding MSP1 without
      His-tag

<400> SEQUENCE: 8
taccatggca aagctccttg acaactggga cagcgtgacc tccaccttca gcaagctgcg   60

-continued

| | | |
|---|---|---|
| cgaacagctc ggccctgtga cccaggagtt ctgggataac ctggaaaagg agacagaggg | 120 |
| cctgaggcag gagatgagca aggatctgga ggaggtgaag gccaaggtgc agccctacct | 180 |
| ggacgacttc cagaagaagt ggcaggagga gatggagctc taccgccaga aggtggagcc | 240 |
| gctgcgcgca gagctccaag agggcgcgcg ccagaagctg cacgagctgc aagagaagtt | 300 |
| gagcccactg ggcgaggaga tgcgcgaccg cgcgcgcgcc catgtggacg cgctgcgcac | 360 |
| gcatctggcc ccctacagcg acgagctgcg ccagcgcttg gccgcgcgcc ttgaggctct | 420 |
| caaggagaac ggcggcgcca gactggccga gtaccacgcc aaggccaccg agcatctgag | 480 |
| cacgctcagc gagaaggcca aacccgcgct cgaggacctc cgccaaggcc tgctgcccgt | 540 |
| gctggagagc ttcaaggtca gcttcctgag cgctctcgag gagtacacta agaagctcaa | 600 |
| cacccagtaa taagcttgc | 619 |

<210> SEQ ID NO 9
<211> LENGTH: 201
<212> TYPE: PRT
<213> ORGANISM: Artificial Sequence
<220> FEATURE:
<223> OTHER INFORMATION: MSP1 without His-tag

<400> SEQUENCE: 9

Met Ala Lys Leu Leu Asp Asn Trp Asp Ser Val Thr Ser Thr Phe Ser
1               5                   10                  15

Lys Leu Arg Glu Gln Leu Gly Pro Val Thr Gln Glu Phe Trp Asp Asn
            20                  25                  30

Leu Glu Lys Glu Thr Glu Gly Leu Arg Gln Glu Met Ser Lys Asp Leu
        35                  40                  45

Glu Glu Val Lys Ala Lys Val Gln Pro Tyr Leu Asp Asp Phe Gln Lys
    50                  55                  60

Lys Trp Gln Glu Met Glu Leu Tyr Arg Gln Lys Val Glu Pro Leu
65                  70                  75                  80

Arg Ala Glu Leu Gln Glu Gly Ala Arg Gln Lys Leu His Glu Leu Gln
                85                  90                  95

Glu Lys Leu Ser Pro Leu Gly Glu Glu Met Arg Asp Arg Ala Arg Ala
            100                 105                 110

His Val Asp Ala Leu Arg Thr His Leu Ala Pro Tyr Ser Asp Glu Leu
        115                 120                 125

Arg Gln Arg Leu Ala Ala Arg Leu Glu Ala Leu Lys Glu Asn Gly Gly
    130                 135                 140

Ala Arg Leu Ala Glu Tyr His Ala Lys Ala Thr Glu His Leu Ser Thr
145                 150                 155                 160

Leu Ser Glu Lys Ala Lys Pro Ala Leu Glu Asp Leu Arg Gln Gly Leu
                165                 170                 175

Leu Pro Val Leu Glu Ser Phe Lys Val Ser Phe Leu Ser Ala Leu Glu
            180                 185                 190

Glu Tyr Thr Lys Lys Leu Asn Thr Gln
        195                 200

<210> SEQ ID NO 10
<211> LENGTH: 27
<212> TYPE: DNA
<213> ORGANISM: Artificial Sequence
<220> FEATURE:
<223> OTHER INFORMATION: oligonucleotide primer

<400> SEQUENCE: 10

```
<210> SEQ ID NO 11
<211> LENGTH: 61
<212> TYPE: DNA
<213> ORGANISM: Artificial Sequence
<220> FEATURE:
<223> OTHER INFORMATION: oligonucleotide primer

<400> SEQUENCE: 11
tataccatgg gccatcatca tcatcatcat atagaaggaa gactaaagct ccttgacaac    60
t                                                                   61

<210> SEQ ID NO 12
<211> LENGTH: 52
<212> TYPE: DNA
<213> ORGANISM: Artificial Sequence
<220> FEATURE:
<223> OTHER INFORMATION: oligonucleotide primer

<400> SEQUENCE: 12
taagaagctc aacacccagg gtaccggtgg aggtagtgga ggtggtaccc ta           52

<210> SEQ ID NO 13
<211> LENGTH: 50
<212> TYPE: DNA
<213> ORGANISM: Artificial Sequence
<220> FEATURE:
<223> OTHER INFORMATION: oligonucleotide primer

<400> SEQUENCE: 13
cagggtaccg gtggaggtag tggaggtggt accctaaagc tccttgacaa              50

<210> SEQ ID NO 14
<211> LENGTH: 30
<212> TYPE: DNA
<213> ORGANISM: Artificial Sequence
<220> FEATURE:
<223> OTHER INFORMATION: oligonucleotide primer

<400> SEQUENCE: 14
gcaagcttat tactgggtgt tgagcttctt                                    30

<210> SEQ ID NO 15
<211> LENGTH: 9
<212> TYPE: PRT
<213> ORGANISM: artificial sequence
<220> FEATURE:
<223> OTHER INFORMATION: synthetic peptide of linker

<400> SEQUENCE: 15

Gly Thr Gly Gly Gly Ser Gly Gly Thr
1               5

<210> SEQ ID NO 16
<211> LENGTH: 1260
<212> TYPE: DNA
<213> ORGANISM: Artificial Sequence
<220> FEATURE:
<223> OTHER INFORMATION: nucleotide sequence encoding His-tagged MSP2

<400> SEQUENCE: 16
tataccatgg gccatcatca tcatcatcat atagaaggaa gactaaagct ccttgacaac    60
tgggacagcg tgacctccac cttcagcaag ctgcgcgaac agctcggccc tgtgacccag   120
```

(above ``taccatggca aagctccttg acaactg    27`` appears as the continuation from SEQ ID NO 10)

-continued

```
gagttctggg ataacctgga aaaggagaca gagggcctga ggcaggagat gagcaaggat      180
ctggaggagg tgaaggccaa ggtgcagccc tacctggacg acttccagaa gaagtggcag      240
gaggagatgg agctctaccg ccagaaggtg gagccgctgc gcgcagagct ccaagagggc      300
gcgcgccaga agctgcacga gctgcaagag aagctgagcc cactgggcga ggagatgcgc      360
gaccgcgcgc gcgcccatgt ggacgcgctg cgcacgcatc tggcccccta cagcgacgag      420
ctgcgccagc gcttggccgc gcgccttgag gctctcaagg agaacggcgg cgccagactg      480
gccgagtacc acgccaaggc caccgagcat ctgagcacgc tcagcgagaa ggccaagccc      540
gcgctcgagg acctccgcca aggcctgctg cccgtgctgg agagcttcaa ggtcagcttc      600
ctgagcgctc tcgaggagta cactaagaag ctcaacaccc agggtaccct aaagctcctt      660
gacaactggg acagcgtgac ctccaccttc agcaagctgc gcgaacagct cggccctgtg      720
acccaggagt tctgggataa cctggaaaag gagacagagg gcctgaggca ggagatgagc      780
aaggatctgg aggaggtgaa ggccaaggtg cagccctacc tggacgactt ccagaagaag      840
tgcaggagg  agatggagct ctaccgccag aaggtggagc cgctgcgcgc agagctccaa      900
gagggcgcgc gccagaagct gcacgagctg caagagaagc tgagcccact gggcgaggag      960
atgcgcgacc gcgcgcgcgc ccatgtggac gcgctgcgca cgcatctggc cccctacagc     1020
gacgagctgc gccagcgctt ggccgcgcgc cttgaggctc tcaaggagaa cggcggcgcc     1080
agactggccg agtaccacgc caaggccacc gagcatctga gcacgctcag cgagaaggcc     1140
aagcccgcgc tcgaggacct ccgccaaggc ctgctgcccg tgctggagag cttcaaggtc     1200
agcttcctga gcgctctcga ggagtacact aagaagctca cacccagta ataagcttgc     1260
```

<210> SEQ ID NO 17
<211> LENGTH: 414
<212> TYPE: PRT
<213> ORGANISM: Artificial Sequence
<220> FEATURE:
<223> OTHER INFORMATION: His-tagged MSP2

<400> SEQUENCE: 17

```
Met Gly His His His His His His Ile Glu Gly Arg Leu Lys Leu Leu
1               5                   10                  15

Asp Asn Trp Asp Ser Val Thr Ser Thr Phe Ser Lys Leu Arg Glu Gln
            20                  25                  30

Leu Gly Pro Val Thr Gln Glu Phe Trp Asp Asn Leu Glu Lys Glu Thr
        35                  40                  45

Glu Gly Leu Arg Gln Glu Met Ser Lys Asp Leu Glu Glu Val Lys Ala
    50                  55                  60

Lys Val Gln Pro Tyr Leu Asp Asp Phe Gln Lys Lys Trp Gln Glu Glu
65                  70                  75                  80

Met Glu Leu Tyr Arg Gln Lys Val Glu Pro Leu Arg Ala Glu Leu Gln
                85                  90                  95

Glu Gly Ala Arg Gln Lys Leu His Glu Leu Gln Glu Lys Leu Ser Pro
            100                 105                 110

Leu Gly Glu Glu Met Arg Asp Arg Ala Arg Ala His Val Asp Ala Leu
        115                 120                 125

Arg Thr His Leu Ala Pro Tyr Ser Asp Glu Leu Arg Gln Arg Leu Ala
    130                 135                 140

Ala Arg Leu Glu Ala Leu Lys Glu Asn Gly Gly Ala Arg Leu Ala Glu
145                 150                 155                 160
```

```
Tyr His Ala Lys Ala Thr Glu His Leu Ser Thr Leu Ser Glu Lys Ala
                165                 170                 175

Lys Pro Ala Leu Glu Asp Leu Arg Gln Gly Leu Leu Pro Val Leu Glu
            180                 185                 190

Ser Phe Lys Val Ser Phe Leu Ser Ala Leu Glu Glu Tyr Thr Lys Lys
        195                 200                 205

Leu Asn Thr Gln Gly Thr Leu Lys Leu Leu Asp Asn Trp Asp Ser Val
210                 215                 220

Thr Ser Thr Phe Ser Lys Leu Arg Glu Gln Leu Gly Pro Val Thr Gln
225                 230                 235                 240

Glu Phe Trp Asp Asn Leu Glu Lys Glu Thr Glu Gly Leu Arg Gln Glu
                245                 250                 255

Met Ser Lys Asp Leu Glu Glu Val Lys Ala Lys Val Gln Pro Tyr Leu
            260                 265                 270

Asp Asp Phe Gln Lys Lys Trp Gln Glu Glu Met Glu Leu Tyr Arg Gln
        275                 280                 285

Lys Val Glu Pro Leu Arg Ala Glu Leu Gln Glu Gly Ala Arg Gln Lys
290                 295                 300

Leu His Glu Leu Gln Glu Lys Leu Ser Pro Leu Gly Glu Glu Met Arg
305                 310                 315                 320

Asp Arg Ala Arg Ala His Val Asp Ala Leu Arg Thr His Leu Ala Pro
                325                 330                 335

Tyr Ser Asp Glu Leu Arg Gln Arg Leu Ala Ala Arg Leu Glu Ala Leu
            340                 345                 350

Lys Glu Asn Gly Gly Ala Arg Leu Ala Glu Tyr His Ala Lys Ala Thr
        355                 360                 365

Glu His Leu Ser Thr Leu Ser Glu Lys Ala Lys Pro Ala Leu Glu Asp
370                 375                 380

Leu Arg Gln Gly Leu Leu Pro Val Leu Glu Ser Phe Lys Val Ser Phe
385                 390                 395                 400

Leu Ser Ala Leu Glu Glu Tyr Thr Lys Lys Leu Asn Thr Gln
                405                 410

<210> SEQ ID NO 18
<211> LENGTH: 1282
<212> TYPE: DNA
<213> ORGANISM: Artificial Sequence
<220> FEATURE:
<223> OTHER INFORMATION: nucleotide sequence encoding His-tagged MSP2L

<400> SEQUENCE: 18
taccatgggc catcatcatc atcatcatat agaaggaaga ctaaagctcc ttgacaactg      60
ggacagcgtg acctccacct tcagcaagct gcgcgaacag ctcggccctg tgacccagga    120
gttctgggat aacctggaaa aggagacaga gggcctgagg caggagatga gcaaggatct    180
ggaggaggtg aaggccaagg tgcagcccta cctggacgac ttccagaaga gtggcagga    240 ggagatggag ctctaccgcc agaaggtgga gccgctgcgc gcagagctcc agagggcgc    300 cgccagaag ctgcacgagc tgcaagagaa gctgagccca ctgggcgagg agatgcgcga    360
ccgcgcgcgc gcccatgtgg acgcgctgcg cacgcatctg gcccctaca gcgacgagct    420 gcgccagcgc ttggccgcgc gccttgaggc tctcaaggag aacggcggcg ccagactggc    480
cgagtaccac gccaaggcca ccgagcatct gagcacgctc agcgagaagg ccaagcccgc    540
gctcgaggac ctccgccaag gcctgctgcc cgtgctggag agcttcaagg tcagcttcct    600
gagcgctctc gaggagtaca ctaagaagct caacacccag ggtaccggtg aggtagtgg    660
```

```
aggtggtacc ctaaagctcc ttgacaactg ggacagcgtg acctccacct tcagcaagct    720
gcgcgaacag ctcggccctg tgacccagga gttctgggat aacctggaaa aggagacaga    780
gggcctgagg caggagatga gcaaggatct ggaggaggtg aaggccaagg tgcagcccta    840
cctggacgac ttccagaaga agtggcagga ggagatggag ctctaccgcc agaaggtgga    900
gccgctgcgc gcagagctcc aagagggcgc gcgccagaag ctgcacgagc tgcaagagaa    960
gctgagccca ctgggcgagg agatgcgcga ccgcgcgcgc gcccatgtgg acgcgctgcg   1020
cacgcatctg gccccctaca gcgacgagct gcgccagcgc ttggccgcgc gccttgaggc   1080
tctcaaggag aacggcggcg ccagactggc cgagtaccac gccaaggcca ccgagcatct   1140
gagcacgctc agcgagaagg ccaagcccgc gctcgaggac ctccgccaag gcctgctgcc   1200
cgtgctggag agcttcaagg tcagcttcct gagcgctctc gaggagtaca ctaagaagct   1260
caacacccag taataagctt gc                                            1282

<210> SEQ ID NO 19
<211> LENGTH: 422
<212> TYPE: PRT
<213> ORGANISM: Artificial Sequence
<220> FEATURE:
<223> OTHER INFORMATION: His-tagged MSP2L

<400> SEQUENCE: 19

Met Gly His His His His His His Ile Glu Gly Arg Leu Lys Leu Leu
1               5                   10                  15

Asp Asn Trp Asp Ser Val Thr Ser Thr Phe Ser Lys Leu Arg Glu Gln
            20                  25                  30

Leu Gly Pro Val Thr Gln Glu Phe Trp Asp Asn Leu Glu Lys Glu Thr
        35                  40                  45

Glu Gly Leu Arg Gln Glu Met Ser Lys Asp Leu Glu Glu Val Lys Ala
    50                  55                  60

Lys Val Gln Pro Tyr Leu Asp Asp Phe Gln Lys Lys Trp Gln Glu Glu
65                  70                  75                  80

Met Glu Leu Tyr Arg Gln Lys Val Glu Pro Leu Arg Ala Glu Leu Gln
                85                  90                  95

Glu Gly Ala Arg Gln Lys Leu His Glu Leu Gln Glu Lys Leu Ser Pro
            100                 105                 110

Leu Gly Glu Glu Met Arg Asp Arg Ala Arg Ala His Val Asp Ala Leu
        115                 120                 125

Arg Thr His Leu Ala Pro Tyr Ser Asp Glu Leu Arg Gln Arg Leu Ala
    130                 135                 140

Ala Arg Leu Glu Ala Leu Lys Glu Asn Gly Gly Ala Arg Leu Ala Glu
145                 150                 155                 160

Tyr His Ala Lys Ala Thr Glu His Leu Ser Thr Leu Ser Glu Lys Ala
                165                 170                 175

Lys Pro Ala Leu Glu Asp Leu Arg Gln Gly Leu Leu Pro Val Leu Glu
            180                 185                 190

Ser Phe Lys Val Ser Phe Leu Ser Ala Leu Glu Glu Tyr Thr Lys Lys
        195                 200                 205

Leu Asn Thr Gln Gly Thr Gly Gly Ser Gly Gly Thr Leu Lys
    210                 215                 220

Leu Leu Asp Asn Trp Asp Ser Val Thr Ser Thr Phe Ser Lys Leu Arg
225                 230                 235                 240

Glu Gln Leu Gly Pro Val Thr Gln Glu Phe Trp Asp Asn Leu Glu Lys
```

-continued

```
                245                 250                 255
Glu Thr Glu Gly Leu Arg Gln Glu Met Ser Lys Asp Leu Glu Val
                260                 265                 270
Lys Ala Lys Val Gln Pro Tyr Leu Asp Asp Phe Gln Lys Lys Trp Gln
            275                 280                 285
Glu Glu Met Glu Leu Tyr Arg Gln Lys Val Glu Pro Leu Arg Ala Glu
        290                 295                 300
Leu Gln Glu Gly Ala Arg Gln Lys Leu His Glu Leu Gln Glu Lys Leu
305                 310                 315                 320
Ser Pro Leu Gly Glu Glu Met Arg Asp Arg Ala Arg Ala His Val Asp
                325                 330                 335
Ala Leu Arg Thr His Leu Ala Pro Tyr Ser Asp Glu Leu Arg Gln Arg
            340                 345                 350
Leu Ala Ala Arg Leu Glu Ala Leu Lys Glu Asn Gly Gly Ala Arg Leu
        355                 360                 365
Ala Glu Tyr His Ala Lys Ala Thr Glu His Leu Ser Thr Leu Ser Glu
    370                 375                 380
Lys Ala Lys Pro Ala Leu Glu Asp Leu Arg Gln Gly Leu Leu Pro Val
385                 390                 395                 400
Leu Glu Ser Phe Lys Val Ser Phe Leu Ser Ala Leu Glu Glu Tyr Thr
                405                 410                 415
Lys Lys Leu Asn Thr Gln
            420
```

```
<210> SEQ ID NO 20
<211> LENGTH: 43
<212> TYPE: DNA
<213> ORGANISM: Artificial Sequence
<220> FEATURE:
<223> OTHER INFORMATION: oligonucleotide primer

<400> SEQUENCE: 20
tggagctcta ccgccagaag gtggagccct acagcgacga gct            43

<210> SEQ ID NO 21
<211> LENGTH: 30
<212> TYPE: DNA
<213> ORGANISM: Artificial Sequence
<220> FEATURE:
<223> OTHER INFORMATION: oligonucleotide primer

<400> SEQUENCE: 21
gcaagcttat tactgggtgt tgagcttctt                           30

<210> SEQ ID NO 22
<211> LENGTH: 522
<212> TYPE: DNA
<213> ORGANISM: Artificial Sequence
<220> FEATURE:
<223> OTHER INFORMATION: nucleotide sequence encoding MSP1D5D6

<400> SEQUENCE: 22
tataccatgg gccatcatca tcatcatcat atagaaggaa gactaaagct ccttgacaac    60
tgggacagcg tgacctccac cttcagcaag ctgcgcgaac agctcggccc tgtgacccag   120
gagttctggg ataacctgga aaaggagaca gagggcctga gcaggagat gagcaaggat   180 ctggaggagg tgaaggccaa ggtgcagccc tacctggacg acttccagaa gaagtggcag   240
gaggagatgg agctctaccg ccagaaggtg gagccctaca gcgacgagct gcgccagcgc   300
```

```
ttggccgcgc gccttgaggc tctcaaggag aacggcggcg ccagactggc cgagtaccac    360
gccaaggcca ccgagcatct gagcacgctc agcgagaagg ccaaacccgc gctcgaggac    420
ctccgccaag gcctgctgcc cgtgctggag agcttcaagg tcagcttcct gagcgctctc    480
gaggagtaca ctaagaagct caacacccag taataagctt gc                      522
```

```
<210> SEQ ID NO 23
<211> LENGTH: 168
<212> TYPE: PRT
<213> ORGANISM: Artificial Sequence
<220> FEATURE:
<223> OTHER INFORMATION: His-tagged MSP1D5D6

<400> SEQUENCE: 23

Met Gly His His His His His His Ile Glu Gly Arg Leu Lys Leu Leu
1               5                   10                  15

Asp Asn Trp Asp Ser Val Thr Ser Thr Phe Ser Lys Leu Arg Glu Gln
            20                  25                  30

Leu Gly Pro Val Thr Gln Glu Phe Trp Asp Asn Leu Glu Lys Glu Thr
        35                  40                  45

Glu Gly Leu Arg Gln Glu Met Ser Lys Asp Leu Glu Glu Val Lys Ala
    50                  55                  60

Lys Val Gln Pro Tyr Leu Asp Asp Phe Gln Lys Lys Trp Gln Glu Glu
65                  70                  75                  80

Met Glu Leu Tyr Arg Gln Lys Val Glu Pro Tyr Ser Asp Glu Leu Arg
                85                  90                  95

Gln Arg Leu Ala Ala Arg Leu Glu Ala Leu Lys Glu Asn Gly Gly Ala
            100                 105                 110

Arg Leu Ala Glu Tyr His Ala Lys Ala Thr Glu His Leu Ser Thr Leu
        115                 120                 125

Ser Glu Lys Ala Lys Pro Ala Leu Glu Asp Leu Arg Gln Gly Leu Leu
    130                 135                 140

Pro Val Leu Glu Ser Phe Lys Val Ser Phe Leu Ser Ala Leu Glu Glu
145                 150                 155                 160

Tyr Thr Lys Lys Leu Asn Thr Gln
                165
```

```
<210> SEQ ID NO 24
<211> LENGTH: 29
<212> TYPE: DNA
<213> ORGANISM: Artificial Sequence
<220> FEATURE:
<223> OTHER INFORMATION: oligonucleotide primer

<400> SEQUENCE: 24
cagaattcgc tagccgagta ccacgccaa                                      29
```

```
<210> SEQ ID NO 25
<211> LENGTH: 30
<212> TYPE: DNA
<213> ORGANISM: Artificial Sequence
<220> FEATURE:
<223> OTHER INFORMATION: oligonucleotide primer

<400> SEQUENCE: 25
gcaagcttat tactgggtgt tgagcttctt                                     30
```

```
<210> SEQ ID NO 26
<211> LENGTH: 30
<212> TYPE: DNA
```

```
<213> ORGANISM: Artificial Sequence
<220> FEATURE:
<223> OTHER INFORMATION: oligonucleotide primer

<400> SEQUENCE: 26
ataccatggg ccatcatcat catcatcata                              30

<210> SEQ ID NO 27
<211> LENGTH: 33
<212> TYPE: DNA
<213> ORGANISM: Artificial Sequence
<220> FEATURE:
<223> OTHER INFORMATION: oligonucleotide primer

<400> SEQUENCE: 27
cagaattcgc tagcctggcg ctcaacttct ctt                          33

<210> SEQ ID NO 28
<211> LENGTH: 522
<212> TYPE: DNA
<213> ORGANISM: Artificial Sequence
<220> FEATURE:
<223> OTHER INFORMATION: nucleotide sequence encoding His-tagged MSP1D6

<400> SEQUENCE: 28
tataccatgg gccatcatca tcatcatcat atagaaggaa gactaaagct ccttgacaac     60
tgggacagcg tgacctccac cttcagcaag ctgcgcgaac agctcggccc tgtgacccag    120
gagttctggg ataacctgga aaaggagaca gagggcctga ggcaggagat gagcaaggat    180
ctggaggagg tgaaggccaa ggtgcagccc tacctggacg acttccagaa gaagtggcag    240
gaggagatga gctctaccg ccagaaggtg gagccgctgc gcgcagagct ccaagagggc    300
gcgcgccaga agctgcacga gctgcaagag aagttgagcg ccaggctagc cgagtaccac    360
gccaaggcca ccgagcatct gagcacgctc agcgagaagg ccaaacccgc gctcgaggac    420
ctccgccaag gcctgctgcc cgtgctggag agcttcaagg tcagcttcct gagcgctctc    480
gaggagtaca ctaagaagct caacacccag taataagctt gc                      522

<210> SEQ ID NO 29
<211> LENGTH: 168
<212> TYPE: PRT
<213> ORGANISM: Artificial Sequence
<220> FEATURE:
<223> OTHER INFORMATION: His-tagged MSP1D6

<400> SEQUENCE: 29

Met Gly His His His His His His Ile Glu Gly Arg Leu Lys Leu Leu
1               5                   10                  15

Asp Asn Trp Asp Ser Val Thr Ser Thr Phe Ser Lys Leu Arg Glu Gln
            20                  25                  30

Leu Gly Pro Val Thr Gln Glu Phe Trp Asp Asn Leu Glu Lys Glu Thr
        35                  40                  45

Glu Gly Leu Arg Gln Glu Met Ser Lys Asp Leu Glu Glu Val Lys Ala
    50                  55                  60

Lys Val Gln Pro Tyr Leu Asp Asp Phe Gln Lys Lys Trp Gln Glu Glu
65                  70                  75                  80

Met Glu Leu Tyr Arg Gln Lys Val Glu Pro Leu Arg Ala Glu Leu Gln
                85                  90                  95

Glu Gly Ala Arg Gln Lys Leu His Glu Leu Gln Glu Lys Leu Ser Ala
            100                 105                 110
```

```
Arg Leu Ala Glu Tyr His Ala Lys Ala Thr Glu His Leu Ser Thr Leu
        115                 120                 125

Ser Glu Lys Ala Lys Pro Ala Leu Glu Asp Leu Arg Gln Gly Leu Leu
130                 135                 140

Pro Val Leu Glu Ser Phe Lys Val Ser Phe Leu Ser Ala Leu Glu Glu
145                 150                 155                 160

Tyr Thr Lys Lys Leu Asn Thr Gln
                165
```

<210> SEQ ID NO 30
<211> LENGTH: 77
<212> TYPE: DNA
<213> ORGANISM: Artificial Sequence
<220> FEATURE:
<223> OTHER INFORMATION: synthetic oligonucleotide

<400> SEQUENCE: 30

| | |
|---|---|
| taccatgggt catcatcatc atcatcacat tgagggacgt ctgaagctgt tggacaattg | 60 |
| ggactctgtt acgtcta | 77 |

<210> SEQ ID NO 31
<211> LENGTH: 62
<212> TYPE: DNA
<213> ORGANISM: Artificial Sequence
<220> FEATURE:
<223> OTHER INFORMATION: synthetic oligonucleotide

<400> SEQUENCE: 31

| | |
|---|---|
| aggaattctg ggacaacctg gaaaagaaa ccgagggact gcgtcaggaa atgtccaaag | 60 |
| at | 62 |

<210> SEQ ID NO 32
<211> LENGTH: 54
<212> TYPE: DNA
<213> ORGANISM: Artificial Sequence
<220> FEATURE:
<223> OTHER INFORMATION: synthetic oligonucleotide

<400> SEQUENCE: 32

| | |
|---|---|
| tatctagatg actttcagaa aaaatggcag gaagagatgg aattatatcg tcaa | 54 |

<210> SEQ ID NO 33
<211> LENGTH: 73
<212> TYPE: DNA
<213> ORGANISM: Artificial Sequence
<220> FEATURE:
<223> OTHER INFORMATION: synthetic oligonucleotide

<400> SEQUENCE: 33

| | |
|---|---|
| atgagctcca agagaagctc agcccattag gcgaagaaat gcgcgatcgc gcccgtgcac | 60 |
| atgttgatgc act | 73 |

<210> SEQ ID NO 34
<211> LENGTH: 65
<212> TYPE: DNA
<213> ORGANISM: Artificial Sequence
<220> FEATURE:
<223> OTHER INFORMATION: synthetic oligonucleotide

<400> SEQUENCE: 34

| | |
|---|---|
| gtctcgaggc gctgaaagaa aacgggggtg cccgcttggc tgagtaccac gcgaaagcga | 60 |
| cagaa | 65 |

<210> SEQ ID NO 35
<211> LENGTH: 56
<212> TYPE: DNA
<213> ORGANISM: Artificial Sequence
<220> FEATURE:
<223> OTHER INFORMATION: synthetic oligonucleotide

<400> SEQUENCE: 35
gaagatctac gccagggctt attgcctgtt cttgagagct ttaaagtcag ttttct        56

<210> SEQ ID NO 36
<211> LENGTH: 61
<212> TYPE: DNA
<213> ORGANISM: Artificial Sequence
<220> FEATURE:
<223> OTHER INFORMATION: synthetic oligonucleotide

<400> SEQUENCE: 36
cagaattcct gcgtcacggg gcccagttgt tcgcgaagtt tactgaaggt agacgtaaca    60
g                                                                    61

<210> SEQ ID NO 37
<211> LENGTH: 55
<212> TYPE: DNA
<213> ORGANISM: Artificial Sequence
<220> FEATURE:
<223> OTHER INFORMATION: synthetic oligonucleotide

<400> SEQUENCE: 37
tcatctagat atggctgaac cttggccttc acctcttcta aatctttgga cattt         55

<210> SEQ ID NO 38
<211> LENGTH: 80
<212> TYPE: DNA
<213> ORGANISM: Artificial Sequence
<220> FEATURE:
<223> OTHER INFORMATION: synthetic oligonucleotide

<400> SEQUENCE: 38
tggagctcat ggagtttttg gcgtgccccc tcttgcagtt ccgcacgcag cggttccacc    60
ttttgacgat ataattccat                                                80

<210> SEQ ID NO 39
<211> LENGTH: 76
<212> TYPE: DNA
<213> ORGANISM: Artificial Sequence
<220> FEATURE:
<223> OTHER INFORMATION: synthetic oligonucleotide

<400> SEQUENCE: 39
gcctcgagac gtgcggccaa acgctggcga agttcatccg aatacggcgc caaatgagtc    60
cggagtgcat caacat                                                    76

<210> SEQ ID NO 40
<211> LENGTH: 61
<212> TYPE: DNA
<213> ORGANISM: Artificial Sequence
<220> FEATURE:
<223> OTHER INFORMATION: synthetic oligonucleotide

<400> SEQUENCE: 40
gtagatcttc cagcgccggt ttcgcttttt cgctcaaggt gctcaggtgt tctgtcgctt    60

-continued

| | |
|---|---|
| t | 61 |

<210> SEQ ID NO 41
<211> LENGTH: 66
<212> TYPE: DNA
<213> ORGANISM: Artificial Sequence
<220> FEATURE:
<223> OTHER INFORMATION: synthetic oligonucleotide

<400> SEQUENCE: 41

| | |
|---|---|
| ccaagcttat tactgggtat tcagctttt agtatattct tccagagctg acagaaaact | 60 |
| gacttt | 66 |

<210> SEQ ID NO 42
<211> LENGTH: 651
<212> TYPE: DNA
<213> ORGANISM: Artificial Sequence
<220> FEATURE:
<223> OTHER INFORMATION: full synthetic sequence encoding MSP1

<400> SEQUENCE: 42

| | |
|---|---|
| accatgggtc atcatcatca tcatcacatt gagggacgtc tgaagctgtt ggacaattgg | 60 |
| gactctgtta cgtctacctt cagtaaactt cgcgaacaac tgggccccgt gacgcaggaa | 120 |
| ttctgggaca acctggaaaa agaaaccgag ggactgcgtc aggaaatgtc caaagattta | 180 |
| gaagaggtga aggccaaggt tcagccatat ctagatgact tcagaaaaaa atggcaggaa | 240 |
| gagatggaat tatatcgtca aaaggtggaa ccgctgcgtg cggaactgca agaggggca | 300 |
| cgccaaaaac tccatgagct ccaagagaag ctcagcccat aggcgaaga aatgcgcgat | 360 |
| cgcgcccgtg cacatgttga tgcactccgg actcatttgg cgccgtattc ggatgaactt | 420 |
| cgccagcgtt tggccgcacg tctcgaggcg ctgaaagaaa acggggtgc ccgcttggct | 480 |
| gagtaccacg cgaaagcgac agaacacctg agcaccttga gcgaaaaagc gaaaccggcg | 540 |
| ctggaagatc tacgccaggg cttattgcct gttcttgaga gctttaaagt cagttttctg | 600 |
| tcagctctgg aagaatatac taaaaagctg aatacccagt aataagcttg g | 651 |

<210> SEQ ID NO 43
<211> LENGTH: 201
<212> TYPE: PRT
<213> ORGANISM: Artificial Sequence
<220> FEATURE:
<223> OTHER INFORMATION: His-tagged MSP1D3

<400> SEQUENCE: 43

Met Gly His His His His His His Ile Glu Gly Arg Leu Lys Leu Leu
1               5                   10                  15

Asp Asn Trp Asp Ser Val Thr Ser Thr Phe Ser Lys Leu Arg Glu Gln
            20                  25                  30

Leu Gly Pro Val Thr Gln Glu Phe Trp Asp Asn Leu Glu Lys Glu Thr
        35                  40                  45

Glu Gly Leu Arg Gln Glu Met Ser Pro Tyr Leu Asp Asp Phe Gln Lys
    50                  55                  60

Lys Trp Gln Glu Glu Met Glu Leu Tyr Arg Gln Lys Val Glu Pro Leu
65                  70                  75                  80

Arg Ala Glu Leu Gln Glu Gly Ala Arg Gln Lys Leu His Glu Leu Gln
                85                  90                  95

Glu Lys Leu Ser Pro Leu Gly Glu Glu Met Arg Asp Arg Ala Arg Ala
            100                 105                 110

His Val Asp Ala Leu Arg Thr His Leu Ala Pro Tyr Ser Asp Glu Leu
            115                 120                 125

Arg Gln Arg Leu Ala Ala Arg Leu Glu Ala Leu Lys Glu Asn Gly Gly
        130                 135                 140

Ala Arg Leu Ala Glu Tyr His Ala Lys Ala Thr Glu His Leu Ser Thr
145                 150                 155                 160

Leu Ser Glu Lys Ala Lys Pro Ala Leu Glu Asp Leu Arg Gln Gly Leu
                165                 170                 175

Leu Pro Val Leu Glu Ser Phe Lys Val Ser Phe Leu Ser Ala Leu Glu
            180                 185                 190

Glu Tyr Thr Lys Lys Leu Asn Thr Gln
        195                 200

<210> SEQ ID NO 44
<211> LENGTH: 201
<212> TYPE: PRT
<213> ORGANISM: Artificial Sequence
<220> FEATURE:
<223> OTHER INFORMATION: His-tagged MSP1D9

<400> SEQUENCE: 44

Met Gly His His His His His His Ile Glu Gly Arg Leu Lys Leu Leu
1               5                   10                  15

Asp Asn Trp Asp Ser Val Thr Ser Thr Phe Ser Lys Leu Arg Glu Gln
            20                  25                  30

Leu Gly Pro Val Thr Gln Glu Phe Trp Asp Asn Leu Glu Lys Glu Thr
        35                  40                  45

Glu Gly Leu Arg Gln Glu Met Ser Lys Asp Leu Glu Glu Val Lys Ala
    50                  55                  60

Lys Val Gln Pro Tyr Leu Asp Asp Phe Gln Lys Lys Trp Gln Glu Glu
65                  70                  75                  80

Met Glu Leu Tyr Arg Gln Lys Val Glu Pro Leu Arg Ala Glu Leu Gln
                85                  90                  95

Glu Gly Ala Arg Gln Lys Leu His Glu Leu Gln Glu Lys Leu Ser Pro
            100                 105                 110

Leu Gly Glu Glu Met Arg Asp Arg Ala Arg Ala His Val Asp Ala Leu
        115                 120                 125

Arg Thr His Leu Ala Pro Tyr Ser Asp Glu Leu Arg Gln Arg Leu Ala
    130                 135                 140

Ala Arg Leu Glu Ala Leu Lys Glu Asn Gly Gly Ala Arg Leu Ala Glu
145                 150                 155                 160

Tyr His Ala Lys Ala Thr Glu His Leu Ser Thr Leu Ser Glu Lys Ala
                165                 170                 175

Lys Pro Val Leu Glu Ser Phe Lys Val Ser Phe Leu Ser Ala Leu Glu
            180                 185                 190

Glu Tyr Thr Lys Lys Leu Asn Thr Gln
        195                 200

<210> SEQ ID NO 45
<211> LENGTH: 392
<212> TYPE: PRT
<213> ORGANISM: Artificial Sequence
<220> FEATURE:
<223> OTHER INFORMATION: His-tagged MSP2 delta 1

<400> SEQUENCE: 45

Met Gly His His His His His His Ile Glu Gly Arg Leu Lys Leu Leu
1               5                   10                  15

```
Asp Asn Trp Asp Ser Val Thr Ser Thr Phe Ser Lys Leu Arg Glu Gln
             20                  25                  30

Leu Gly Pro Val Thr Gln Glu Phe Trp Asp Asn Leu Glu Lys Glu Thr
         35                  40                  45

Glu Gly Leu Arg Gln Glu Met Ser Pro Tyr Leu Asp Asp Phe Gln Lys
     50                  55                  60

Lys Trp Gln Glu Glu Met Glu Leu Tyr Arg Gln Lys Val Glu Pro Leu
 65                  70                  75                  80

Arg Ala Glu Leu Gln Glu Gly Ala Arg Gln Lys Leu His Glu Leu Gln
                 85                  90                  95

Glu Lys Leu Ser Pro Leu Gly Glu Glu Met Arg Asp Arg Ala Arg Ala
            100                 105                 110

His Val Asp Ala Leu Arg Thr His Leu Ala Pro Tyr Ser Asp Glu Leu
        115                 120                 125

Arg Gln Arg Leu Ala Ala Arg Leu Glu Ala Leu Lys Glu Asn Gly Gly
    130                 135                 140

Ala Arg Leu Ala Glu Tyr His Ala Lys Ala Thr Glu His Leu Ser Thr
145                 150                 155                 160

Leu Ser Glu Lys Ala Lys Pro Ala Leu Glu Asp Leu Arg Gln Gly Leu
                165                 170                 175

Leu Pro Val Leu Glu Ser Phe Lys Val Ser Phe Leu Ser Ala Leu Glu
            180                 185                 190

Glu Tyr Thr Lys Lys Leu Asn Thr Gln Gly Thr Leu Lys Leu Leu Asp
        195                 200                 205

Asn Trp Asp Ser Val Thr Ser Thr Phe Ser Lys Leu Arg Glu Gln Leu
    210                 215                 220

Gly Pro Val Thr Gln Glu Phe Trp Asp Asn Leu Glu Lys Glu Thr Glu
225                 230                 235                 240

Gly Leu Arg Gln Glu Met Ser Pro Tyr Leu Asp Asp Phe Gln Lys Lys
                245                 250                 255

Trp Gln Glu Glu Met Glu Leu Tyr Arg Gln Lys Val Glu Pro Leu Arg
            260                 265                 270

Ala Glu Leu Gln Glu Gly Ala Arg Gln Lys Leu His Glu Leu Gln Glu
        275                 280                 285

Lys Leu Ser Pro Leu Gly Glu Glu Met Arg Asp Arg Ala Arg Ala His
    290                 295                 300

Val Asp Ala Leu Arg Thr His Leu Ala Pro Tyr Ser Asp Glu Leu Arg
305                 310                 315                 320

Gln Arg Leu Ala Ala Arg Leu Glu Ala Leu Lys Glu Asn Gly Gly Ala
                325                 330                 335

Arg Leu Ala Glu Tyr His Ala Lys Ala Thr Glu His Leu Ser Thr Leu
            340                 345                 350

Ser Glu Lys Ala Lys Pro Ala Leu Glu Asp Leu Arg Gln Gly Leu Leu
        355                 360                 365

Pro Val Leu Glu Ser Phe Lys Val Ser Phe Leu Ser Ala Leu Glu Glu
    370                 375                 380

Tyr Thr Lys Lys Leu Asn Thr Gln
385                 390

<210> SEQ ID NO 46
<211> LENGTH: 4
<212> TYPE: PRT
<213> ORGANISM: Artificial Sequence
<220> FEATURE:
```

```
<223> OTHER INFORMATION: synthetic peptide of linker
<220> FEATURE:
<221> NAME/KEY: MISC_FEATURE
<222> LOCATION: (1)..(4)
<223> OTHER INFORMATION: X is Ser or Thr

<400> SEQUENCE: 46

Gly Gly Gly Xaa
1

<210> SEQ ID NO 47
<211> LENGTH: 12
<212> TYPE: PRT
<213> ORGANISM: Artificial Sequence
<220> FEATURE:
<223> OTHER INFORMATION: artificial sequence of His-tag

<400> SEQUENCE: 47

Met Gly His His His His His His Ile Glu Gly Arg
1               5                   10

<210> SEQ ID NO 48
<211> LENGTH: 23
<212> TYPE: PRT
<213> ORGANISM: Artificial Sequence
<220> FEATURE:
<223> OTHER INFORMATION: artificial sequence of HisTEV

<400> SEQUENCE: 48

Met Gly His His His His His His Asp Tyr Asp Ile Pro Thr Thr
1               5                   10                  15

Glu Asn Leu Tyr Phe Gln Gly
            20

<210> SEQ ID NO 49
<211> LENGTH: 22
<212> TYPE: PRT
<213> ORGANISM: Artificial Sequence
<220> FEATURE:
<223> OTHER INFORMATION: artificial sequence of Helix 1

<400> SEQUENCE: 49

Leu Lys Leu Leu Asp Asn Trp Asp Ser Val Thr Ser Thr Phe Ser Lys
1               5                   10                  15

Leu Arg Glu Gln Leu Gly
            20

<210> SEQ ID NO 50
<211> LENGTH: 22
<212> TYPE: PRT
<213> ORGANISM: Artificial Sequence
<220> FEATURE:
<223> OTHER INFORMATION: artificial sequence of Helix 2

<400> SEQUENCE: 50

Pro Val Thr Gln Glu Phe Trp Asp Asn Leu Glu Lys Glu Thr Glu Gly
1               5                   10                  15

Leu Arg Gln Glu Met Ser
            20

<210> SEQ ID NO 51
<211> LENGTH: 11
<212> TYPE: PRT
<213> ORGANISM: Artificial Sequence
<220> FEATURE:
<223> OTHER INFORMATION: artificial sequence of Helix 3
```

```
<400> SEQUENCE: 51

Lys Asp Leu Glu Glu Val Lys Ala Lys Val Gln
1               5                   10

<210> SEQ ID NO 52
<211> LENGTH: 22
<212> TYPE: PRT
<213> ORGANISM: Artificial Sequence
<220> FEATURE:
<223> OTHER INFORMATION: artificial sequence of Helix 4

<400> SEQUENCE: 52

Pro Tyr Leu Asp Asp Phe Gln Lys Lys Trp Gln Glu Glu Met Glu Leu
1               5                   10                  15

Tyr Arg Gln Lys Val Glu
            20

<210> SEQ ID NO 53
<211> LENGTH: 22
<212> TYPE: PRT
<213> ORGANISM: Artificial Sequence
<220> FEATURE:
<223> OTHER INFORMATION: artificial sequence of Helix 5

<400> SEQUENCE: 53

Pro Leu Arg Ala Glu Leu Gln Glu Gly Ala Arg Gln Lys Leu His Glu
1               5                   10                  15

Leu Gln Glu Lys Leu Ser
            20

<210> SEQ ID NO 54
<211> LENGTH: 22
<212> TYPE: PRT
<213> ORGANISM: Artificial Sequence
<220> FEATURE:
<223> OTHER INFORMATION: artificial sequence of Helix 6

<400> SEQUENCE: 54

Pro Leu Gly Glu Glu Met Arg Asp Arg Ala Arg Ala His Val Asp Ala
1               5                   10                  15

Leu Arg Thr His Leu Ala
            20

<210> SEQ ID NO 55
<211> LENGTH: 22
<212> TYPE: PRT
<213> ORGANISM: Artificial Sequence
<220> FEATURE:
<223> OTHER INFORMATION: artificial sequence of Helix 7

<400> SEQUENCE: 55

Pro Tyr Ser Asp Glu Leu Arg Gln Arg Leu Ala Ala Arg Leu Glu Ala
1               5                   10                  15

Leu Lys Glu Asn Gly Gly
            20

<210> SEQ ID NO 56
<211> LENGTH: 22
<212> TYPE: PRT
<213> ORGANISM: Artificial Sequence
<220> FEATURE:
<223> OTHER INFORMATION: artificial sequence of Helix 8

<400> SEQUENCE: 56
```

Ala Arg Leu Ala Glu Tyr His Ala Lys Ala Thr Glu His Leu Ser Thr
1               5                   10                  15

Leu Ser Glu Lys Ala Lys
            20

<210> SEQ ID NO 57
<211> LENGTH: 11
<212> TYPE: PRT
<213> ORGANISM: Artificial Sequence
<220> FEATURE:
<223> OTHER INFORMATION: artificial sequence of Helix 9

<400> SEQUENCE: 57

Pro Ala Leu Glu Asp Leu Arg Gln Gly Leu Leu
1               5                   10

<210> SEQ ID NO 58
<211> LENGTH: 24
<212> TYPE: PRT
<213> ORGANISM: Artificial Sequence
<220> FEATURE:
<223> OTHER INFORMATION: artificial sequence of Helix 10

<400> SEQUENCE: 58

Pro Val Leu Glu Ser Phe Lys Val Ser Phe Leu Ser Ala Leu Glu Glu
1               5                   10                  15

Tyr Thr Lys Lys Leu Asn Thr Gln
            20

<210> SEQ ID NO 59
<211> LENGTH: 11
<212> TYPE: PRT
<213> ORGANISM: Artificial Sequence
<220> FEATURE:
<223> OTHER INFORMATION: artificial sequence of Helix 0.5

<400> SEQUENCE: 59

Ser Thr Phe Ser Lys Leu Arg Glu Gln Leu Gly
1               5                   10

<210> SEQ ID NO 60
<211> LENGTH: 36
<212> TYPE: DNA
<213> ORGANISM: Artificial Sequence
<220> FEATURE:
<223> OTHER INFORMATION: sequence encoding His-tag

<400> SEQUENCE: 60
atgggtcatc atcatcatca tcacattgag ggacgt                            36

<210> SEQ ID NO 61
<211> LENGTH: 69
<212> TYPE: DNA
<213> ORGANISM: Artificial Sequence
<220> FEATURE:
<223> OTHER INFORMATION: sequence encoding His-TEV

<400> SEQUENCE: 61
atgggtcatc atcatcatca tcatcacgat tatgatattc ctactactga gaatttgtat    60
tttcagggt                                                            69

<210> SEQ ID NO 62
<211> LENGTH: 66
<212> TYPE: DNA

```
<213> ORGANISM: Artificial Sequence
<220> FEATURE:
<223> OTHER INFORMATION: sequence encoding Helix 1

<400> SEQUENCE: 62
ctgaagctgt tggacaattg ggactctgtt acgtctacct tcagtaaact tcgcgaacaa    60
ctgggc                                                                66

<210> SEQ ID NO 63
<211> LENGTH: 66
<212> TYPE: DNA
<213> ORGANISM: Artificial Sequence
<220> FEATURE:
<223> OTHER INFORMATION: sequence encoding Helix 2

<400> SEQUENCE: 63
cccgtgacgc aggaattctg ggacaacctg gaaaagaaa ccgagggact gcgtcaggaa     60
atgtcc                                                                66

<210> SEQ ID NO 64
<211> LENGTH: 33
<212> TYPE: DNA
<213> ORGANISM: Artificial Sequence
<220> FEATURE:
<223> OTHER INFORMATION: sequence encoding Helix 3

<400> SEQUENCE: 64
aaagatttag aagaggtgaa ggccaaggtt cag                                  33

<210> SEQ ID NO 65
<211> LENGTH: 66
<212> TYPE: DNA
<213> ORGANISM: Artificial Sequence
<220> FEATURE:
<223> OTHER INFORMATION: sequence encoding Helix 4

<400> SEQUENCE: 65
ccatatctcg atgactttca gaaaaaatgg caggaagaga tggaattata tcgtcaaaag    60
gtggaa                                                                66

<210> SEQ ID NO 66
<211> LENGTH: 66
<212> TYPE: DNA
<213> ORGANISM: Artificial Sequence
<220> FEATURE:
<223> OTHER INFORMATION: sequence encoding Helix 5

<400> SEQUENCE: 66
ccgctgcgtg cggaactgca agaggggca cgccaaaaac tccatgagct ccaagagaag      60
ctcagc                                                                66

<210> SEQ ID NO 67
<211> LENGTH: 66
<212> TYPE: DNA
<213> ORGANISM: Artificial Sequence
<220> FEATURE:
<223> OTHER INFORMATION: sequence encoding Helix 6

<400> SEQUENCE: 67
ccattaggcg aagaaatgcg cgatcgcgcc cgtgcacatg ttgatgcact ccggactcat    60
ttggcg                                                                66
```

<210> SEQ ID NO 68
<211> LENGTH: 66
<212> TYPE: DNA
<213> ORGANISM: Artificial Sequence
<220> FEATURE:
<223> OTHER INFORMATION: sequence encoding Helix 7

<400> SEQUENCE: 68
ccgtattcgg atgaacttcg ccagcgtttg gccgcacgtc tcgaggcgct gaaagaaaac    60
gggggt    66

<210> SEQ ID NO 69
<211> LENGTH: 66
<212> TYPE: DNA
<213> ORGANISM: Artificial Sequence
<220> FEATURE:
<223> OTHER INFORMATION: sequence encoding Helix 8

<400> SEQUENCE: 69
gcccgcttgg ctgagtacca cgcgaaagcg acagaacacc tgagcacctt gagcgaaaaa    60
gcgaaa    66

<210> SEQ ID NO 70
<211> LENGTH: 33
<212> TYPE: DNA
<213> ORGANISM: Artificial Sequence
<220> FEATURE:
<223> OTHER INFORMATION: sequence encoding Helix 9

<400> SEQUENCE: 70
ccggcgctgg aagatctacg ccagggctta ttg    33

<210> SEQ ID NO 71
<211> LENGTH: 72
<212> TYPE: DNA
<213> ORGANISM: Artificial Sequence
<220> FEATURE:
<223> OTHER INFORMATION: sequence encoding Helix 10

<400> SEQUENCE: 71
cctgttcttg agagctttaa agtcagtttt ctgtcagctc tggaagaata tactaaaaag    60
ctgaataccc ag    72

<210> SEQ ID NO 72
<211> LENGTH: 33
<212> TYPE: DNA
<213> ORGANISM: Artificial Sequence
<220> FEATURE:
<223> OTHER INFORMATION: sequence encoding Helix 0.5

<400> SEQUENCE: 72
tctaccttca gtaaacttcg cgaacaactg ggc    33

<210> SEQ ID NO 73
<211> LENGTH: 234
<212> TYPE: PRT
<213> ORGANISM: Artificial Sequence
<220> FEATURE:
<223> OTHER INFORMATION: artificial sequence of His-tagged MSP1E1

<400> SEQUENCE: 73

Met Gly His His His His His His Ile Glu Gly Arg Leu Lys Leu Leu
1               5                   10                  15

Asp Asn Trp Asp Ser Val Thr Ser Thr Phe Ser Lys Leu Arg Glu Gln

```
                20                  25                  30
Leu Gly Pro Val Thr Gln Glu Phe Trp Asp Asn Leu Glu Lys Glu Thr
        35                  40                  45
Glu Gly Leu Arg Gln Glu Met Ser Lys Asp Leu Glu Glu Val Lys Ala
    50                  55                  60
Lys Val Gln Pro Tyr Leu Asp Asp Phe Gln Lys Lys Trp Gln Glu Glu
65                  70                  75                  80
Met Glu Leu Tyr Arg Gln Lys Val Glu Pro Tyr Leu Asp Asp Phe Gln
                85                  90                  95
Lys Lys Trp Gln Glu Glu Met Glu Leu Tyr Arg Gln Lys Val Glu Pro
                100                 105                 110
Leu Arg Ala Glu Leu Gln Glu Gly Ala Arg Gln Lys Leu His Glu Leu
            115                 120                 125
Gln Glu Lys Leu Ser Pro Leu Gly Glu Glu Met Arg Asp Arg Ala Arg
        130                 135                 140
Ala His Val Asp Ala Leu Arg Thr His Leu Ala Pro Tyr Ser Asp Glu
145                 150                 155                 160
Leu Arg Gln Arg Leu Ala Ala Arg Leu Glu Ala Leu Lys Glu Asn Gly
                165                 170                 175
Gly Ala Arg Leu Ala Glu Tyr His Ala Lys Ala Thr Glu His Leu Ser
                180                 185                 190
Thr Leu Ser Glu Lys Ala Lys Pro Ala Leu Glu Asp Leu Arg Gln Gly
            195                 200                 205
Leu Leu Pro Val Leu Glu Ser Phe Lys Val Ser Phe Leu Ser Ala Leu
        210                 215                 220
Glu Glu Tyr Thr Lys Lys Leu Asn Thr Gln
225                 230

<210> SEQ ID NO 74
<211> LENGTH: 256
<212> TYPE: PRT
<213> ORGANISM: Artificial Sequence
<220> FEATURE:
<223> OTHER INFORMATION: artificial sequence of His-tagged MSP1E2

<400> SEQUENCE: 74

Met Gly His His His His His Ile Glu Gly Arg Leu Lys Leu Leu
1               5                   10                  15
Asp Asn Trp Asp Ser Val Thr Ser Thr Phe Ser Lys Leu Arg Glu Gln
            20                  25                  30
Leu Gly Pro Val Thr Gln Glu Phe Trp Asp Asn Leu Glu Lys Glu Thr
        35                  40                  45
Glu Gly Leu Arg Gln Glu Met Ser Lys Asp Leu Glu Glu Val Lys Ala
    50                  55                  60
Lys Val Gln Pro Tyr Leu Asp Asp Phe Gln Lys Lys Trp Gln Glu Glu
65                  70                  75                  80
Met Glu Leu Tyr Arg Gln Lys Val Glu Pro Tyr Leu Asp Asp Phe Gln
                85                  90                  95
Lys Lys Trp Gln Glu Glu Met Glu Leu Tyr Arg Gln Lys Val Glu Pro
                100                 105                 110
Leu Arg Ala Glu Leu Gln Glu Gly Ala Arg Gln Lys Leu His Glu Leu
            115                 120                 125
Gln Glu Lys Leu Ser Pro Leu Arg Ala Glu Leu Gln Glu Gly Ala Arg
        130                 135                 140
Gln Lys Leu His Glu Leu Gln Glu Lys Leu Ser Pro Leu Gly Glu Glu
```

```
            145                 150                 155                 160
Met Arg Asp Arg Ala Arg Ala His Val Asp Ala Leu Arg Thr His Leu
                165                 170                 175

Ala Pro Tyr Ser Asp Glu Leu Arg Gln Arg Leu Ala Ala Arg Leu Glu
            180                 185                 190

Ala Leu Lys Glu Asn Gly Gly Ala Arg Leu Ala Glu Tyr His Ala Lys
        195                 200                 205

Ala Thr Glu His Leu Ser Thr Leu Ser Glu Lys Ala Lys Pro Ala Leu
    210                 215                 220

Glu Asp Leu Arg Gln Gly Leu Leu Pro Val Leu Glu Ser Phe Lys Val
225                 230                 235                 240

Ser Phe Leu Ser Ala Leu Glu Glu Tyr Thr Lys Lys Leu Asn Thr Gln
                245                 250                 255

<210> SEQ ID NO 75
<211> LENGTH: 278
<212> TYPE: PRT
<213> ORGANISM: Artificial Sequence
<220> FEATURE:
<223> OTHER INFORMATION: artificial sequence of His-tagged MSP1E3

<400> SEQUENCE: 75

Met Gly His His His His His His Ile Glu Gly Arg Leu Lys Leu Leu
1               5                   10                  15

Asp Asn Trp Asp Ser Val Thr Ser Thr Phe Ser Lys Leu Arg Glu Gln
            20                  25                  30

Leu Gly Pro Val Thr Gln Glu Phe Trp Asp Asn Leu Glu Lys Glu Thr
        35                  40                  45

Glu Gly Leu Arg Gln Glu Met Ser Lys Asp Leu Glu Glu Val Lys Ala
    50                  55                  60

Lys Val Gln Pro Tyr Leu Asp Asp Phe Gln Lys Lys Trp Gln Glu Glu
65                  70                  75                  80

Met Glu Leu Tyr Arg Gln Lys Val Glu Pro Tyr Leu Asp Asp Phe Gln
                85                  90                  95

Lys Lys Trp Gln Glu Glu Met Glu Leu Tyr Arg Gln Lys Val Glu Pro
            100                 105                 110

Leu Arg Ala Glu Leu Gln Glu Gly Ala Arg Gln Lys Leu His Glu Leu
        115                 120                 125

Gln Glu Lys Leu Ser Pro Leu Gly Glu Glu Met Arg Asp Arg Ala Arg
    130                 135                 140

Ala His Val Asp Ala Leu Arg Thr His Leu Ala Pro Leu Arg Ala Glu
145                 150                 155                 160

Leu Gln Glu Gly Ala Arg Gln Lys Leu His Glu Leu Gln Glu Lys Leu
                165                 170                 175

Ser Pro Leu Gly Glu Glu Met Arg Asp Arg Ala Arg Ala His Val Asp
            180                 185                 190

Ala Leu Arg Thr His Leu Ala Pro Tyr Ser Asp Glu Leu Arg Gln Arg
        195                 200                 205

Leu Ala Ala Arg Leu Glu Ala Leu Lys Glu Asn Gly Gly Ala Arg Leu
    210                 215                 220

Ala Glu Tyr His Ala Lys Ala Thr Glu His Leu Ser Thr Leu Ser Glu
225                 230                 235                 240

Lys Ala Lys Pro Ala Leu Glu Asp Leu Arg Gln Gly Leu Leu Pro Val
                245                 250                 255

Leu Glu Ser Phe Lys Val Ser Phe Leu Ser Ala Leu Glu Glu Tyr Thr
```

-continued

```
                    260                 265                 270
Lys Lys Leu Asn Thr Gln
        275

<210> SEQ ID NO 76
<211> LENGTH: 223
<212> TYPE: PRT
<213> ORGANISM: Artificial Sequence
<220> FEATURE:
<223> OTHER INFORMATION: artificial sequence of His-tagged MSP1TEV

<400> SEQUENCE: 76

Met Gly His His His His His His Asp Tyr Asp Ile Pro Thr Thr
1               5                   10                  15

Glu Asn Leu Tyr Phe Gln Gly Leu Lys Leu Leu Asp Asn Trp Asp Ser
                20                  25                  30

Val Thr Ser Thr Phe Ser Lys Leu Arg Glu Gln Leu Gly Pro Val Thr
            35                  40                  45

Gln Glu Phe Trp Asp Asn Leu Glu Lys Glu Thr Glu Gly Leu Arg Gln
    50                  55                  60

Glu Met Ser Lys Asp Leu Glu Glu Val Lys Ala Lys Val Gln Pro Tyr
65                  70                  75                  80

Leu Asp Asp Phe Gln Lys Lys Trp Gln Glu Glu Met Glu Leu Tyr Arg
                85                  90                  95

Gln Lys Val Glu Pro Leu Arg Ala Glu Leu Gln Glu Gly Ala Arg Gln
            100                 105                 110

Lys Leu His Glu Leu Gln Glu Lys Leu Ser Pro Leu Gly Glu Glu Met
        115                 120                 125

Arg Asp Arg Ala Arg Ala His Val Asp Ala Leu Arg Thr His Leu Ala
    130                 135                 140

Pro Tyr Ser Asp Glu Leu Arg Gln Arg Leu Ala Ala Arg Leu Glu Ala
145                 150                 155                 160

Leu Lys Glu Asn Gly Gly Ala Arg Leu Ala Glu Tyr His Ala Lys Ala
                165                 170                 175

Thr Glu His Leu Ser Thr Leu Ser Glu Lys Ala Lys Pro Ala Leu Glu
            180                 185                 190

Asp Leu Arg Gln Gly Leu Leu Pro Val Leu Glu Ser Phe Lys Val Ser
        195                 200                 205

Phe Leu Ser Ala Leu Glu Glu Tyr Thr Lys Lys Leu Asn Thr Gln
    210                 215                 220

<210> SEQ ID NO 77
<211> LENGTH: 200
<212> TYPE: PRT
<213> ORGANISM: Artificial Sequence
<220> FEATURE:
<223> OTHER INFORMATION: artificial sequence of MSP1NH

<400> SEQUENCE: 77

Leu Lys Leu Leu Asp Asn Trp Asp Ser Val Thr Ser Thr Phe Ser Lys
1               5                   10                  15

Leu Arg Glu Gln Leu Gly Pro Val Thr Gln Glu Phe Trp Asp Asn Leu
                20                  25                  30

Glu Lys Glu Thr Glu Gly Leu Arg Gln Glu Met Ser Lys Asp Leu Glu
            35                  40                  45

Glu Val Lys Ala Lys Val Gln Pro Tyr Leu Asp Asp Phe Gln Lys Lys
        50                  55                  60
```

```
Trp Gln Glu Glu Met Glu Leu Tyr Arg Gln Lys Val Glu Pro Leu Arg
 65                  70                  75                  80

Ala Glu Leu Gln Glu Gly Ala Arg Gln Lys Leu His Glu Leu Gln Glu
                 85                  90                  95

Lys Leu Ser Pro Leu Gly Glu Glu Met Arg Asp Arg Ala Arg Ala His
            100                 105                 110

Val Asp Ala Leu Arg Thr His Leu Ala Pro Tyr Ser Asp Glu Leu Arg
        115                 120                 125

Gln Arg Leu Ala Ala Arg Leu Glu Ala Leu Lys Glu Asn Gly Gly Ala
    130                 135                 140

Arg Leu Ala Glu Tyr His Ala Lys Ala Thr Glu His Leu Ser Thr Leu
145                 150                 155                 160

Ser Glu Lys Ala Lys Pro Ala Leu Glu Asp Leu Arg Gln Gly Leu Leu
                165                 170                 175

Pro Val Leu Glu Ser Phe Lys Val Ser Phe Leu Ser Ala Leu Glu Glu
            180                 185                 190

Tyr Thr Lys Lys Leu Asn Thr Gln
        195                 200

<210> SEQ ID NO 78
<211> LENGTH: 212
<212> TYPE: PRT
<213> ORGANISM: Artificial Sequence
<220> FEATURE:
<223> OTHER INFORMATION: artificial sequence of His-tagged MSP1T2

<400> SEQUENCE: 78

Met Gly His His His His His His Asp Tyr Asp Ile Pro Thr Thr
  1               5                  10                  15

Glu Asn Leu Tyr Phe Gln Gly Ser Thr Phe Ser Lys Leu Arg Glu Gln
                 20                  25                  30

Leu Gly Pro Val Thr Gln Glu Phe Trp Asp Asn Leu Glu Lys Glu Thr
            35                  40                  45

Glu Gly Leu Arg Gln Glu Met Ser Lys Asp Leu Glu Glu Val Lys Ala
        50                  55                  60

Lys Val Gln Pro Tyr Leu Asp Asp Phe Gln Lys Lys Trp Gln Glu Glu
 65                  70                  75                  80

Met Glu Leu Tyr Arg Gln Lys Val Glu Pro Leu Arg Ala Glu Leu Gln
                 85                  90                  95

Glu Gly Ala Arg Gln Lys Leu His Glu Leu Gln Glu Lys Leu Ser Pro
            100                 105                 110

Leu Gly Glu Glu Met Arg Asp Arg Ala Arg Ala His Val Asp Ala Leu
        115                 120                 125

Arg Thr His Leu Ala Pro Tyr Ser Asp Glu Leu Arg Gln Arg Leu Ala
    130                 135                 140

Ala Arg Leu Glu Ala Leu Lys Glu Asn Gly Gly Ala Arg Leu Ala Glu
145                 150                 155                 160

Tyr His Ala Lys Ala Thr Glu His Leu Ser Thr Leu Ser Glu Lys Ala
                165                 170                 175

Lys Pro Ala Leu Glu Asp Leu Arg Gln Gly Leu Leu Pro Val Leu Glu
            180                 185                 190

Ser Phe Lys Val Ser Phe Leu Ser Ala Leu Glu Glu Tyr Thr Lys Lys
        195                 200                 205

Leu Asn Thr Gln
    210
```

```
<210> SEQ ID NO 79
<211> LENGTH: 189
<212> TYPE: PRT
<213> ORGANISM: Artificial Sequence
<220> FEATURE:
<223> OTHER INFORMATION: artificial sequence of MSP1T2NH

<400> SEQUENCE: 79

Ser Thr Phe Ser Lys Leu Arg Glu Gln Leu Gly Pro Val Thr Gln Glu
1               5                   10                  15

Phe Trp Asp Asn Leu Glu Lys Glu Thr Glu Gly Leu Arg Gln Glu Met
            20                  25                  30

Ser Lys Asp Leu Glu Glu Val Lys Ala Lys Val Gln Pro Tyr Leu Asp
        35                  40                  45

Asp Phe Gln Lys Lys Trp Gln Glu Met Glu Leu Tyr Arg Gln Lys
    50                  55                  60

Val Glu Pro Leu Arg Ala Glu Leu Gln Glu Gly Ala Arg Gln Lys Leu
65                  70                  75                  80

His Glu Leu Gln Glu Lys Leu Ser Pro Leu Gly Glu Glu Met Arg Asp
                85                  90                  95

Arg Ala Arg Ala His Val Asp Ala Leu Arg Thr His Leu Ala Pro Tyr
            100                 105                 110

Ser Asp Glu Leu Arg Gln Arg Leu Ala Ala Arg Leu Glu Ala Leu Lys
        115                 120                 125

Glu Asn Gly Gly Ala Arg Leu Ala Glu Tyr His Ala Lys Ala Thr Glu
    130                 135                 140

His Leu Ser Thr Leu Ser Glu Lys Ala Lys Pro Ala Leu Glu Asp Leu
145                 150                 155                 160

Arg Gln Gly Leu Leu Pro Val Leu Glu Ser Phe Lys Val Ser Phe Leu
                165                 170                 175

Ser Ala Leu Glu Glu Tyr Thr Lys Lys Leu Asn Thr Gln
            180                 185

<210> SEQ ID NO 80
<211> LENGTH: 201
<212> TYPE: PRT
<213> ORGANISM: Artificial Sequence
<220> FEATURE:
<223> OTHER INFORMATION: artificial sequence of MSP1T3

<400> SEQUENCE: 80

Met Gly His His His His His His Asp Tyr Asp Ile Pro Thr Thr
1               5                   10                  15

Glu Asn Leu Tyr Phe Gln Gly Pro Val Thr Gln Glu Phe Trp Asp Asn
            20                  25                  30

Leu Glu Lys Glu Thr Glu Gly Leu Arg Gln Glu Met Ser Lys Asp Leu
        35                  40                  45

Glu Glu Val Lys Ala Lys Val Gln Pro Tyr Leu Asp Asp Phe Gln Lys
    50                  55                  60

Lys Trp Gln Glu Met Glu Leu Tyr Arg Gln Lys Val Glu Pro Leu
65                  70                  75                  80

Arg Ala Glu Leu Gln Glu Gly Ala Arg Gln Lys Leu His Glu Leu Gln
                85                  90                  95

Glu Lys Leu Ser Pro Leu Gly Glu Glu Met Arg Asp Arg Ala Arg Ala
            100                 105                 110

His Val Asp Ala Leu Arg Thr His Leu Ala Pro Tyr Ser Asp Glu Leu
        115                 120                 125
```

Arg Gln Arg Leu Ala Ala Arg Leu Glu Ala Leu Lys Glu Asn Gly Gly
            130                 135                 140

Ala Arg Leu Ala Glu Tyr His Ala Lys Ala Thr Glu His Leu Ser Thr
145                 150                 155                 160

Leu Ser Glu Lys Ala Lys Pro Ala Leu Glu Asp Leu Arg Gln Gly Leu
                165                 170                 175

Leu Pro Val Leu Glu Ser Phe Lys Val Ser Phe Leu Ser Ala Leu Glu
            180                 185                 190

Glu Tyr Thr Lys Lys Leu Asn Thr Gln
        195                 200

<210> SEQ ID NO 81
<211> LENGTH: 168
<212> TYPE: PRT
<213> ORGANISM: Artificial Sequence
<220> FEATURE:
<223> OTHER INFORMATION: artificial sequence of MSP1D4D5

<400> SEQUENCE: 81

Met Gly His His His His His His Ile Glu Gly Arg Leu Lys Leu Leu
1               5                   10                  15

Asp Asn Trp Asp Ser Val Thr Ser Thr Phe Ser Lys Leu Arg Glu Gln
            20                  25                  30

Leu Gly Pro Val Thr Gln Glu Phe Trp Asp Asn Leu Glu Lys Glu Thr
        35                  40                  45

Glu Gly Leu Arg Gln Glu Met Ser Lys Asp Leu Glu Glu Val Lys Ala
    50                  55                  60

Lys Val Gln Pro Leu Gly Glu Glu Met Arg Asp Arg Ala Arg Ala His
65                  70                  75                  80

Val Asp Ala Leu Arg Thr His Leu Ala Pro Tyr Ser Asp Glu Leu Arg
                85                  90                  95

Gln Arg Leu Ala Ala Arg Leu Glu Ala Leu Lys Glu Asn Gly Gly Ala
            100                 105                 110

Arg Leu Ala Glu Tyr His Ala Lys Ala Thr Glu His Leu Ser Thr Leu
        115                 120                 125

Ser Glu Lys Ala Lys Pro Ala Leu Glu Asp Leu Arg Gln Gly Leu Leu
    130                 135                 140

Pro Val Leu Glu Ser Phe Lys Val Ser Phe Leu Ser Ala Leu Glu Glu
145                 150                 155                 160

Tyr Thr Lys Lys Leu Asn Thr Gln
                165

<210> SEQ ID NO 82
<211> LENGTH: 168
<212> TYPE: PRT
<213> ORGANISM: Artificial Sequence
<220> FEATURE:
<223> OTHER INFORMATION: His-tagged MSP1D6D7

<400> SEQUENCE: 82

Met Gly His His His His His His Ile Glu Gly Arg Leu Lys Leu Leu
1               5                   10                  15

Asp Asn Trp Asp Ser Val Thr Ser Thr Phe Ser Lys Leu Arg Glu Gln
            20                  25                  30

Leu Gly Pro Val Thr Gln Glu Phe Trp Asp Asn Leu Glu Lys Glu Thr
        35                  40                  45

Glu Gly Leu Arg Gln Glu Met Ser Lys Asp Leu Glu Glu Val Lys Ala

```
                50                  55                  60
Lys Val Gln Pro Tyr Leu Asp Asp Phe Gln Lys Lys Trp Gln Glu Glu
 65                  70                  75                  80

Met Glu Leu Tyr Arg Gln Lys Val Glu Pro Leu Arg Ala Glu Leu Gln
                 85                  90                  95

Glu Gly Ala Arg Gln Lys Leu His Glu Leu Gln Glu Lys Leu Ser Ala
                100                 105                 110

Arg Leu Ala Glu Tyr His Ala Lys Ala Thr Glu His Leu Ser Thr Leu
                115                 120                 125

Ser Glu Lys Ala Lys Pro Ala Leu Glu Asp Leu Arg Gln Gly Leu Leu
130                 135                 140

Pro Val Leu Glu Ser Phe Lys Val Ser Phe Leu Ser Ala Leu Glu Glu
145                 150                 155                 160

Tyr Thr Lys Lys Leu Asn Thr Gln
                165
```

<210> SEQ ID NO 83
<211> LENGTH: 190
<212> TYPE: PRT
<213> ORGANISM: Artificial Sequence
<220> FEATURE:
<223> OTHER INFORMATION: His-tagged MSP1D3D9

<400> SEQUENCE: 83

```
Met Gly His His His His His His Ile Glu Gly Arg Leu Lys Leu Leu
 1               5                  10                  15

Asp Asn Trp Asp Ser Val Thr Ser Thr Phe Ser Lys Leu Arg Glu Gln
                 20                  25                  30

Leu Gly Pro Val Thr Gln Glu Phe Trp Asp Asn Leu Glu Lys Glu Thr
                 35                  40                  45

Glu Gly Leu Arg Gln Glu Met Ser Pro Tyr Leu Asp Asp Phe Gln Lys
             50                  55                  60

Lys Trp Gln Glu Glu Met Glu Leu Tyr Arg Gln Lys Val Glu Pro Leu
 65                  70                  75                  80

Arg Ala Glu Leu Gln Glu Gly Ala Arg Gln Lys Leu His Glu Leu Gln
                 85                  90                  95

Glu Lys Leu Ser Pro Leu Gly Glu Glu Met Arg Asp Arg Ala Arg Ala
                100                 105                 110

His Val Asp Ala Leu Arg Thr His Leu Ala Pro Tyr Ser Asp Glu Leu
                115                 120                 125

Arg Gln Arg Leu Ala Ala Arg Leu Glu Ala Leu Lys Glu Asn Gly Gly
                130                 135                 140

Ala Arg Leu Ala Glu Tyr His Ala Lys Ala Thr Glu His Leu Ser Thr
145                 150                 155                 160

Leu Ser Glu Lys Ala Lys Pro Val Leu Glu Ser Phe Lys Val Ser Phe
                165                 170                 175

Leu Ser Ala Leu Glu Glu Tyr Thr Lys Lys Leu Asn Thr Gln
                180                 185                 190
```

<210> SEQ ID NO 84
<211> LENGTH: 201
<212> TYPE: PRT
<213> ORGANISM: Artificial Sequence
<220> FEATURE:
<223> OTHER INFORMATION: His-tagged MSP1D10.5

<400> SEQUENCE: 84

-continued

```
Met Gly His His His His His Ile Glu Gly Arg Leu Lys Leu Leu
1               5                   10                  15

Asp Asn Trp Asp Ser Val Thr Ser Thr Phe Ser Lys Leu Arg Glu Gln
            20                  25                  30

Leu Gly Pro Val Thr Gln Glu Phe Trp Asp Asn Leu Glu Lys Glu Thr
            35                  40                  45

Glu Gly Leu Arg Gln Glu Met Ser Lys Asp Leu Glu Glu Val Lys Ala
50                      55                  60

Lys Val Gln Pro Tyr Leu Asp Asp Phe Gln Lys Lys Trp Gln Glu Glu
65                  70                  75                  80

Met Glu Leu Tyr Arg Gln Lys Val Glu Pro Leu Arg Ala Glu Leu Gln
                85                  90                  95

Glu Gly Ala Arg Gln Lys Leu His Glu Leu Gln Glu Lys Leu Ser Pro
            100                 105                 110

Leu Gly Glu Glu Met Arg Asp Arg Ala Arg Ala His Val Asp Ala Leu
            115                 120                 125

Arg Thr His Leu Ala Pro Tyr Ser Asp Glu Leu Arg Gln Arg Leu Ala
    130                 135                 140

Ala Arg Leu Glu Ala Leu Lys Glu Asn Gly Gly Ala Arg Leu Ala Glu
145                 150                 155                 160

Tyr His Ala Lys Ala Thr Glu His Leu Ser Thr Leu Ser Glu Lys Ala
                165                 170                 175

Lys Pro Ala Leu Glu Asp Leu Arg Gln Gly Leu Leu Ser Ala Leu Glu
            180                 185                 190

Glu Tyr Thr Lys Lys Leu Asn Thr Gln
            195                 200
```

<210> SEQ ID NO 85
<211> LENGTH: 190
<212> TYPE: PRT
<213> ORGANISM: Artificial Sequence
<220> FEATURE:
<223> OTHER INFORMATION: His-tagged MSP1D3D10.5

<400> SEQUENCE: 85

```
Met Gly His His His His His Ile Glu Gly Arg Leu Lys Leu Leu
1               5                   10                  15

Asp Asn Trp Asp Ser Val Thr Ser Thr Phe Ser Lys Leu Arg Glu Gln
            20                  25                  30

Leu Gly Pro Val Thr Gln Glu Phe Trp Asp Asn Leu Glu Lys Glu Thr
            35                  40                  45

Glu Gly Leu Arg Gln Glu Met Ser Pro Tyr Leu Asp Asp Phe Gln Lys
50                      55                  60

Lys Trp Gln Glu Glu Met Glu Leu Tyr Arg Gln Lys Val Glu Pro Leu
65                  70                  75                  80

Arg Ala Glu Leu Gln Glu Gly Ala Arg Gln Lys Leu His Glu Leu Gln
                85                  90                  95

Glu Lys Leu Ser Pro Leu Gly Glu Glu Met Arg Asp Arg Ala Arg Ala
            100                 105                 110

His Val Asp Ala Leu Arg Thr His Leu Ala Pro Tyr Ser Asp Glu Leu
            115                 120                 125

Arg Gln Arg Leu Ala Ala Arg Leu Glu Ala Leu Lys Glu Asn Gly Gly
    130                 135                 140

Ala Arg Leu Ala Glu Tyr His Ala Lys Ala Thr Glu His Leu Ser Thr
145                 150                 155                 160
```

Leu Ser Glu Lys Ala Lys Pro Ala Leu Glu Asp Leu Arg Gln Gly Leu
                165                 170                 175

Leu Ser Ala Leu Glu Glu Tyr Thr Lys Lys Leu Asn Thr Gln
            180                 185                 190

<210> SEQ ID NO 86
<211> LENGTH: 381
<212> TYPE: PRT
<213> ORGANISM: Artificial Sequence
<220> FEATURE:
<223> OTHER INFORMATION: His-tagged MSP2D1D1

<400> SEQUENCE: 86

Met Gly His His His His His His Asp Tyr Asp Ile Pro Thr Thr
1               5                   10                  15

Glu Asn Leu Tyr Phe Gln Gly Pro Val Thr Gln Glu Phe Trp Asp Asn
            20                  25                  30

Leu Glu Lys Glu Thr Glu Gly Leu Arg Gln Glu Met Ser Lys Asp Leu
        35                  40                  45

Glu Glu Val Lys Ala Lys Val Gln Pro Tyr Leu Asp Asp Phe Gln Lys
    50                  55                  60

Lys Trp Gln Glu Glu Met Glu Leu Tyr Arg Gln Lys Val Glu Pro Leu
65                  70                  75                  80

Arg Ala Glu Leu Gln Glu Gly Ala Arg Gln Lys Leu His Glu Leu Gln
                85                  90                  95

Glu Lys Leu Ser Pro Leu Gly Glu Glu Met Arg Asp Arg Ala Arg Ala
            100                 105                 110

His Val Asp Ala Leu Arg Thr His Leu Ala Pro Tyr Ser Asp Glu Leu
        115                 120                 125

Arg Gln Arg Leu Ala Ala Arg Leu Glu Ala Leu Lys Glu Asn Gly Gly
    130                 135                 140

Ala Arg Leu Ala Glu Tyr His Ala Lys Ala Thr Glu His Leu Ser Thr
145                 150                 155                 160

Leu Ser Glu Lys Ala Lys Pro Ala Leu Glu Asp Leu Arg Gln Gly Leu
                165                 170                 175

Leu Pro Val Leu Glu Ser Phe Lys Val Ser Phe Leu Ser Ala Leu Glu
            180                 185                 190

Glu Tyr Thr Lys Lys Leu Asn Thr Gln Gly Thr Pro Val Thr Gln Glu
        195                 200                 205

Phe Trp Asp Asn Leu Glu Lys Glu Thr Glu Gly Leu Arg Gln Glu Met
    210                 215                 220

Ser Lys Asp Leu Glu Glu Val Lys Ala Lys Val Gln Pro Tyr Leu Asp
225                 230                 235                 240

Asp Phe Gln Lys Lys Trp Gln Glu Glu Met Glu Leu Tyr Arg Gln Lys
                245                 250                 255

Val Glu Pro Leu Arg Ala Glu Leu Gln Glu Gly Ala Arg Gln Lys Leu
            260                 265                 270

His Glu Leu Gln Glu Lys Leu Ser Pro Leu Gly Glu Glu Met Arg Asp
        275                 280                 285

Arg Ala Arg Ala His Val Asp Ala Leu Arg Thr His Leu Ala Pro Tyr
    290                 295                 300

Ser Asp Glu Leu Arg Gln Arg Leu Ala Ala Arg Leu Glu Ala Leu Lys
305                 310                 315                 320

Glu Asn Gly Gly Ala Arg Leu Ala Glu Tyr His Ala Lys Ala Thr Glu
                325                 330                 335

```
His Leu Ser Thr Leu Ser Glu Lys Ala Lys Pro Ala Leu Glu Asp Leu
            340                 345                 350

Arg Gln Gly Leu Leu Pro Val Leu Glu Ser Phe Lys Val Ser Phe Leu
            355                 360                 365

Ser Ala Leu Glu Glu Tyr Thr Lys Lys Leu Asn Thr Gln
    370                 375                 380

<210> SEQ ID NO 87
<211> LENGTH: 13
<212> TYPE: PRT
<213> ORGANISM: Artificial Sequence
<220> FEATURE:
<223> OTHER INFORMATION: sequence of Helix 10.5

<400> SEQUENCE: 87

Ser Ala Leu Glu Glu Tyr Thr Lys Lys Leu Asn Thr Gln
1               5                   10

<210> SEQ ID NO 88
<211> LENGTH: 49
<212> TYPE: DNA
<213> ORGANISM: Artificial Sequence
<220> FEATURE:
<223> OTHER INFORMATION: nucleotide sequence of Helix 10.5

<400> SEQUENCE: 88
cagttttctg tcagctctgg aagaatatac taaaaagctg aatacccag          49

<210> SEQ ID NO 89
<211> LENGTH: 43
<212> TYPE: PRT
<213> ORGANISM: Artificial Sequence
<220> FEATURE:
<223> OTHER INFORMATION: sequence of GLOB

<400> SEQUENCE: 89

Asp Glu Pro Pro Gln Ser Pro Trp Asp Arg Val Lys Asp Leu Ala Thr
1               5                   10                  15

Val Tyr Val Asp Val Leu Lys Asp Ser Gly Arg Asp Tyr Val Ser Gln
            20                  25                  30

Phe Glu Gly Ser Ala Leu Gly Lys Gln Leu Asn
            35                  40
```

MEMBRANE SCAFFOLD PROTEINS

CROSS REFERENCE TO RELATED APPLICATIONS

This application is a Continuation-in-Part of U.S. patent application Ser. No. 09/990,087, filed Nov. 20, 2001, which claims benefit of U.S. Provisional Application No. 60/252,233, filed Nov. 20, 2000.

ACKNOWLEDGMENT OF FEDERAL RESEARCH SUPPORT

This invention was made, at least in part, with funding from the National Institutes of Health (Grant Nos. R21GM63574, R01GM50007, R01GM31756, R01GM33775, and 5F32GM19024) and the National Science Foundation (Grant No. MCB 01-15068). Accordingly, the United States Government has certain rights in this invention.

BACKGROUND OF THE INVENTION

The field of the present invention encompasses molecular biology and membrane technology. Specifically, the present invention relates to artificial membrane scaffold proteins (MSPs) and methods of using the membrane scaffold proteins to stabilize, disperse and solubilize fully or partially hydrophobic proteins such as tethered, embedded or integral membrane proteins while maintaining the biological activities of those membrane proteins or to stabilize, disperse and solubilize proteins directly from membrane fragments or membranes into a mimic of the native membrane environment.

Several years ago we pursued structural and functional studies of lipids complexed with apolipoproteins and characterized these molecular assemblies by scanning probe microscopy, based on the adsorption of synthetic high density lipoprotein disks (rHDL, apo A-I) onto mica in an oriented manner (Carlson et al., 1997; Bayburt et al., 1998; Bayburt et al., 2000; Carlson et al., 2000). The diameters of the discoidal structures observed are approximately 10 nm with a height of 5.5 nanometers. The 5.5 nm high topology observed is most compatible with a single membrane bilayer epitaxially oriented on the atomically flat mica surface (Carlson et al., 1997).

Purified membrane proteins can be reconstituted into the phospholipid bilayer domain of certain such discoidal structures and studied in solution or subsequently adsorbed on a suitable surface for examination by structural or spectroscopic techniques that take advantage of a surface of oriented protein-bilayer assemblies. In the latter case, the underlying discoidal structures containing the membrane protein are easily recognizable and provide a point of reference for judging the quality of the sample and images.

High-density lipoproteins (HDL) are spherical assemblies of a protein component, termed apo A-I, and various phospholipids. HDL particles play an important role in mammalian cholesterol homeostasis by acting as the primary conduit for reverse cholesterol transport (Fielding and Fielding, 1991). The function of HDL as a cholesterol transporter relies upon the activity of the HDL-associated enzyme lecithin-cholesterol acyl transferase, or LCAT (Glomset, 1968; Jonas, 1991), which mediates the insertion of cholesterol esters into HDL lipoprotein particles. Certain portions of the apo A-I protein are required for the activity of this enzyme (Holvoet et al., 1995). In addition, a part of the apo A-I protein is thought to be in a globular domain at the N-terminus, and to be responsible for interactions with cell surface receptors. One nascent form of HDL particles has been assumed to be that of a discoid based on electron microscopy of stained preparations (Forte et al., 1971). Our laboratory has confirmed this using AFM studies of synthetic forms of rHDL under aqueous conditions. This form, however, is not the predominant form in circulation in vivo. Rather, the apo A-I structure appears to have evolved to stabilize a spherical form.

Two general models for the nascent structure of HDL disks have been proposed. One model has the apo A-I protein surrounding a circular bilayer section as a horizontal band or "belt" composed of a curving segmented alpha helical rod (Wlodawer et al., 1979). The other "picket fence" model has the protein traversing the edges of the bilayer vertically in a series of helical segments (Boguski et al., 1986). Both models are based primarily on indirect experimental evidence, and no three dimensional structure of the entire particle is available to distinguish between them.

The currently accepted model is the belt model, which is consistent with some electron microscopy and neutron scattering data (Wlodawer et al., 1979), where the helices are arranged longitudinally around the edge of the bilayer disks like a "belt" (Segrest et al. 1999). More recent infrared spectroscopy studies using a new method of sample orientation for dichroism measurements are more consistent with the belt model, in contrast to earlier studies (Wald et al., 1990; Koppaka et al., 1999). So far, there is no complete and direct evidence as to which model is correct, even though a low resolution x-ray crystal structure for apo A-I crystallized without lipid (Borhani et al., 1997) has been obtained. The low resolution crystal structure of an N-terminally truncated apo A-I shows a unit cell containing a tetrameric species composed of 4 helical rods which bend into a horseshoe shape and which combine to give a circular aggregate about 125×80×40 Å. It was suggested that a dimeric species in this belt conformation is capable of forming discoidal particles.

The information collected to date concerning the reverse cholesterol transport cycle and the maturation of HDL particles suggests that the apo A-I protein has unique properties that allow it to interact spontaneously with membranes resulting in the formation of lipoprotein particles. Initial apo A-I lipid binding events have been proposed (Rogers et al., 1998), but the mechanism for conversion of bilayer-associated forms to discoidal particles remains unclear. The available evidence suggests that the energy of stabilization of lipid-free apo A-I is fairly low and that there is an equilibrium between two conformers (Atkinson and Small, 1986; Rogers et al., 1998). One conformer may be a long helical rod, and the other may be a helical "hairpin" structure about half as long. It has been suggested that the low stabilization energy and conformational plasticity allow apo A-I to structurally reorganize when it encounters a lipid membrane, thus facilitating the structural changes that would have to take place in both the membrane and the protein to produce discreet lipoprotein particles (Rogers et al., 1998). Once these particles are formed, apo A-I may still undergo specific conformational changes that contribute to the dynamic functionality of the lipoprotein particles and interaction with enzymes and receptors. All of these interactions and changes take place at the protein-lipid interface and in specific topologies providing surface accessibility of critical residues. Thus, there is little reason to believe that apo A-I itself would be ideal for generating a stable, nanometer size phospholipid bilayer of controlled dimension. There is no prior evidence that any lipoprotein would have the desired property of the direct extraction and solubilization of membrane proteins directly from a crude membrane or membrane fragment preparation, as disclosed herein.

Different types of lipid aggregates are used for reconstitution and study of purified membrane proteins; these include membrane dispersions, detergent micelles and liposomes (FIG. 1). Purified systems for biochemical and physical study require stability, which is not always inherent in or is limiting in these systems. Liposomes are closed spherical bilayer shells containing an aqueous interior. Reconstitution into liposomes by detergent dialysis or other methods typically results in random orientation of the protein with respect to outer and lumenal spaces. Since ligands or protein targets are usually hydrophilic or charged, they cannot pass through the liposomal bilayer as depicted in FIG. 1, although this may be advantageous in some instances. Since both sides of the liposomal bilayer are not accessible to bulk solvent, coupling effects between domains on opposite sides of the bilayer are difficult to study. Liposomes are also prone to aggregation and fusion and are usually unstable for long periods or under certain physical manipulations, such as stopped flow or vigorous mixing. The size of liposomes obtained by extruding through defined cylindrical pore sizes polydisperse in size distribution rather than exhibiting a uniform diameter.

Liposomes also may present difficulties due to light scattering, and aggregation of membrane proteins present in the bilayer and thermodynamic instability (Angrand et al., 1997; Savelli et al., 2000). The surface area of a liposome is relatively large ($10^5$ to $10^8$ Å$^2$). To obtain liposomes with single membrane proteins incorporated requires a large lipid to protein molar ratio. Detergent micelles allow solubilization of membrane proteins by interaction with the membrane-embedded portion of the protein and are easy to use. Detergent micelles are dynamic and undergo structural fluctuations that promote subunit dissociation and often present difficulty in the ability to handle proteins in dilute solutions. An excess of detergent micelles, however, is necessary to maintain the protein in a non-aggregated and soluble state. Detergents can also be denaturing and often do not maintain the properties found in a phospholipid bilayer system. Specific phospholipid species are often necessary to support and modulate protein structure and function (Tocanne et al., 1994). Thus, the structure, function, and stability of detergent solubilized membrane proteins may be called into question. Since an excess of detergent micelles is needed, protein complexes can dissociate depending on protein concentration and the detergent protein ratio. By contrast, the MSP nanostructures of the present invention are more robust structurally, having a phospholipid bilayer mimetic domain of discrete size and composition and greater stability and smaller surface area than unilamellar liposomes. The disk structures allow access to both sides of the bilayer like detergents, and also provide a bilayer structure like that of liposomes.

There is a long felt need in the art for stable, defined compositions for the dispersion of membrane proteins and other hydrophobic or partially hydrophobic proteins, such that the native activities and properties of those proteins are preserved.

SUMMARY OF THE INVENTION

Membrane Scaffold Proteins (MSPs) as used herein are artificial amphiphilic proteins which self-assemble with phospholipids and phospholipid mixtures into nanometer size membrane bilayers. A subset of these nanometer size assemblies are discoidal in shape, and are referred to as Nanodisc structures. These "nanoscale" particles can be from about 5 to about 500 nm, about 5 to about 100 nm or about 5 to about 20 nm in diameter. These structures comprising phospholipid and MSP preserve the overall bilayer structure of normal membranes but provide a system which is both soluble in solution and which can be assembled or affixed to a variety of surfaces. The amino acid sequences of specifically exemplified MSPs are given in SEQ ID NO:6, SEQ ID NO:9, SEQ ID NO:17, SEQ ID NO:19, SEQ ID NO:23, SEQ ID NO:29, SEQ ID NO:43, SEQ ID NO:44, SEQ ID NO:45 and SEQ ID NOs:73–86.

The present invention further provides the use of the nanometer scale phospholipid bilayer structures or Nanodiscs formed using the MSPs of the present invention for the incorporation of additional hydrophobic or partially hydrophobic protein molecules. Those additional proteins can be solubilized, for example, with the use of detergent, and the solubilized proteins can be added to a solution of MSP, with or without phospholipid(s), and the nanoscale particles self-assemble so that the MSPs and the additional "target" proteins are incorporated into a stable and soluble particle. Subsequently, any detergent can be removed by dialysis or treatment with such agents as ion exchange resins or macroporous polymeric adsorbent beads, e.g., Biobeads made of styrene divinylbenzene. Phospholipids which can be used in the Nanodisc assembly methods of the present invention include, without limitation, PC, phosphatidyl choline; PE, phosphatidyl ethanolamine, PI, phosphatidyl inositol; DPPC, dipalmitoyl-phosphatidylcholine; DMPC, dimyristoyl phosphatidyl choline; POPC, 1-palmitoyl-2-oleoyl-phosphatidyl choline; DHPC, dihexanoyl phosphatidyl choline, dipalmitoyl phosphatidyl ethanolamine, dipalmitoyl phosphatidyl inositol; dimyristoyl phosphatidyl ethanolamine; dimyristoyl phosphatidyl inositol; dihexanoyl phosphatidyl ethanolamine; dihexanoyl phosphatidyl inositol; 1-palmitoyl-2-oleoyl-phosphatidyl ethanolamine; 1-palmitoyl-2-oleoyl-phosphatidyl inositol; among others. Generally, the phospholipid has two saturated fatty acids of from 6 to 20 carbon atoms with a commonly used head group exemplified by, but not limited to, phosphatidyl choline, phosphatidyl ethanolamine and phosphatidyl serine. Desirably the molar ratio of MSP's to total membrane protein is that which produces about 100 to about 200 phospholipid molecules in each discoidal structure. Those proteins, found in nature or associated with the various membrane structures of a living organism, are solubilized in the MSP supported nanobilayer or Nanodisc, and the native structure and activity of the target protein are preserved in these MSP-supported structures. Besides purified or solubilized hydrophobic or partially hydrophobic proteins, hydrophobic or partially hydrophobic proteins bound to or within membranes or membrane fragments or disrupted membranes can be assembled with the MSPs of the present invention, without the need for pre-purification of the target protein.

The MSP supported bilayers or Nanodiscs can be used in solutions or applied to a number of surfaces, such that the native structure and ligand binding, antigenic determinants and/or enzymatic activities of the natural protein incorporated in the MSP supported structure are maintained. As specifically exemplified, the MSP supported structures are affixed to a gold surface, e.g., for use in surface plasmon resonance technologies, to a multiwell plate or to solid surfaces including but not limited to beads, magnetic particles, chromatography matrix materials and others. Where a polyhistidine sequence (His tag) is retained as part of the MSPs, the Nanodiscs can be bound to a NTA-coated surface, for example.

The present invention further relates to methods for the incorporation of membrane-associated proteins into nanoscale lipid bilayers or Nanodiscs comprising at least one MSP of the present invention. Membrane proteins (tethered, embedded or integral) can be used in the methods of the present invention. These proteins can be incorporated into nanoscale particles with MSPs from solubilized intact membrane preparations, intact cells (native or recombinant) or from disrupted membranes or membrane fragments, without prepurification or prefractionation of the membrane proteins. Tethered membrane proteins can be exemplified by human tissue factor, as well as cytochrome P450 reductases from various sources. Examples of embedded membrane proteins include, without limitation, the general class of membrane associated cytochromes P450, for example, cytochrome P450 2B4 from rabbit liver microsomes, cytochrome P450 3A4 from human liver microsomes and cytochrome P450 6B1 from insect microsomes. The integral membrane proteins are exemplified by the general class of 7-helix transmembrane proteins, including, but not limited to, bacteriorhodopsin from *Halobacterium halobium*, the 5-hydroxy tryptamine 1A G-protein coupled receptor from *Homo sapiens* and other G-protein coupled protein receptors from human, plant, animal or other sources. Members of each type of membrane protein have been successfully incorporated into the nanoscale structures using the MSPs and methods of the present invention. In particular, cell surface receptors, and especially G-protein coupled receptors, can be incorporated into nanobilayer bilayer structures formed with the membrane scaffold proteins (MSPs) of the present invention.

The present invention further provides materials and methods using genetically engineered MSPs which increase the stability and monodispersity of the self-assembled nanoparticles. G-protein coupled receptors (GPCRs) are an important and diverse class of pharmaceutical targets in mammalian cellular membranes where they function as signal transducing elements, bind several classes of bioactive ligands and transmit information to the intracellular machinery. The artificial MSPs of the present invention stabilize and solubilize the membrane-associated form of GPCRs to allow purification and manipulation in solution or on a solid support for use in flow cytometry, high throughput screening applications, on surfaces for surface-plasmon biosensor and scanning-probe techniques, as well as other analytical applications. The methods for Nanodisc production of the present invention can be used to facilitate purification of naturally produced or recombinant membrane proteins in stable, biologically active and soluble form.

We developed Nanodiscs for use in structural, biochemical and pharmaceutical techniques by engineering the scaffold protein (MSP) for greater stability, size homogeneity through various size classes and useful functionalities in the resultant nanoscale lipoprotein particle. These particles can include tags for purification, binding to surfaces and physical manipulation of disks such as in hydrogels or on a gold biosensor surface, and they can serve as robust entities for rapid and reproducible assays and NMR investigations and crystallization. The nanoparticles and membrane protein scaffolds are useful in biotechnology, the pharmaceutical industry as well as in basic research. In addition, the structural and functional principles uncovered through our discovery and the related techniques facilitate understanding the interactions of proteins with lipid bilayers at the molecular level.

BRIEF DESCRIPTION OF THE DRAWINGS

FIG. 2 shows the wheel structure of an alpha helix, with the placement of hydrophobic and hydrophilic amino acid side chains that give the helix its amphipathic character.

FIG. 4A: MSP1 showing positions of half-repeats. Half-repeat 1 is disordered based on molecular dynamics simulation (Phillips, 1997). FIG. 4B: Hinge domain movement. FIG. 4C: Removal of half-repeats. FIG. 4D: Hinge domain replacement with helices 3 and 4. FIG. 4E: MSP2, with a tandem duplication of the sequence of MSP1. FIG. 4F: Removal of half-repeat 1 to make MSP1Δ1. FIG. 4G: Tandem repeat of MSP1Δ1 to form MSP2Δ1.

FIG. 7A: Disk-associated receptor and ligand-induced assembly of receptor-target complex on gold. FIG. 7B: Disk-associated receptor in gel matrix.

FIGS. 16A–16B show the results of size exclusion chromatography of Nanodiscs made using MSP1 and containing a heterologously expressed cytochrome P450, CYP6B1. The target protein is incorporated into the Nanodisc through the simple self-assembly process described in the text. FIG. 16A: Chromatogram showing the size separation of the reconstituted particles (Superdex™ 200). Dotted line shows size separation of a membrane sample in the absence of MSP showing the presence of high molecular weight non-specific and non-functional aggregates. FIG. 16B: Re-chromatogram of the CYP6B 1 containing fraction demonstrating the homogeneity of the self-assembled CYP6B1-bilayer structure.

FIG. 17 shows the preservation of phospholipid content of starting membrane preparation in the resulting soluble Nanodisc bilayers. Vertical bars represent phospholipid type determined from three replicate samples of starting membranes or self-assembled Nanodiscs. PC: phosphatidylcholine, PE: phosphatidylethanolamine, PI: phosphatidylinositol.

DETAILED DESCRIPTION OF THE INVENTION

Abbreviations used in this application include A, Ala, Alanine; M, Met, Methionine; C, Cys, Cysteine; N, Asn, Asparagine; D, Asp, Aspartic Acid; P, Pro, Proline; E, Glu, Glutamic Acid; Q, Gln, Glutamine; F, Phe, Phenylalanine; R, Arg, Arginine; G, Gly, Glycine; S, Ser, Serine; H, His, Histidine; T, Thr, Threonine; I, Ile, Isoleucine; V, Val, Valine; K, Lys, Lysine; W, Try, Tryptophan; L, Leu, Leucine; Y, Tyr, Tyrosine; MSP, membrane scaffold protein; DPPC, dipalmitoyl phosphatidylcholine; PC, phosphatidylcholine; PS, phosphatidyl serine; BR, bacteriorhodopsin; apo A-I, apolipoprotein A-I; GABA, gamma aminobutyric acid; PACAP, pituitary adenylate cyclase-activating polypeptide.

The simplest single-celled organisms are composed of central regions filled with an aqueous material and a variety of soluble small molecules and macromolecules. Enclosing this region is a membrane which is composed of phospholipids arranged in a bilayer structure. In more complex living cells, there are internal compartments and structures that are also enclosed by membranes. There are numerous protein molecules embedded or associated within these membrane structures, and these so-called membrane proteins are often the most important for determining cell functions including communication and processing of information and energy. The largest problem in studying membrane proteins is that the inside of the phospholipid bilayer is hydrophobic and the embedded or anchored part of the membrane protein is itself also hydrophobic. In isolating these membrane proteins from their native membrane environments, it is very difficult to prevent them from forming aggregates, which may be inactive or insoluble in the aqueous environments commonly used for biochemical investigations. The present invention provides ways to generate a soluble nanoparticle that provides a native-like phospholipid bilayer into which hydrophobic proteins of interest (target proteins) can be incorporated to maintain the target protein as a soluble and monodisperse entity. This is accomplished by incorporating hydrophobic proteins such as membrane proteins into nanometer scale structures using the MSPs as described herein.

Membrane Scaffold Proteins (MSPs) as used herein may be artificial (do not occur in nature) amphiphilic proteins which self-assemble phospholipids and phospholipid mixtures into nanometer size membrane bilayers. A subset of these nanometer size assemblies are discoidal in shape, and are referred to as Nanodiscs or Nanodisc structures. These structures preserve the overall bilayer structure of normal membranes but provide a system which is both soluble in solution and can be assembled or affixed to a variety of surfaces.

As used herein, amphiphilic and amphipathic are used synonymously in reference to membrane scaffold proteins. An amphiphilic protein or an amphiphilic helical region of a protein is one which has both hydrophobic and hydrophilic regions.

Figure 1:
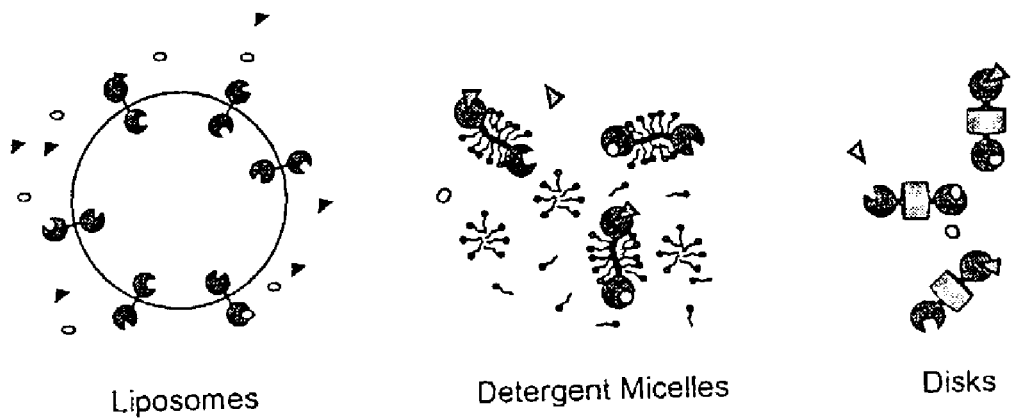
FIG. 1 schematically illustrates different types of lipid aggregates incorporating a membrane protein. Small circles and triangles represent ligand for intracellular and extracellular domains of the receptor proteins, respectively.
Figure 3:
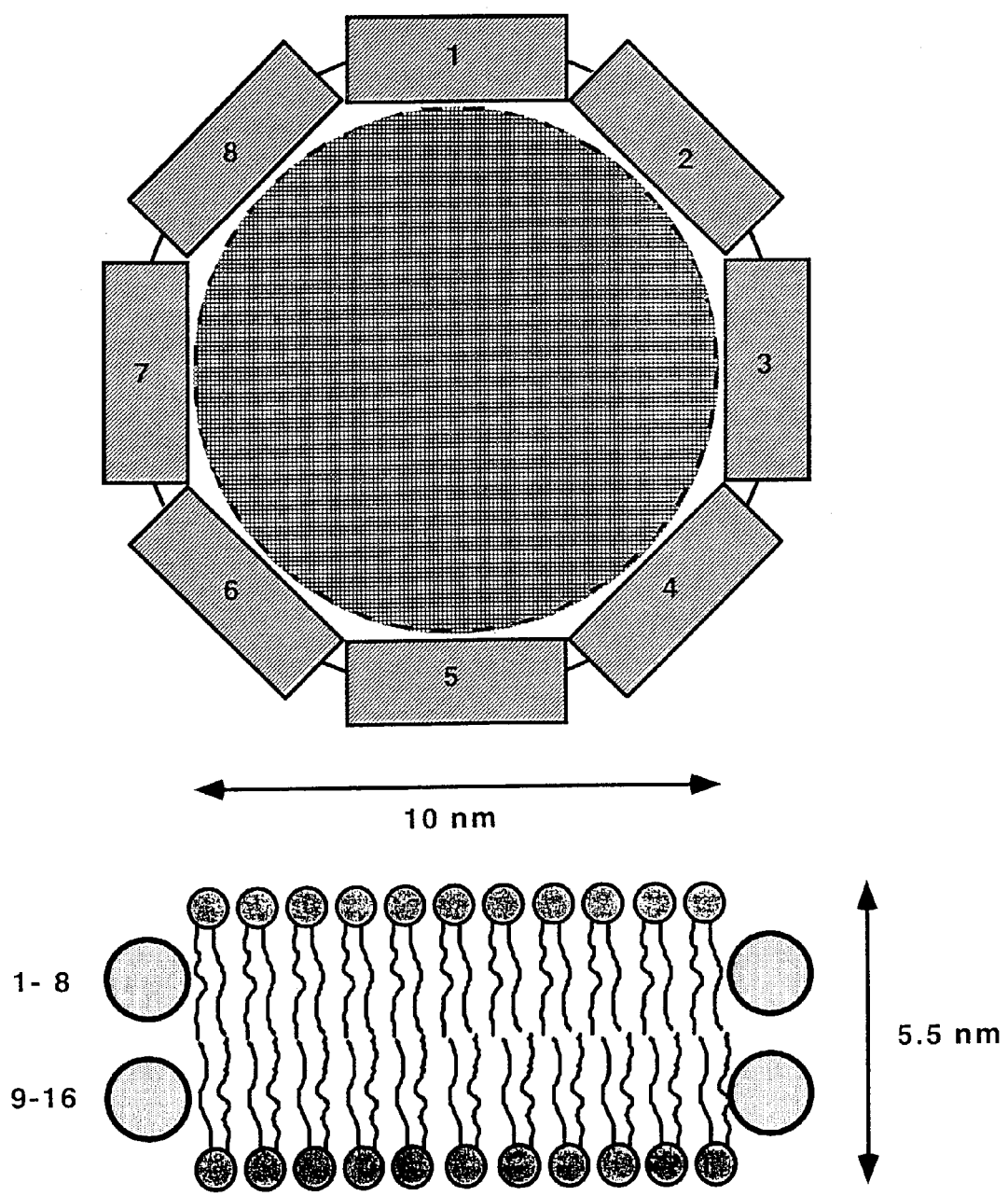
FIG. 3 is a schematic of a "belt" model of an MSP supported bilayer. The rectangles represent single helices with a diameter of about 1.5 nm and a helix length of about 3.9 nm.

The MSPs of the present invention must be amphipathic, with one part of its structure more or less hydrophilic and facing the aqueous solvent and another part more or less hydrophobic and facing the center of the hydrophobic bilayer that is to be stabilized. Examination of the basic biochemical literature reveals two candidate protein structures that can have this required amphipathic character: the helix and the pleated sheet. We designed the MSPs described herein to have a helix as the fundamental amphipathic building block. Each MSP has an amino acid sequence which forms amphipathic helices with more hydrophobic residues (such as A, C, F, G, I, L, M, V, W or Y) predominantly on one face of the helix and more polar or charged residues (such as D, E, N, Q, S, T, H, K or R) on the other face of the helix. See FIG. 2 for a schematic representation. In addition, the helical structure is punctuated with residues such as proline (P) or glycine (G) periodically, which can introduce flexibility into the overall structure by interrupting the general topology of the helix. In one embodiment, these punctuations occur about every 20–25 amino acids to form "kinks" or to initiate turns to facilitate the "wrapping" of the MSP around the edge of a discoidal phospholipid bilayer. See FIG. 2, which depicts a generalized linear amino acid sequence and a helical wheel diagram showing the placement of predominantly hydrophobic amino acids on one face of the helix. In order to generate smaller belts around the bilayer structure, these punctuations may be introduced more frequently. The exact amino acid sequence can vary in the positioning and number of the hydrophobic amino acids within the designed linear sequence. Simple models in which either the helical axis is parallel or perpendicular to the normal of the Nanodisc bilayer can be generated. To generate a disk with a diameter of roughly 10 nm, an MSP comprises about 12 to about 20 or more repeating units having this generalized amphipathic sequence. Preferably, this protein would be composed of amphipathic alpha helices each with a length of between 14 and 25 amino acids, punctuated in the linear sequence by a residue unfavorable for helix formation, such as proline or glycine or a sequence from about 1 to 5 amino acids which does not favor helix formation, which form small helical building blocks that stabilize the hydrophobic core of the phospholipid bilayer. These small helical segments are linked together with from 0 to about 5 amino acid residues. To cover the edge of a 10 nm discoidal particle in either the "belt" model presented, one would need between 10–20 such helices, with 16 being a useful number based on the simple graphic analysis of FIG. 3. We thus built synthetic genes to express proteins containing the desired amphipathic helices. Desirably, the helix contains from about 3 to about 16 amino acids per turn, and the type of helix can be an alpha, pi or 3,10 helix, among others.

In an alternative embodiment, the engineered amphiphilic MSP contain regions of secondary structure such as parallel or antiparallel pleated sheets, with spacer regions of appropriate length to allow association of hydrophobic regions with a target hydrophobic target molecule which is protected from the aqueous milieu, and thus stabilized and solubilized.

Often critical systems controlling cellular function are located in membrane compartments. Many of these membrane protein assemblies represent important pharmaceutical targets that are typically difficult to isolate in soluble and active form because particular phospholipid environments are often essential for maintaining optimal enzymatic turnover or ligand binding activity. Several pharmacologically significant examples indicate specific phospholipid requirements for individual enzymes and receptors, which are perturbed by detergents typically used to solubilize membrane proteins. Examples include the human β-adrenergic receptor that requires neutral lipids for efficient receptor hormone response (Kirolovsky et al., 1985) and the human cytochrome P450 monooxygenase (P450) superfamily that requires several phospholipid types for efficient drug metabolism (Imaoka et al., 1992). An inability to faithfully reconstitute the lipid requirements of detergent solubilized protein in purified systems can, and often does, affect the measured activity of these enzymes. One of the most widely used alternatives for characterization of these native proteins involves the sub-fractionation of natural cellular membranes and incorporation into micron-sized liposomes. However, liposomes are compromised by thermodynamic instability, size heterogeneity and sequestration of target membrane proteins on the solvent-inaccessible side of the bilayer (Angrand et al., 1997; Savelli et al., 2000). Other convenient methods for obtaining large quantities of soluble functional membrane proteins assembled in phospholipid bilayers have not been available and, as a consequence, our molecular understanding of the numerous protein complexes functioning within cell membranes has been hindered. In this application, we report a rapid method for compartmentalizing heterologously-expressed or native membrane proteins into stable, soluble nanometer scale bilayer structures are characterized by sufficient target stability and sufficient robustness to survive operation in high-throughput analyses.

The MSPs of the present invention can be used to solubilize tethered, embedded or integral membrane proteins in nanoscale structures. Tethered membrane proteins are composed mostly of a relatively soluble globular domain external to the bilayer and a relatively simple (e.g., a single membrane spanning domain) which anchors this domain to the membrane bilayer. The globular domain, in nature, can be extracellular or cytoplasmic in orientation. Embedded membrane proteins, as defined herein, are those which include a membrane anchoring segment of the polypeptide, but which also have groupings of hydrophobic amino acids on the surface of the protein, which hydrophobic domains are embedded within the membrane bilayer. Integral membrane proteins have predominant and critical regions of structure located within the membrane bilayer.

An especially valuable advantage of the MSP-containing nanoparticles of the present invention as a means to solubilize hydrophobic or partially hydrophobic "target" proteins is that the protein incorporated into the nanoparticle has a naturalistic presentation. Native target protein structure is maintained, the native target protein-membrane interaction and topology are preserved, the target protein is maintained in a native-like environment, thereby increasing the stability of the target protein to inactivation and denaturation, and the topology of the target protein is maintained relative to the membrane. The maintenance of target protein topology relative to the membrane is especially important for screening targets for cell-cell or cell-virus interaction, elicitation of antibody binding to extra-membrane regions of the target protein or delivery of the target protein through specific trafficking pathways.

The tethered membrane protein class is exemplified by NADPH-cytochrome P450 reductase (e.g., from rat liver endoplasmic reticulum), cytochrome b5 and human tissue factor. NADPH-Cytochrome P450 reductase is a membrane protein found in the endoplasmic reticulum. It catalyzes pyridine nucleotide dehydration and electron transfer to membrane bound cytochrome P450s. Isozymes of similar structure are found in humans, plants, other mammals, insects etc. Tissue factor (TF), or thromboplastin, is a 30,000 Da type-I tethered membrane protein critical to initiation of the blood coagulation cascade. This membrane-bound protein acts as an activation cofactor for factor VII, the soluble serine protease which carries out the first enzymatic step in blood coagulation. Expression of tissue factor is limited to cells that are not in direct contact with blood plasma, which cells form a "hemostatic envelope." The TF:VII complex must be assembled on a membrane surface to exhibit high activity, and optimal activity is seen only when the membrane contains phospholipids with negatively charged headgroups. Cytochrome b5 is a membrane-anchored (tethered) heme protein having a single membrane anchor domain that penetrates the membrane bilayer. Cytochrome b5 solubilized from its native membrane exists as large aggregates in the absence of detergent and appears as a smear rather than a discrete band on native polyacrylamide gel electrophoresis (PAGE). Formation of Nanodiscs through the self-assembly process using MSPs taught in our invention, wherein cytochrome b5 is added to the preparation of MSP and phospholipid results in incorporation of cytochrome b5 into disk structures. The disk complexes containing cytochrome b5 can be chromatographically separated and purified from undesired aggregated material. The optical absorption properties of the heme chromophore of the purified material show that the heme active site is in a native conformation.

Examples of embedded membrane proteins include, without limitation, cytochrome P450 2B4 from rabbit liver microsomes, cytochrome P450 3A4 from human liver microsomes and cytochrome P450 6B1 from insect microsomes. The cytochromes P450 are a superfamily of enzymes that are found in all forms of life. One role of many mammalian P450s is to detoxify xenobiotics; for instance, human liver P450s detoxify most endogenous and exogenous compounds, and these enzymes determine the mean plasma lifetime of all drugs ingested. One of the most widely studied human liver cytochrome P450s is cytochrome P450 3A4 (CYP 3A4). This membrane bound P450 is the most highly expressed P450 in human liver and is responsible for metabolizing almost 50% of all pharmaceuticals (Guengerich, F. P., *Cytochrome P*450. Cytochrome P450, ed. P. R. Ortiz de Montellano, 1995, New York: Plenum Press. 473–535). In order to demonstrate the utility of Nanodisc technology for the study of the cytochrome P450, we incorporated CYP 3A4 into MSP supported nanobilayer discs. Further evidence from size separation chromatography and PAGE analysis supports the conclusion of incorporation of CYP 3A4 into Nanodiscs.

Cytochrome P450 6B1 (CYP 6B1) is a member of the large cytochrome P450 monooxygenase protein superfamily, and it is another example of an embedded membrane protein. CYP 6B1 has been isolated from *Papilio polyxenes*, the black swallow tail, which feeds exclusively on plants producing furanocoumarins, plant psoralen derivatives that are phototoxic to most organisms. CYP 6B1 catalyzes the detoxification of furanocoumarins by what is believed to be an epoxidation reaction (Ma et al. (1994)).

In order to show a new application of the MSP technology of the present invention, we have demonstrated that membranes or membrane fragments containing their natural repertoire of membrane proteins and lipids can be incorporated into Nanodiscs comprising MSPs. This can be effected directly without pre-purification or solubilization of the membrane protein populations. A particularly important embodiment is the use of this technology in a variety of commonly used heterologous expression systems for membrane proteins. These include, but are not limited to, insect cells, yeast cells, HEK cells, CHO cells and bacterial cells. A specifically exemplified embodiment is the use of the common insect cell-baculovirus expression system which is used widely as a heterologous expression system. We used a commercially available Sf9 insect cell line co-infected such that a microsomal preparation containing over-expressed insect CYP6B1 and an over-expressed insect NADPH cytochrome P450 reductase was produced. Hence, we not only demonstrated that MSP Nanodiscs can be used to incorporate another cytochrome P450 system into soluble monodisperse particles, but also that the source of this P450 could be the whole membranes from the Sf9 cell line that was infected with a cloned CYP6B1 gene. The Nanodiscs generated by the procedure described herein contain the fatty acids and phospholipids contained in the original native membrane starting material, and therefore provide a reliable in vitro environment to assay any membrane-bound enzyme or receptor of interest. Thus, MSP supported Nanodiscs can be produced for use in high-throughput screening ventures such as the identification of ligands for membrane-associated proteins and for the identification of new pharmaceuticals. Additionally, the simple procedure of incorporation into Nanodiscs can be used to generate samples for structure determination using x-ray crystallography or NMR spectroscopy. A particular advantage of the Nanodisc system over alternative methods for membrane protein solubilization is the increase in sensitivity of optical measurements due to a significant decrease in light scattering of the particles. The methods of the present invention can be extended to any other source of membrane fragments containing target proteins of interest, such as any yeast, insect, bacterial or mammalian cell culture system or expression system.

An important utility of the Nanodisc technology of the present invention is in high throughput screening for enzymatic or ligand binding activity. In many such systems, it is advantageous to have more than one target membrane protein incorporated into the Nanodiscs, for example, the electron transfer partner needed for P450 monooxygenase catalysis or the corresponding G-protein incorporated with a G-protein coupled receptor.

In order to demonstrate the utility of the MSP Nanodisc technology in these situations, we successfully incorporated the NADPH cytochrome P450 reductase and a cytochrome P450 6B1 into Nanodiscs. As demonstrated herein, each target membrane protein can be individually incorporated into Nanodiscs using MSPs or they can be incorporated in combinations. The endogenous relative amounts of cytochrome P450 to reductase is about 10–20 P450 molecules per reductase molecule (Feyereisen, R. (1999) Ann. Rev. Entomol. 44, 501–533). To obtain activity of CYP6B1 after reconstitution into disks, an excess amount of reductase be added to the reconstitution mixture.

Integral membrane proteins are exemplified by the 7-helix transmembrane proteins, including, but not limited to, bacteriorhodopsin from *Halobacterium halobium*, the 5-hydroxy tryptamine 1A G-protein coupled receptor from *Homo sapiens* and other G-protein coupled protein receptors. Members of each class of membrane protein have been successfully incorporated into the nanoscale structures using the MSPs and methods of the present invention. In particular, cell surface receptors, and especially G-protein coupled receptors, can be incorporated into nanobilayer bilayer structures formed with MSPs. BR has been incorporated into the MSP Nanodiscs as described herein, and we have also used a commercially available insect cell expression system that provides a membrane fraction hosting the G-protein coupled receptor human for 5-HT-1A (serotonin). The ligand binding activity documented for 5-HT-1A incorporation into Nanodiscs proves that the protein is in the active conformation in the Nanodiscs of the present invention. Subsequent experiments show that the beta-2 adrenergic receptor, the dopamine D2 receptor and the cytokine receptors CXCR4 and CCR5, all of which belong to the 7-transmembrane protein family and G-protein coupled receptor type, are easily incorporated into Nanodiscs by the methods of the present invention.

We created an additional artificial variant MSP (MSP2) by designing a tandem repeat of MSP1 connected by a short linker to create a new molecule. See FIG. 4G and SEQ ID NO:17. Relatively large quantities (tens of milligrams/liter cell culture) of the artificial MSPs of the present invention are produced in a bacterial expression system. Our constructs reduce the number of size classes that can be formed (those corresponding to three MSP1 molecules).

MSPs have been engineered to minimize the variability in the structure of the discoidal phospholipid bilayer entities, provide greater structural stability and increased size homogeneity of the disk structures, and incorporate useful functionalities such as tags for purification and physical manipulation of disks. Disk homogeneity is necessary for efficient incorporation of single membrane proteins or single membrane protein complexes into a single size class of disk. The parent molecule, apo A-I, has functions beyond disk structure stabilization (Forte et al., 1971; Holvoet et al., 1995; Fidge, 1999). These functional regions are unnecessary and often deleterious in the artificial bilayer systems of the present invention.

Secondary structure prediction provides a way of assessing structural features of the scaffold protein. The apo AI structure consists of mostly helix punctuated by proline or glycine residues in the repeat sequences. Eight to nine helices are believed to associate with lipid in the form of disks. The N-terminal "GLOB" region (SEQ ID NO:89) of apo A-I is predicted to be more globular in character. This portion of the molecule has been removed to produce the engineered MSP1. An MSP that produces disk assemblies with high monodispersity is desirable. To ascertain the roles of half repeats and to further characterize and optimize the MSP structure and function, mutagenesis and directed evolution were used to generate variants as described herein below. See Tables 2–21 below.

Hydrophobic or partially hydrophobic receptors incorporated into MSP disks are useful in structural, biochemical and pharmaceutical research. Membrane protein study is currently limited to insoluble membrane dispersions, detergent micelles, and liposomes. Purified systems for biochemical and physical study require stability, which may or may not be obtainable with detergents. Detergent micelles are dynamic and undergo structural fluctuations that promote subunit dissociation and present difficulty in the ability to handle proteins in dilute solution. MSP nanobilayers (Nanodiscs) are more robust structurally, having a phospholipid bilayer mimetic domain of discrete size and composition, and greater stability and smaller surface area than unilamellar liposomes. The particles of the present invention are stable in size, conformation and biological activity for at least a month at 4° C.

Signal transducing elements occur across membranes, while vesicles render one side of membrane in accessible to hydrophilic reagents and effector proteins. A specific embodiment of the present invention uses disks to solubilize and stabilize pharmaceutical targets such as GPCRs, ion channels, receptor kinases, and phosphatases in a naturalistic presentation. We have incorporated proteins with multiple membrane spanning domains into the disks of the present invention, with a focus on GPCRs. We had successfully incorporated the model serpentine membrane protein, bacteriorhodopsin, into Nanodiscs. Bacteriorhodopsin is a model for GPCRs, which are current targets for drug discovery. Currently, over 1000 probable G-protein receptors from various organisms have been cloned and many of the so-called "orphan" receptors await identification of natural ligands. Ligand classes include peptide hormones, eicosanoids, lipids, calcium, nucleotides, and biogenic amines. GPCRs are believed be targets for more than half of currently marketed pharmaceuticals. This structural class of membrane proteins can readily be incorporated into Nanodiscs when contacted with MSPs as pre-solubilized proteins or as membrane-associated proteins. Structural characterization of the reconstituted receptors are performed using chemical analysis, spectroscopy and atomic force microscopy.

The MSPs of the present invention, when formulated into disks, can be used in analyses in surface technology such as biosensor chips for high throughput screening or solid phase assay techniques, including but not limited to multiwell plates made, for example, of polystyrene. Our work on disk scaffolds has also involved surface-associated assemblies.

Figure 7A:
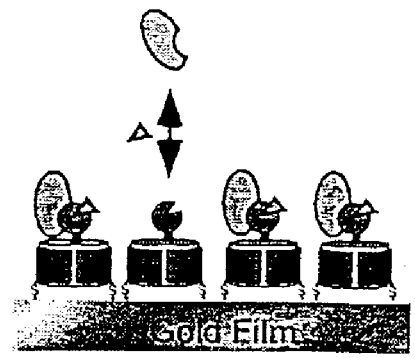
FIGS. 7A–7B show the membrane proteins incorporated into disks and attached to solid supports.

For instance, the SPR biosensor utilizes an approximately 50 nm thick gold film on an optical component to couple surface plasmons to a dielectric component (sample) at the surface of the gold film. MSP stabilized bilayers can be attached to the surface for use as a biomimetic layer containing proteins or other targets of interest by engineering cysteines into the MSP (FIG. 7A). The use of thiols is well known for attaching molecules to gold surfaces. Based on the belt model, cysteines can be placed along the polar side of the amphipathic helix axis, provided that a cysteine residue is not positioned at the helix-helix interface. In cases wherein the MSP is so engineered, multiple cysteine residues can form disulfide-linked dimers (Segrest et al., 1999). An alternative is to introduce cysteines within a flexible N- or C-terminal linker. Such a construct is, in theory, capable of associating either the belt or the picket fence model of disk to a gold surface. Alternatively, thiol lipids can be incorporated within the bilayer domain. In addition to SPR, surface-associated disks on gold can be used in STM and electrochemical studies, for example, such as with membrane associated redox proteins, e.g. cytochrome P450 and its flavoprotein, as well as ion channels.

SPR data can also be obtained from measurements made using a thin film of dielectric such as silicon dioxide applied over the metal film normally used as the substrate in SPR. This variation of the technique has been termed coupled plasmon waveguide resonance (CPWR) (Salamon et al., 1997a). Because silica can be used as the active surface in these plasmon resonance experiments, the process of producing a self-assembled bilayer can be adapted according to the procedures used to produce surfaces on mica or other silicon oxide surfaces. This has the added advantage of making the conditions used for the SPR experiments directly comparable to those used for AFM experiments. The CPWR technique can easily be performed on an SPR instrument by simply adding the silica coating to the metal film slides that are presently used for SPR spectroscopy.

MSPs with available cysteine groups also enable specific labeling with chemically reactive groups or affinity tags for immobilization in gel matrices. Hydrogels with reactive coupling groups are useful for immobilizing proteins for SPR measurements. In a hydrogel configuration, the disk would serve as a carrier for bilayer-embedded membrane proteins in a monodisperse form with both intra- and extracellular domains available for ligand binding. We have already demonstrated that disks containing a His tag bind to a metal chelate matrix. Nanodiscs can also be used in preparing affinity matrices for bioseparation processes and measurements of ligand affinities. The particles produced by the methods of the present invention are useful for drug discovery, structure/function correlation, and structure determination of membrane proteins.

Current limitations to structure determination of membrane proteins are the abilities to produce large amounts of membrane proteins, and to crystallize these proteins. MSPs are useful as carriers for membrane protein stabilization and expression. MSP can serve to solubilize membrane proteins for crystallization in lieu of detergents. Indeed, where the lipid bound form of MSP is structurally stable and rigid, crystallization can be enhanced by introduction of crystal contacts through the MSP. We have demonstrated that MSP1 or MSP2 can be used to solubilize BR from purple membranes in the presence and absence of exogenous lipid. Fusion constructs with membrane protein with an MSP region can be expressed in Escherichia coli using any of a number of art-known vectors to produce a stable and soluble form of the membrane protein that contains a membrane anchor in large quantity. The exciting discovery that MSP solubilizes BR in the absence of added phospholipid allows the use of the artificial MSP to stabilize membrane proteins in the absence of detergents or lipid additives. The (artificial) MSPs disclosed herein can be used in solubilization of other membrane proteins including, but not limited to, cytochrome P450, cytochrome P450 reductase, and the 5-HT-1A receptor, as well as other membrane-associated receptor proteins and enzymes.

Cytochrome proteins and reductases can be derived from plant, insect, mammalian, avian or other sources. Specific examples include, insect cytochrome P450 reductase and cytochrome P450 CYP6B1 and plant cytochrome P450 CYP7B12, CYP7B13, CYP73A5, CYP86A1, CYP86A2, CYP86A4, CYP86A7 or CYP86A8. "Derived from" can mean that the target protein is present in a natural (native) membrane when contacted with MSP to produce Nanodiscs, or the target protein can be isolated, purified or presolublized, or the target protein can be associated with the membranes of cells in which it is recombinantly produced.

Other exemplary proteins include mammalian, especially human, CCR5 and CXCR4 chemokine receptors. These were incorporated into Nanodiscs by contacting membranes containing native or recombinant protein. The native protein conformation is maintained, as evidence by the reaction of the CCR5-containing and CXCR4-containing Nanodiscs with CCR5- and CXCR4-specific antibodies.

Figure 4A:
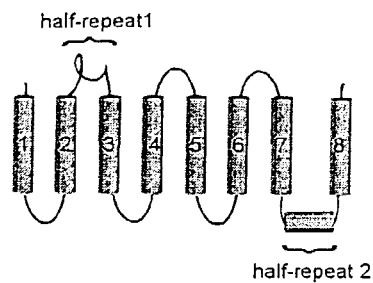
FIGS. 4A–4G illustrate various engineered MSP structures, shown with picket fence topology and helical assignments based on sequence analysis.
Figure 4B:
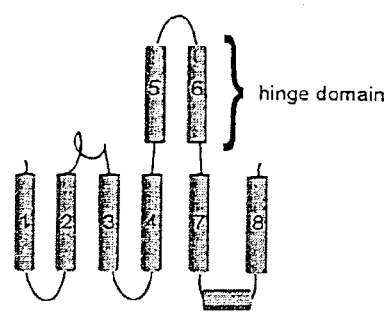
Figure 4C:
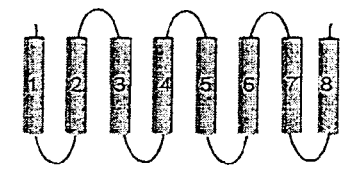
Figure 4D:
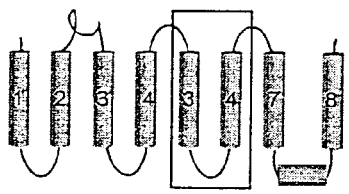
Figure 4E:
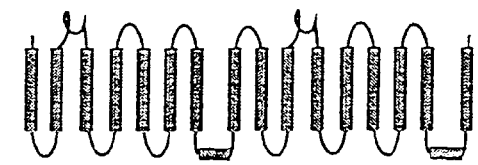
Figure 4F:
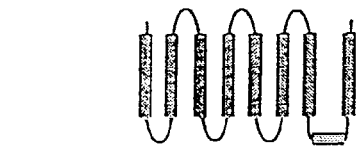
Figure 4G:
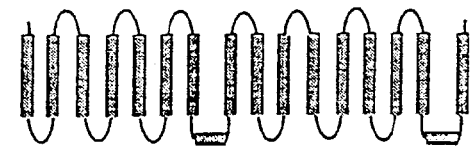
Figure 5A:
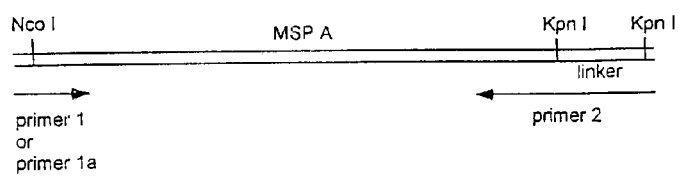
FIGS. 5A–5B diagrammatically illustrate the PCR strategy used to amplify artificial MSPs.
Figure 5B:
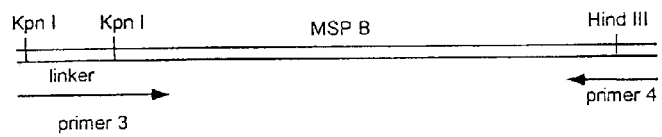

One important goal in utilizing a membrane scaffold protein (MSP) to provide membrane proteins in general, and G-protein Coupled Receptors (GPCRs) in particular, with a suitable environment for homogeneous biochemical assay or crystallization is to have homogeneous preparations of particles. The engineered membrane scaffold proteins we have described, including, but not limited to, truncated human apo-AI (MSP1) where the amino terminal soluble domain has been removed, deletion or insertion mutants where one or more protein segments are removed or inserted, and any of the above materials where a histidine tag is incorporated, primarily form 8–10 nm particles when self-assembled with phospholipids in solution. However, upon assembly with non-optimal stoichiometry of MSP and phospholipid, particles of other sizes may be present. While standard size separation chromatography can be used to purify a single size class of particle, it is preferable to minimize the size distribution of the initial reconstitution mixture of target protein, MSP and phospholipid. Engineered Nanodiscs of various sizes can be formed by appropriate choice of the length of the membrane scaffold protein. The 8–10 nm particle is nominally composed of two MSP proteins. We constructed a membrane scaffold protein where two of the truncated apo AI derived proteins (termed MSP1) are genetically liked to form a scaffold protein composed of a single polypeptide chain. This is schematically illustrated in FIG. 4G.

GPCRs which can be solubilized in nanoscale phospholipid bilayers include the Class A (Rhodopsin-like) GPCRs which bind amines, peptides, hormone proteins, rhodopsin, olfactory prostanoid, nucleotide-like compounds, cannabinoids, platelet activating factor, gonadotropin-releasing hormone, thyrotropin-releasing hormone and secretagogue, melatonin and lysosphingolipid and lysophosphatidic acid (LPA), among other compounds. GPCRs with amine ligands include, without limitation, acetylcholine or muscarinic, adrenoceptors, dopamine, histamine, serotonin or octopamine receptors; peptide ligands include but are not limited to angiotensin, bombesin, bradykinin, anaphylatoxin, Fmet-leu-phe, interleukin-8, chemokine, cholecystokinin, endothelin, melanocortin, neuropeptide Y, neurotensin, opioid, somatostatin, tachykinin, thrombin vasopressin-like, galanin, proteinase activated, orexin and neuropeptide FF, adrenomedullin (G10D), GPR37/endothelin B-like, chemokine receptor-like and neuromedin U.

Ligands of other specific GPCRs include hormone protein, rhodopsin, olfactory, prostanoid, nucleotide-like (adenosine, purinoceptors), cannabinoid, platelet activating factor, gonadotropin-releasing hormone, thyrotropin-releasing hormone and secretagogue, melatonin and lysosphingolipid and LPA, among others. Class B secretin-like GPCRs include, without limitation, those which bind calcitonin, corticotropin releasing factor, gastric inhibitory peptide, glucagon, growth hormone-releasing hormone, parathyroid hormone, pituitary adenylate cyclase activating polypeptide (PACAP), secretin, vasoactive intestinal polypeptide, diuretic hormone, EMR1 and latrophilin. Class C metabotropic glutamate receptors include those which bind metabotropic glutamate, extracellular calcium-sensing receptors or GABA-B receptors, among others. "Orphan" receptors whose ligands are not yet known are also potential targets of assays of the present invention.

In the assays of the present invention which demonstrate binding of a particular ligand or which are used to identify inhibitors or competitors of ligand binding to an MSP-supported GPCR, a variety of labels can be incorporated within the ligand molecule (such as radioactive isotope, e.g., $^3$H, $^{14}$C, $^{35}$S, $^{32}$P, $^{125}$I, $^{131}$I, fluorescent compounds, luminescent compounds, etc.) can be attached to the ligand molecule provided that binding to the cognate receptor is not significantly reduced due to the label.

The necessary properties of the linker sequence between fused MSPs are flexibility and solubility so that the fused proteins assemble into particles in a manner similar to two separate MSP molecules. Linker sequences consisting of repeats of Gly-Gly-Gly-Ser/Thr- (SEQ ID NO:46) have these properties. It is also desirable to minimize the length of the linker. We constructed a fusion with the minimal linker -GT-, which corresponds to the consensus DNA restriction site for Kpn I, as described herein below. The Kpn I site provides an easy way of inserting any desired linker sequence by restriction with Kpn I and insertion of double-stranded synthetic DNA encoding any desired linker (Robinson et al. 1998). We have also made a fusion construct with the linker sequence-GTGGGSGGGT-(SEQ ID NO:15). The MSP2 with the minimal linker, however, assembles into particles very similar to particles containing two MSP1 proteins, but which are more stable than those comprised of two MSP1 proteins.

The complete amino acid and nucleic acid sequences for the MSP2 scaffold protein is shown in Tables 7 and 8; see also SEQ ID NO:16 and SEQ ID NO:17. The MSP2 fusion protein was expressed in *E. coli* and purified to homogeneity using basically the same procedure as described for the single MSPs. The MSP2 protein serves as an effective scaffold protein, self-assembling with phospholipid upon removal of solubilizing detergent. At a lipid/dimer ratio of 200 corresponding to nominally 10 nm particles, there is the much greater monodispersivity afforded by the MSP2 protein. Importantly, the overall stability of the disks, as monitored by chemically induced unfolding and exposure of tryptophan residues to solvent, is not altered by the fusion of the monomeric membrane scaffold proteins.

An important technique used in the characterization of disk structures and associated proteins is scanning probe microscopy (SPM). SPM is an umbrella term for any microscope that utilizes the scanning principles first pioneered in the scanning tunneling microscope (STM), but these microscopes can vary so greatly they are best discussed in terms of their guiding central principle. The technology has been used in the analysis of biological membranes and their associated proteins, bilayer structures and incorporated membrane proteins surfaces. SPM combines independent mobility in all three spatial directions (scanning) with a detection system capable of detecting some characteristic of the surface (probing). The various surface characteristics that can be probed (conductivity, surface forces, compressibility, capacitance, magnetic, fluorescence emission) demonstrate the wealth of information that can be obtained. The excellent z-axis sensitivity of atomic force microscopy makes the presence of proteins binding to an rHDL monolayer or in Nanodiscs easily detectable (Bayburt et al., 1998). Precise height measurements are possible with AFM, and membrane protein height measurements obtained by modulating the force of the AFM probe on various Nanodisc assemblies (Bayburt et al., 2000). The surface association of disks formed from MSPs allow direct investigation of the biophysical properties of single membrane proteins incorporated into phospholipid bilayers on surfaces by SPM. The ability to attach disks to atomically flat conductive surfaces (such as gold or silica) is necessary for scanning tunneling microscopy (STM). Without wishing to be bound by theory, it is believed that tunneling through a redox-active system can be used to probe the functional state of an enzyme (Friis et al., 1999; Mukhopadhyay et al., 2000). These two techniques provide complementary data and can be used in concert to study events occurring at the bilayer/solution interface. The ability to place disks on a gold surface also allows the use of surface plasmon resonance (SPR). Insertion of membrane proteins into such artificial lipid bilayers, or their interaction with surface-associated proteins can be detected and quantified by SPR.

Measurements of disk stabilities and determination of size dispersion among classes are necessary to evaluate the constructs and Nanodiscs. Gel filtration and native gel electrophoresis are used to separate and quantitate sizes of particles. Spectroscopy is used to quantitate secondary structure (CD) and lipid association (fluorescence) characteristics of the engineered MSPs, including stabilities based on thermal and chemical denaturation. Compositions and stoichiometries of components in disks can be quantitated by traditional methods, using radioactive or fluorescent labels, mass spectrometry, etc. of protein and lipid components.

AFM is used to provide molecular resolution data on the structural organizations of the lipid and protein components of the Nanodiscs of the present invention. This technique can be used in air, vacuum, and under aqueous and non-aqueous fluids. The latter capability has made it the most important scanning probe technique in the biological sciences. The AFM is a very versatile instrument as it is capable of acquiring images and other forms of force data in contact, tapping, phase, and lateral force modes (Sarid, 1994). These scanning modes are available on the Digital Instruments Multimode Scanning Probe Microscope (Digital Instruments, Plainview, N.Y.), and they have been successfully used to image rHDL and proteins associated with Nanodiscs both with and without incorporated proteins. This instrument can also be used in STM and electrochemical modes to study characteristics of gold-associated Nanodiscs and incorporated redox proteins.

As used herein, membrane scaffold proteins are artificial (do not exist in nature) proteins or polypeptides which self-assemble phospholipids and phospholipid mixtures into nanometer size membrane bilayers. A subset of these structures are discoidal in shape and are referred to as Nanodiscs. Hydrophobic proteins, e.g., membrane proteins, or membrane fragments can associate with these particles such that the hydrophobic proteins or membrane fragments are effectively solubilized in a stable structure which maintains the functionality of the protein with respect to enzymatic activity or ligand binding. These particles are stable in solution or they can be fixed to a surface, advantageously in a uniform orientation with respect to the surface. As used herein, a nanoparticle comprising MSPs (with or without another hydrophobic or a partially hydrophobic protein) can be from about 5 to about 500 nm, desirably about 5 to about 100 nm, or about 5 to about 20 nm in diameter. Nanoparticles (disks) of about 5 to about 15 nm in diameter are especially useful.

We have shown that both MSP1 and MSP2 assemble with bacteriorhodopsin. From the initial reconstitution mixture, two bacteriorhodopsin-containing species are observed when particles are formed with MSP1 or MSP2 in the absence of added phospholipid. MSP is absolutely required for the solubilization of bacteriorhodopsin to form these species because omission of an MSP from the formation mixture results in large non-specific bacteriorhodopsin aggregates that elute in the void volume of the gel filtration column. The majority of bacteriorhodopsin appeared solubilized in the presence of MSPs.

Modifications of MSP primary structure can generate alternative and more effective and stable membrane scaffold proteins. For instance, we have deleted a region of MSP1 to produce two new membrane scaffold proteins. In the first case, two regions of the protein believed to participate in helix formation were deleted to produce a construct called MSP1Da. In a second experiment, one region deleted in SMP1Da and an additional region believed to participate in helix formation were deleted to produce a material termed MSP1Db. We have overexpressed these proteins in E. coli, which are expressed at high levels upon induction of expression with isopropyl-thio-$\beta$-D-galactopyranoside in lac-regulated constructs.

Careful attention to the concentrations of MSP in the reconstitution mixture is necessary to insure homogeneity with respect to the sizes of Nanodiscs produced. The optimal phospholipid to MSP ratio depends on the overall size Nanodisc generated, which is in turn determined by the overall length of the encircling membrane scaffold protein. For example, the MSP1 scaffold protein self assembles to form a nominally 9.7 nm diameter disc with 163 DPPC phospholipid molecules incorporated per Nanodisc (81.6 per MSP1). For Nanodiscs which are engineered to be larger by adding additional helical segments within the MSP, more phospholipids (PL) are enclosed. MSPE1 with an additional 22-mer helix generates particles of diameter 10.4 nm and 105.7 PL per MSPE1. With two 22-mer helices inserted into the SMP, a Nanodisc of diameter 11.1 nm is generated with 138.2 PL molecules per MSP1E2. With three 22-mer helices added, a 12 nm particle is produced with 176.6 DPPC molecules per resulting Nanodisc.

Figure 14:
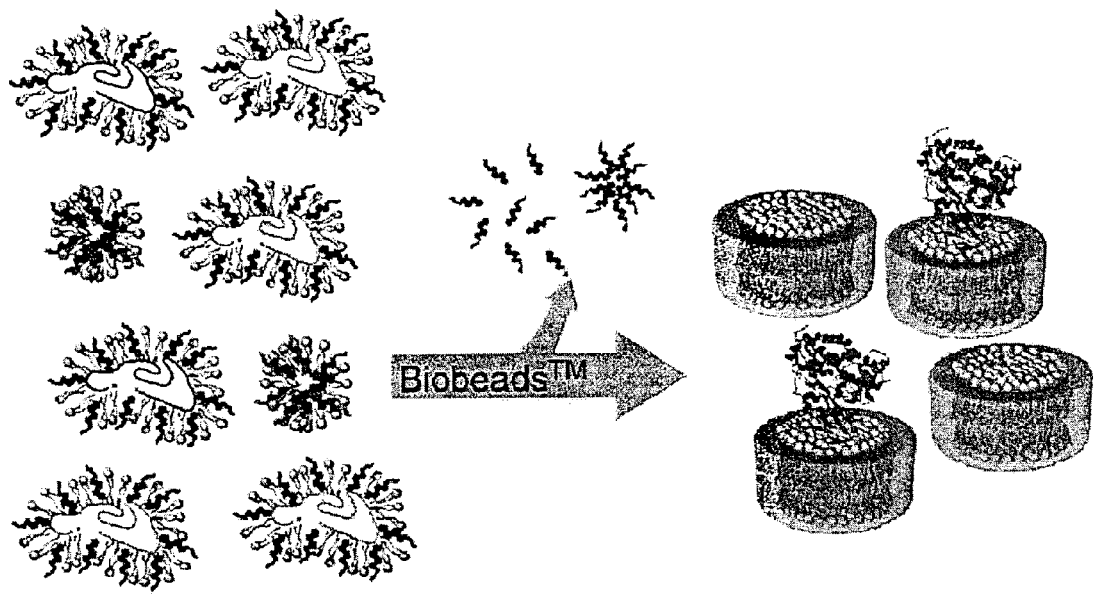
FIG. 14 provides a schematic describing the formation of nanoscale supported lipid bilayers (Nanodiscs) through self-assembly. A cell membrane preparation containing the target membrane protein is solubilized with detergent in the presence of membrane scaffold protein (MSP) (see herein below). Upon removal of the detergent, by dialysis or Biobeads™, a soluble MSP-supported Nanodisc, is formed with the target incorporated into the resulting phospholipid bilayer.
Figure 15A:
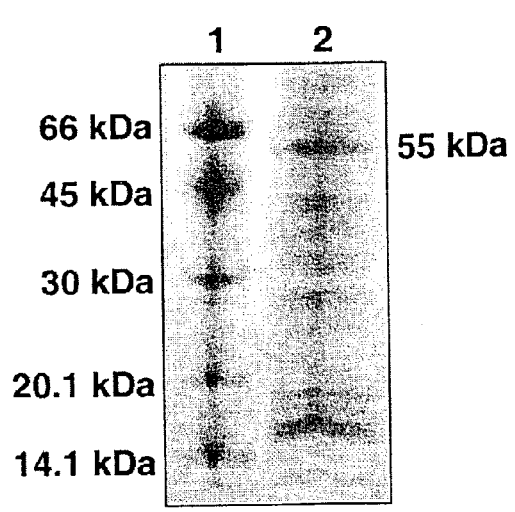
FIG. 15 shows the results of one dimensional SDS-PAGE of Nanodisc mixture. Lanes 1, low molecular weight markers. Lane 2 (left panel), Sf9 insect cell membranes infected for the overexpression of CYP6B1. The band at 55 kDa represents the overexpressed target membrane-bound protein. Lane 3 (right panel) illustrates the Nanodisc mixture assembled from Sf9 insect cell membranes overexpressing CYP6B1. MSP1 and CYP6B1 run at molecular weights of 25 kDa and 55 kDa, respectively.
Figure 15B:
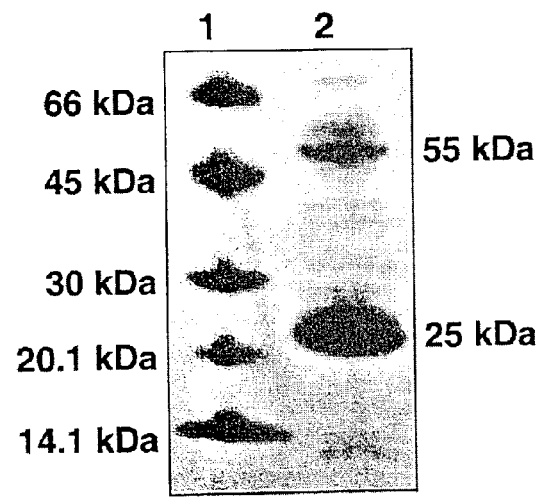

To adapt MSP technology to a format compatible with proteomic analysis of heterologously-expressed membrane proteins, membranes from Sf9 cells overexpressing CYP6B1 were completely solubilized with detergent in the presence of the engineered membrane scaffold protein MSP1. Removal of the detergent (using Biobeads®) initiated self-assembly, allowing for the incorporation of the membrane protein population into MSP-supported phospholipid nanobilayers, as outlined in FIG. 14. The MSP1-containing particles were subsequently isolated using a nickel-chelating resin to bind the His6-tag on the N-terminus of the scaffold protein. Analysis of the affinity-purified soluble nanobilayers by denaturing polyacrylamide gel electrophoresis confirmed the presence of the CYP6B1 target protein as well as an array of endogenous proteins present in the original Sf9 cell membranes (FIG. 15). The nickel affinity-purified sample was fractionated by size exclusion chromatography (FIG. 16A) and analyzed by absorbance at 417 nm to identify a 10 nm fraction containing over 90% of the solubilized heme-containing target protein.

Size exclusion chromatography of CYP6B1-expressing Sf9 cell membranes treated and fractionated in the absence of the membrane scaffold protein shows that the target elutes as large, non-specific aggregates (FIG. 16A, dotted line). The homogeneity of the MSP1-supported Nanodiscs generated is dependent on the identity of lipid and its ratio of lipid to the amount of MSP used in the reconstitution procedure (Bayburt et al., 2002) supra). Our analysis of MSP disks assembled with the natural lipid pool from Sf9 insect cell membranes indicates other size populations in the initial nickel affinity-purified Nanodiscs (FIG. 16A). These variations are due to the difficulty in determining a priori the precise concentration of MSP protein ideally matched to the lipid composition in membrane preparations expressing variable amounts of the heterologous P450 protein and to the significant size distribution of the endogenous membrane proteins that are also assembled into nanostructures in this process. These other size classes represent non-specific aggregates that are easily separated from the about 10 nm diameter nanobilayer assemblies. Size-fractionated populations of Nanodiscs containing the P450 target protein are uniform and stable through re-fractionation on the Superdex™ 200 sizing column. The final CYP6B1-containing population displays a stoichiometry of approximately one CYP6B1 protein per 10 Nanodiscs (FIG. 16B).

We have studied the lipid composition of Nanodiscs formed with natural cell membranes. The successful application of MSP technology to the assembly of nanobilayers from natural biological membranes provides a unique opportunity for the direct isolation of membrane proteins from cells and their solubilization and dispersal into a system that closely mimics the native cell environment. To further clarify the extent to which the phospholipid content of the isolated Nanodiscs mimics that of the original Sf9 microsomal membranes, nickel affinity-purified nanostructures assembled with Sf9 microsomal membranes were analyzed by thin-layer chromatography. Comparisons of these Nanodisc phospholipid populations with the major phospholipid types found in insect cell membranes, which are phosphatidylcholine, phosphatidylinositol, and phosphatidylethanolamine (Marheineke et al., 1998) (FIG. 17), clearly indicate that the phospholipid composition of endogenous Sf9 microsomal membranes is preserved in assembled Nanodiscs.

Figure 18:
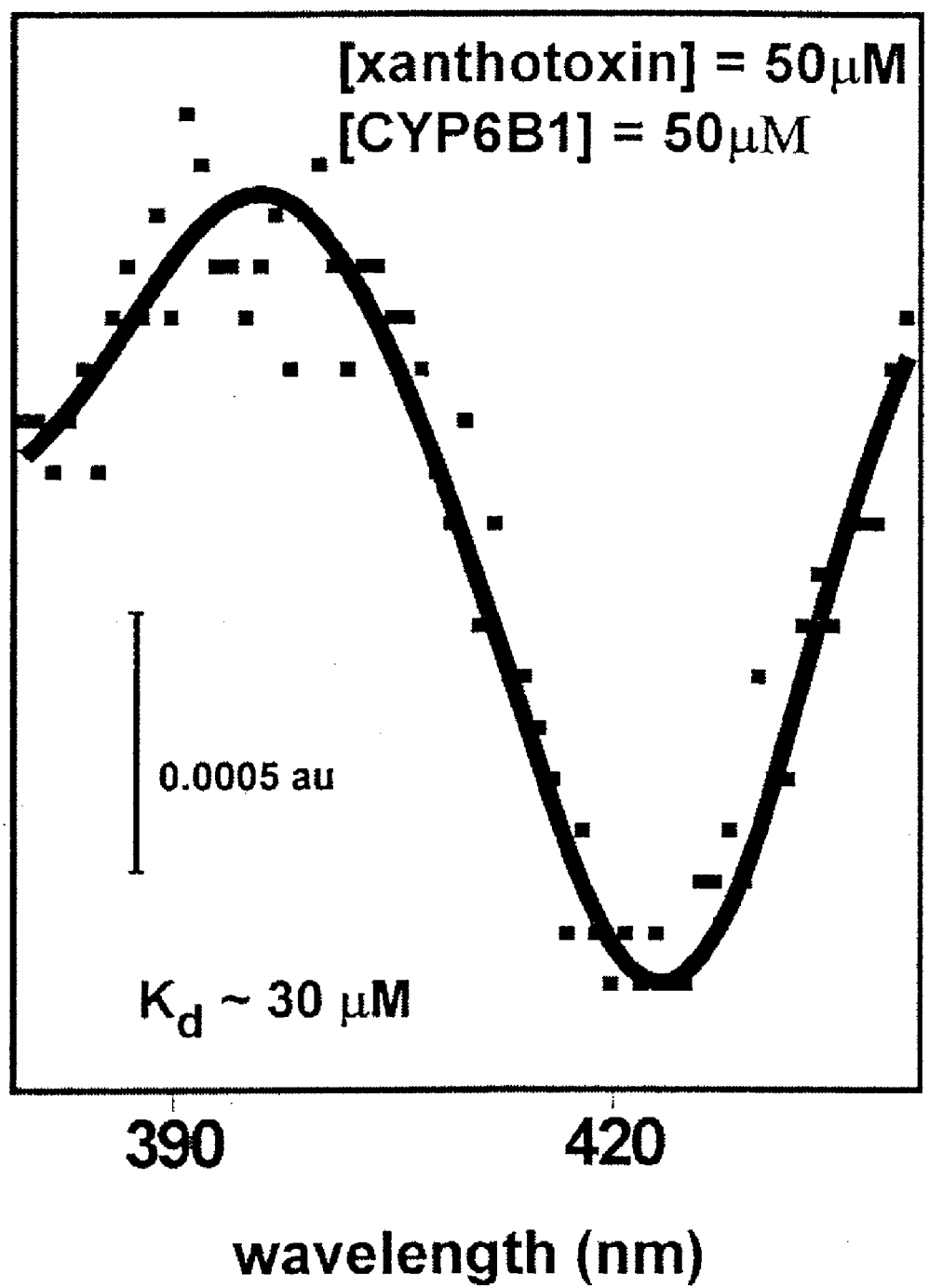
FIG. 18 shows ligand binding to CYP6B1 incorporated into Nanodisc membrane bilayers with MSP1. The characteristic "Type I" binding spectra (decrease in substrate low spin cytochrome with absorbance at about 417 nm and concomitant increase in the high spin fraction absorbing at about 390 nm) is obtained in microtiter plates using high-throughput plate reader following incremental addition of the environmental furanocoumarin xanthotoxin. A dissociation constant of roughly 30 µM was calculated.

We have examined the integrity of the membrane protein assembled into Nanodiscs. CYP6B1-containing nanostructures were assayed by reduction of the iron and binding of carbon monoxide (CO), which monitors via an absorbance maximum at 450 nm the quantity of protein that is intact and correctly configured for P450-mediated catalysis (Omura and Sato (1964) (FIG. 18). This spectral assay indicates a clear absence of absorbance at 420 nm and documents the fact that normally labile proteins, such as P450s, are incorporated in their native form into Nanodiscs suitable for subsequent fractionation and biochemical analysis. To further demonstrate that the solubilized membrane protein is accessible for binding substrate and suitable for use in high-throughput optical analysis, binding of xanthotoxin, one of several furanocoumarin substrates metabolized by this P450, to MSP1- and CYP6B1-containing Nanodiscs was analyzed in 96-well microtiter plates using a sample volume of only 200 μL Nanodiscs (10 picomoles enzyme) and varying concentrations of substrate. The Type-I binding spectra (Estabrook and Werringloer, 1978) obtained at varying concentrations of xanthotoxin show an absorbance shift from 420 nm to 390 nm that is characteristic of substrates effectively displacing water as the sixth ligand to the heme iron in the P450 catalytic site and converting the iron from low spin to high spin. The data presented in FIG. 18 clearly illustrate that CYP6B1's ability to bind substrate is maintained throughout the Nanodisc assembly and subsequent fractionation process.

In summary, the present invention provides an important tool for the study of membrane protein targets as well as the complicated multi-component assemblies present in cellular bilayers. When coupled with our ability to express individual cloned P450s or other membrane proteins in the frequently used baculovirus, yeast and mammalian expression systems, these technologies present the opportunity to display single membrane proteins supported in native membrane bilayers in the development of biochemical methodologies previously restricted to soluble proteins. The lipid composition of the particles derived from MSP and membranes or membrane fragments mimics that of the starting membranes or fragments. This contributes to maintaining the native conformation and activity of the membrane protein which becomes incorporated into the particles with MSP. The ability to bind substrates, inhibitors and other interacting molecules with these solubilized membrane proteins using sensitive optical difference spectra in microtiter plates enables the development of high throughput screening methods for many different types of membrane proteins. The fact that the Nanodisc solubilization procedures can be applied nonspecifically to all membrane proteins means that this technology can be used to solubilize and fractionate many pharmacological target proteins directly out of cellular membranes. Coupled with the histidine tag on the MSP molecule, this technology the immobilization of target proteins on surfaces suitable for high throughput screening. All the MSPs described herein can be used in preparing Nanodiscs with purified and solubilized hydrophobic or partially hydrophobic proteins or with hydrophobic or partially hydrophobic membrane proteins solubilized from membrane or membrane fragment preparations.

Monoclonal or polyclonal antibodies, preferably monoclonal, specifically reacting with an MSP of the present invention can be made by methods known in the art. See, e.g., Harlow and Lane (1988) *Antibodies: A Laboratory Manual*, Cold Spring Harbor Laboratories; Goding (1986) *Monoclonal Antibodies: Principles and Practice*, 2d ed., Academic Press, New York; and Ausubel et al. (1993) *Current Protocols in Molecular Biology*, Wiley Interscience, New York, N.Y.

Standard techniques for cloning, DNA isolation, amplification and purification, for enzymatic reactions involving DNA ligase, DNA polymerase, restriction endonucleases and the like, and various separation techniques are those known and commonly employed by those skilled in the art. A number of standard techniques are described in Sambrook et al. (1989) *Molecular Cloning*, Second Edition, Cold Spring Harbor Laboratory, Plainview, N.Y.; Maniatis et al. (1982) *Molecular Cloning*, Cold Spring Harbor Laboratory, Plainview, N.Y.; Wu (ed.) (1993) *Meth. Enzymol.* 218, Part I; Wu (ed.) (1979) *Meth. Enzymol.* 68; Wu et al. (eds.) (1983) *Meth. Enzymol.* 100 and 101; Grossman and Moldave (eds.) *Meth. Enzymol.* 65; Miller (ed.) (1972) *Experiments in Molecular Genetics*, Cold Spring Harbor Laboratory, Cold Spring Harbor, N.Y.; Old and Primrose (1981) *Principles of Gene Manipulation*, University of California Press, Berkeley; Schleif and Wensink (1982) *Practical Methods in*

*Molecular Biology*; Glover (ed.) (1985) *DNA Cloning* Vol. I and II, IRL Press, Oxford, UK; Hames and Higgins (eds.) (1985) *Nucleic Acid Hybridization*, IRL Press, Oxford, UK; Setlow and Hollaender (1979) *Genetic Engineering: Principles and Methods*, Vols. 1–4, Plenum Press, New York; and Ausubel et al. (1992) *Current Protocols in Molecular Biology*, Greene/Wiley, New York, N.Y. Abbreviations and nomenclature, where employed, are deemed standard in the field and commonly used in professional journals such as those cited herein.

All references cited in the present application are incorporated by reference herein to the extent that there is no inconsistency with the present disclosure. U.S. Ser. No. 09/990,087 filed Nov. 20, 2001 and U.S. Ser. No. 60/252,233, filed Nov. 20, 2000, are incorporated by reference herein to the extent there is no inconsistency with the present disclosure.

The description provided herein is not intended to limit the scope of the invention as claimed herein. Any variations in the exemplified articles and methods which occur to the skilled artisan are intended to fall within the scope of the present invention.

EXAMPLES

Example 1

Construction of Recombinant DNA Molecules for Expression of MSPs

The human proapoAI coding sequence as given below was inserted between Nco I and Hind III sites (underlined) in pET-28 (Novagen, Madison, Wis.). Start and stop codons are in bold type. The restriction endonuclease recognition sites used in cloning are underlined.

TABLE 1

ProApoAI coding sequence (SEQ ID NO:1)
CCATGGCCCATTTCTGGCAGCAAGATGAACCCCCCCAGAGCCCCTGGGAT

CGAGTGAAGGACCTGGCCACTGTGTACGTGGATGTGCTCAAAGACAGCGG

CAGAGACTATGTGTCCCAGTTTGAAGGCTCCGCCTTGGGAAAACAGCTAA

ACCTAAAGCTCCTTGACAACTGGGACAGCGTGACCTCCACCTTCAGCAAG

CTGCGCGAACAGCTCGGCCCTGTGACCCAGGAGTTCTGGGATAACCTGGA

AAAGGAGACAGAGGGCCTGAGGCAAGAGATGAGCAAGGATCTGGAGGAGG

TGAAGGCCAAGGTGCAGCCCTACCTGGACGACTTCCAGAAGAAGTGGCAG

GAGGAGATGGAGCTCTACCGCCAGAAGGTGGAGCCGCTGCGCGCAGAGCT

CCAAGAGGGCGCGCGCCAGAAGCTGCACGAGCTGCAAGAGAAGCTGAGCC

CACTGGGCGAGGAGATGCGCGACCGCGCGCGCGCCCATGTGGACGCGCTG

CGCACGCATCTGGCCCCCTACAGCGACGAGCTGCGCCAGCGCTTGGCCGC

GCGCCTTGAGGCTCTCAAGGAGAACGGCGGCGCCAGACTGGCCGAGTACC

ACGCCAAGGCCACCGAGCATCTGAGCACGCTCAGCGAGAAGGCCAAGCCC

GCGCTCGAGGACCTCCGCCAAGGCCTGCTGCCCGTGCTGGAGAGCTTCAA

GGTCAGCTTCCTGAGCGCTCTCGAGGAGTACACTAAGAAGCTCAACACCC

AGTAATAAGCTT-3'

Restriction sites used m cloning are underlined, and the translation start and stop signals are shown in bold.

TABLE 2

ProApo AT amino acid sequence (SEQ ID NO:2)
MAHFWQQDEPPQSPWDRVKDLATVYVDVLKDSGRDYVSQFEGSALGKQLN

LKLLDNWDSVTSTFSKLREQLGPVTQEFWDNLEKETEGLRQEMSKDLEEV

KAKVQPYLDDFQKKWQEEMELYRQKVEPLRAELQEGARQKLHELQEKLSP

LGEEMRDRARAHVDALRTHLAPYSDELRQRLAARLEALKENGGARLAEYH

AKATEHLSTLSEKAKPALEDLRQGLLPVLESFKVSFLSALEEYTKKLNTQ

The construction of the MSP1 coding sequence was accomplished as follows. Primers were designed to produce DNA encoding MSP1, the truncated protein lacking the N-terminal domain of proApoAI, by polymerase chain reaction (PCR) mutagenesis (Higuchi et al., 1988).

Primer 1 (SEQ ID NO:3) (5'-TATACCATGGGCCATCATC ATCATCATCATATAGAAGGAAGACTAAAGCTCCT TGACAACT-3') introduces an N-terminal 6-histidine tag for purification and manipulation of MSP1, and a factor Xa cleavage site for removal of the histidine tag. Factor Xa cleaves after R in the protein sequence IEGR. IEGR corresponds to amino acids 9–12 of SEQ ID NO:47.

Primer 2 (SEQ ID NO:4) (5'-GCAAGCTTATTACTGGGT-GTTGAGCTTCTT-3') was used as a reverse primer.

TABLE 3

Histidine-tagged MSP1 coding sequence.

(SEQ ID NO:5)
TATACCATGGGCCATCATCATCATCATCATATAGAAGGAAGACTAAAGCT

CCTTGACAACTGGGACAGCGTGACCTCCACCTTCAGCAAGCTGCGCGAAC

AGCTCGGCCCTGTGACCCAGGAGTTCTGGGATAACCTGGAAAAGGAGACA

GAGGGCCTGAGGCAGGAGATGAGCAAGGATCTGGAGGAGGTGAAGGCCAA

GGTGCAGCCCTACCTGGACGACTTCCAGAAGAAGTGGCAGGAGGAGATGG

AGCTCTACCGCCAGAAGGTGGAGCCGCTGCGCGCAGAGCTCCAAGAGGGC

GCGCGCCAGAAGCTGCACGAGCTGCAAGAGAAGTTGAGCCCACTGGGCGA

GGAGATGCGCGACCGCGCGCGCGCCCATGTGGACGCGCTGCGCACGCATC

TGGCCCCCTACAGCGACGAGCTGCGCCAGCGCTTGGCCGCGCGCCTTGAG

GCTCTCAAGGAGAACGGCGGCGCCAGACTGGCCGAGTACCACGCCAAGGC

CACCGAGCATCTGAGCACGCTCAGCGAGAAGGCCAAACCCGCGCTCGAGG

ACCTCCGCCAAGGCCTGCTGCCCGTGCTGGAGAGCTTCAAGGTCAGCTTC

CTGAGCGCTCTCGAGGAGTACACTAAGAAGCTCAACACCCAGTAATAAGC

TTGC

Restriction sites used in cloning are underlined, and the translation start and stop signals are shown in bold.

TABLE 4

Histidine-tagged MSP1 amino acid sequence (SEQ ID NO:6)
MGHHHHHHIEGRLKLLDNWDSVTSTFSKLREQLGPVTQEFWDNLEKETEG

LRQEMSKDLEEVKAKVQPYLDDFQKKWQEEMELYRQKVEPLRAELQEGAR

QKLHELQEKLSPLGEEMRDRARAHVDALRTHLAPYSDELRQRLAARLEAL

TABLE 4-continued

Histidine-tagged MSP1 amino acid sequence

KENGGARLAEYHAKATEHLSTLSEKAKPALEDLRQGLLPVLESFKVSFLS

ALEEYTKKLNTQ

For production of MSP1 without a N-terminal histidine tag, primer 1 was replaced with primer 1a: 5'-TACCATG-GCAAAGCTCCTTGACAACTG-3' (SEQ ID NO:7) to produce the sequence provided in SEQ ID NO:8.

TABLE 5

Non-Histidine-tagged MSP1 DNA sequence.

(SEQ ID NO:8)
TA<u>CCATGG</u>CAAAGCTCCTTGACAACTGGGACAGCGTGACCTCCACCTTCA

GCAAGCTGCGCGAACAGCTCGGCCCTGTGACCCAGGAGTTCTGGGATAAC

CTGGAAAAGGAGACAGAGGGCCTGAGGCAGGAGATGAGCAAGGATCTGGA

GGAGGTGAAGGCCAAGGTGCAGCCCTACCTGGACGACTTCCAGAAGAAGT

GGCAGGAGGAGATGGAGCTCTACCGCCAGAAGGTGGAGCCGCTGCGCGCA

GAGCTCCAAGAGGGCGCGCGCCAGAAGCTGCACGAGCTGCAAGAGAAGTT

GAGCCCACTGGGCGAGGAGATGCGCGACCGCGCGCGCGCCCATGTGGACG

CGCTGCGCACGCATCTGGCCCCCTACAGCGACGAGCTGCGCCAGCGCTTG

GCCGCGCGCCTTGAGGCTCTCAAGGAGAACGGCGGCGCCAGACTGGCCGA

GTACCACGCCAAGGCCACCGAGCATCTGAGCACGCTCAGCGAGAAGGCCA

AACCCGCGCTCGAGGACCTCCGCCAAGGCCTGCTGCCCGTGCTGGAGAGC

TTCAAGGTCAGCTTCCTGAGCGCTCTCGAGGAGTACACTAAGAAGCTCAA

CACCCAGTAA<u>AAGCTT</u>GC

Restriction sites used in cloning are underlined, and the translation start and stop signals are shown in bold.

TABLE 6

Non-Histidine-tagged MSP1 amino acid sequence.

(SEQ ID NO:9)
MAKLLDNWDSVTSTFSKLREQLGPVTQEFWDNLEKETEGLRQEMSKDLEE

VKAKVQPYLDDFQKKWQEEMELYRQKVEPLRAELQEGARQKLHELQEKLS

PLGEEMRDRARAHVDALRTHLAPYSDELRQRLAARLEALKENGGARLAEY

HAKATEHLSTLSEKAKPALEDLRQGLLPVLESFKVSFLSALEEYTKKLNT

Q

Figure 6A:
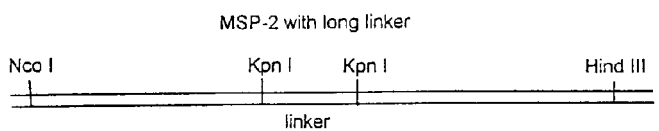
FIGS. 6A–6B shows diagrams of MSP2 with (FIG. 6A) and without a long linker sequence (FIG. 6B).
Figure 6B:
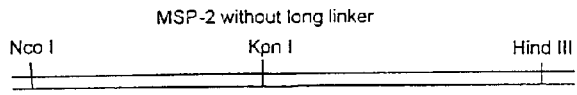

The production of an MSP with tandem repeats (MSP2) was carried at as described below. The following primers were used to generate MSP2 (see FIGS. 6A–6B):

| | | |
|---|---|---|
| Primer 3: | 5'-TACCATGGCAAAGCTCCTTGACAACTG-3' | (SEQ ID NO:10) |
| primer 3a: | 5'-TATACCATGGGCCATCATCATCATCATCATATAGAAGGA<br>AGACTAAAGCTCCTTGACAACT-3' | (SEQ ID NO:11) |
| Primer 4: | 5'-TAAGAAGCTCAACACCCAGGGTACCGGTGGAGGTAGTGGAGGTGGTACCCTA-3' | (SEQ ID NO:12) |
| Primer 5: | 5'-CAGGGTACCGGTGGAGGTAGTGGAGGTGGTACCCTAAAGCTCCTTGACAA-3' | (SEQ ID NO:13) |
| Primer 6: | 5'-GCAAGCTTATTACTGGGTGTTGAGCTTCTT-3' | (SEQ ID NO:14) |

Figure 7B:
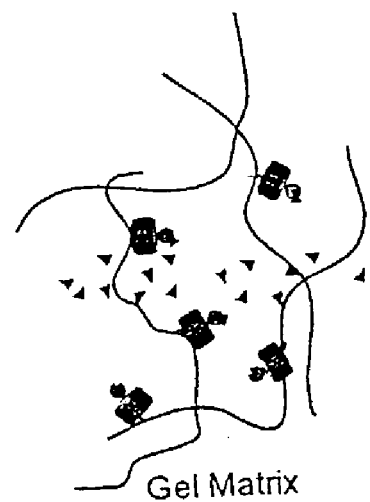
Figure 8:
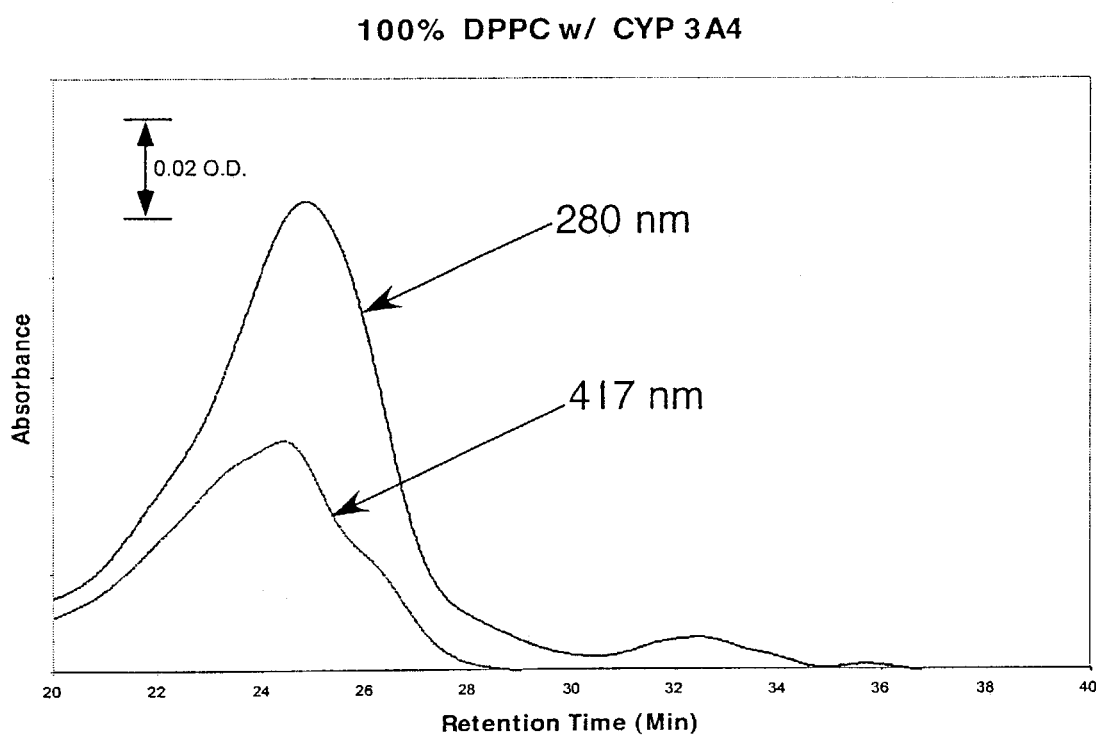
FIG. 8 is a chromatogram of cytochrome P450 3A4 incorporated into 10 nm bilayer disks composed of 100% DPPC.

In a first PCR, primer 2 (or primer 2a for N-terminal histidine tag) and primer 4 were used to add a linker (encoding the amino acid sequence GTGGGSGGGT; SEQ ID NO:15) to the 3' end of the MSP gene to produce MSP-A. In a second PCR, the linker was added to the 5' end of the MSP gene to produce MSP-B. Treatment of MSP-A and MSP-B with KpnI and subsequent ligation produced the following constructs, one with and one without the linker. The Kpn I site provides an easy way to inserting any desired linker sequence by restriction with Kpn I and religation with double-stranded synthetic DNA encoding desired linker. See FIGS. 7A–7B.

TABLE 7

MSP2 (with histidine tag, without long linker) DNA sequence.

(SEQ ID NO:16)
TATA<u>CCATGG</u>GCCATCATCATCATCATCATATAGAAGGAAGACTAAAGCT

CCTTGACAACTGGGACAGCGTGACCTCCACCTTCAGCAAGCTGCGCGAAC

AGCTCGGCCCTGTGACCCAGGAGTTCTGGGATAACCTGGAAAAGGAGACA

GAGGGCCTGAGGCAGGAGATGAGCAAGGATCTGGAGGAGGTGAAGGCCAA

GGTGCAGCCCTACCTGGACGACTTCCAGAAGAAGTGGCAGGAGGAGATGG

AGCTCTACCGCCAGAAGGTGGAGCCGCTGCGCGCAGAGCTCCAAGAGGGC

GCGCGCCAGAAGCTGCACGAGCTGCAAGAGAAGCTGAGCCCACTGGGCGA

GGAGATGCGCGACCGCGCGCGCGCCCATGTGGACGCGCTGCGCACGCATC

TGGCCCCCTACAGCGACGAGCTGCGCCAGCGCTTGGCCGCGCGCCTTGAG

GCTCTCAAGGAGAACGGCGGCGCCAGACTGGCCGAGTACCACGCCAAGGC

CACCGAGCATCTGAGCACGCTCAGCGAGAAGGCCAAGCCCGCGCTCGAGG

ACCTCCGCCAAGGCCTGCTGCCCGTGCTGGAGAGCTTCAAGGTCAGCTTC

CTGAGCGCTCTCGAGGAGTACACTAAGAAGCTCAACACCCAGGGTACCCT

AAAGCTCCTTGACAACTGGGACAGCGTGACCTCCACCTTCAGCAAGCTGC

GCGAACAGCTCGGCCCTGTGACCCAGGAGTTCTGGGATAACCTGGAAAAG

GAGACAGAGGGCCTGAGGCAGGAGATGAGCAAGGATCTGGAGGAGGTGAA

GGCCAAGGTGCAGCCCTACCTGGACGACTTCCAGAAGAAGTGGCAGGAGG

AGATGGAGCTCTACCGCCAGAAGGTGGAGCCGCTGCGCGCAGAGCTCCAA

GAGGGCGCGCGCCAGAAGCTGCACGAGCTGCAAGAGAAGCTGAGCCCACT

GGGCGAGGAGATGCGCGACCGCGCGCGCGCCCATGTGGACGCGCTGCGCA

CGCATCTGGCCCCCTACAGCGACGAGCTGCGCCAGCGCTTGGCCGCGCGC

CTTGAGGCTCTCAAGGAGAACGGCGGCGCCAGACTGGCCGAGTACCACGC

CAAGGCCACCGAGCATCTGAGCACGCTCAGCGAGAAGGCCAAGCCCGCGC

TABLE 7-continued

MSP2 (with histidine tag, without long linker) DNA sequence.

TCGAGGACCTCCGCCAAGGCCTGCTGCCCGTGCTGGAGAGCTTCAAGGTC

AGCTTCCTGAGCGCTCTCGAGGAGTACACTAAGAAGCTCAACACCCAGTA

AT<u>AAGCTT</u>GC

The translation start and stop codons are in bold type, and the restriction endonuclease recognition sites used in cloning are underlined.

TABLE 8

MSP2 (with histidine tag, without long linker) amino acid sequence (SEQ ID NO:17)
MGHHHHHHIEGRLKLLDNWDSVTSTFSKLREQLGPVTQEFWDNLEKETEG

LRQEMS/KDLEEVKAKVQPYLDDFQKKWQEEMELYRQKVEPLRAELQEGA

RQKLHELQEKLSPLGEEMRDRARAHVDALRTHLAPYSDELRQRLAARLEA

LKENGGARLAEYHAKATEHLSTLSEKAKPALEDLRQGLLPVLESFKVSFL

SALEEYTKKLNTQGTLKLLDNWDSVTSTFSKLREQLGPVTQEFWDNLEKE

TEGLRQEMSKDLEEVKAKVQPYLDDFQKKWQEEMELYRQKVEPLRAELQE

GARQKLHELQEKLSPLGEEMRDRARAHVDALRTHLAPYSDELRQRLAARL

EALKENGGARLAEYHAKATEHLSTLSEKAKPALEDLRQGLLPVLESFKVS

FLSALEEYTKKLNTQ

TABLE 9

MSP2L(with histidine tag, with long linker) DNA sequence.

(SEQ ID NO:18)
TA<u>CCATGG</u>GCCATCATCATCATCATCATATAGAAGGAAGACTAAAGCTCC

TTGACAACTGGGACAGCGTGACCTCCACCTTCAGCAAGCTGCGCGAACAG

CTCGGCCCTGTGACCCAGGAGTTCTGGGATAACCTGGAAAAGGAGACAGA

GGGCCTGAGGCAGGAGATGAGCAAGGATCTGGAGGAGGTGAAGGCCAAGG

TGCAGCCCTACCTGGACGACTTCCAGAAGAAGTGGCAGGAGGAGATGGAG

CTCTACCGCCAGAAGGTGGAGCCGCTGCGCGCAGAGCTCCAAGAGGGCGC

GCGCCAGAAGCTGCACGAGCTGCAAGAGAAGCTGAGCCCACTGGGCGAGG

AGATGCGCGACCGCGCGCGCGCCCATGTGGACGCGCTGCGCACGCATCTG

GCCCCCTACAGCGACGAGCTGCGCCAGCGCTTGGCCGCGCGCCTTGAGGC

TCTCAAGGAGAACGGCGGCGCCAGACTGGCCGAGTACCACGCCAAGGCCA

CCGAGCATCTGAGCACGCTCAGCGAGAAGGCCAAGCCCGCGCTCGAGGAC

CTCCGCCAAGGCCTGCTGCCCGTGCTGGAGAGCTTCAAGGTCAGCTTCCT

GAGCGCTCTCGAGGAGTACACTAAGAAGCTCAACACCCAGGGTACCGGTG

GAGGTAGTGGAGGTGGTACCCTAAAGCTCCTTGACAACTGGGACAGCGTG

TABLE 9-continued

MSP2L(with histidine tag, with long linker) DNA sequence.

ACCTCCACCTTCAGCAAGCTGCGCGAACAGCTCGGCCCTGTGACCCAGGA

GTTCTGGGATAACCTGGAAAAGGAGACAGAGGGCCTGAGGCAGGAGATGA

GCAAGGATCTGGAGGAGGTGAAGGCCAAGGTGCAGCCCTACCTGGACGAC

TTCCAGAAGAAGTGGCAGGAGGAGATGGAGCTCTACCGCCAGAAGGTGGA

GCCGCTGCGCGCAGAGCTCCAAGAGGGCGCGCGCCAGAAGCTGCACGAGC

TGCAAGAGAAGCTGAGCCCACTGGGCGAGGAGATGCGCGACCGCGCGCGC

GCCCATGTGGACGCGCTGCGCACGCATCTGGCCCCCTACAGCGACGAGCT

GCGCCAGCGCTTGGCCGCGCGCCTTGAGGCTCTCAAGGAGAACGGCGGCG

CCAGACTGGCCGAGTACCACGCCAAGGCCACCGAGCATCTGAGCACGCTC

AGCGAGAAGGCCAAGCCCGCGCTCGAGGACCTCCGCCAAGGCCTGCTGCC

CGTGCTGGAGAGCTTCAAGGTCAGCTTCCTGAGCGCTCTCGAGGAGTACA

CTAAGAAGCTCAACACCCAGTAA<u>AAGCTT</u>GC

Translation start and stop codons are in bold type; restriction endonuclease sites used in cloning are underlined.

TABLE 10

MSP2 (with histidine tag, with long linker, in bold type) amino acid sequence.

(SEQ ID NO:19)
MGHHHHHHIEGRLKLLDNWDSVTSTFSKLREQLGPVTQEFWDNLEKETEG

LRQEMSKDLEEVKAKVQPYLDDFQKKWQEEMELYRQKVEPLRAELQEGAR

QKLHELQEKLSPLGEEMRDRARAHVDALRTHLAPYSDELRQRLAARLEAL

KENGGARLAEYHAKATEHLSTLSEKAKPALEDLRQGLLPVLESFKVSFLS

ALEEYTKKLNTQGTGGGSGGGTLKLLDNWDSVTSTFSKLREQLGPVTQEF

WDNLEKETEGLRQEMSKDLEEVKAKVQPYLDDFQKKWQEEMELYRQKVEP

LRAELQEGARQKLHELQEKLSPLGEEMRDRARAHVDALRTHLAPYSDELR

QRLAARLEALKENGGARLAEYHAKATEHLSTLSEKAKPALEDLRQGLLPV

LESFKVSFLSALEEYTKKLNTQ

To delete hinge regions, deletion of helices 4 and 5 was carried out by constructing the C-terminal portion of MSP1 using the following PCR primers and the Sac I and Hind III fragment of the MSP1 coding sequence as template.

Primer A: 5'-TGGAGCTCTACCGCCAGAAGGTGGAGCCCTACAGCGACGAGCT-3' (SEQ ID NO:20)

Primer B: 5'-GCAAGCTTATTACTGGGTGTTGAGCTTCTT-3'. (SEQ ID NO:21)

This amplification product was digested with SacI and HindIII and ligated into pLitmus 28 for sequencing. The Sac I+HindIII treated histidine-tagged MSP1 construct in pET 28 vector was then ligated with the above fragment to produce MSP1Da.

TABLE 11

MSP1D5D6 DNA sequence.

(SEQ ID NO:22)
TATA<u>CC<b>ATG</b>G</u>GCCATCATCATCATCATCATATAGAAGGAAGACTAAAGCT

CCTTGACAACTGGGACAGCGTGACCTCCACCTTCAGCAAGCTGCGCGAAC

AGCTCGGCCCTGTGACCCAGGAGTTCTGGGATAACCTGGAAAAGGAGACA

GAGGGCCTGAGGCAGGAGATGAGCAAGGATCTGGAGGAGGTGAAGGCCAA

GGTGCAGCCCTACCTGGACGACTTCCAGAAGAAGTGGCAGGAGGAGATGG

AGCTctaccgccagaaggtggagcCCTACAGCGACGAGCTGCGCCAGCGC

TTGGCCGCGCGCCTTGAGGCTCTCAAGGAGAACGGCGGCGCCAGACTGGC

CGAGTACCACGCCAAGGCCACCGAGCATCTGAGCACGCTCAGCGAGAAGG

CCAAACCCGCGCTCGAGGACCTCCGCCAAGGCCTGCTGCCCGTGCTGGAG

AGCTTCAAGGTCAGCTTCCTGAGCGCTCTCGAGGAGTACACTAAGAAGCT

CAACACCCAG<b>TAA</b><u>AAGCTT</u>GC

Translations start and stop codons are in bold type; restriction endonuclease recognition sites are underlined.

TABLE 12

MSP1D5D6 amino acid sequence.

(SEQ ID NO:23)
MGHHHHHHIEGRLKLLDNWDSVTSTFSKLREQLGPVTQEFWDNLEKETEG

LRQEMSKDLEEVKAKVQPYLDDFQKKWQEEMELYRQKVEPYSDELRQRLA

ARLEALKENGGARLAEYHAKATEHLSTLSEKAKPALEDLRQGLLPVLESF

KVSFLSALEEYTKKLNTQ

Deletion of helices 5 and 6 was performed in a similar manner, but two separate PCR steps using the following primers were employed in a first reaction (Reaction 1, Primer C: 5'-CAGAATTCGCTAGCCGAGTACCACGC-CAA-3', SEQ ID NO:24; and Primer D: 5'-GCAAGCTTAT-TACTGGGTGTTGAGCTTCTT-3', SEQ ID NO:25) and a second reaction (Reaction 2, Primer E: 5'-ATAC-CATGGGCCATCATCATCATCATCATA-3', SEQ ID NO:26; and Primer F: 5'-CAGAATTCGCTAGCCTG-GCGCTCAACTTCTCTT-3', SEQ ID NO:27.

The PCR products encode the N- and C-terminal portions of MSP both lacking helices 5 and 6 and each contain a NheI restriction site. After digestion of the PCR products with NheI, NcoI and HindIII, the fragments was ligated into NcoI+HindIII treated pET 28 to produce the DNA sequence of MSP1Db See FIGS. 9A–9B.

TABLE 13

MSP1Db DNA sequence.

(SEQ ID NO:28)
TATA<u>CC<b>ATG</b>G</u>GCCATCATCATCATCATCATATAGAAGGAAGACTAAAGCT

CCTTGACAACTGGGACAGCGTGACCTCCACCTTCAGCAAGCTGCGCGAAC

AGCTCGGCCCTGTGACCCAGGAGTTCTGGGATAACCTGGAAAAGGAGACA

GAGGGCCTGAGGCAGGAGATGAGCAAGGATCTGGAGGAGGTGAAGGCCAA

GGTGCAGCCCTACCTGGACGACTTCCAGAAGAAGTGGCAGGAGGAGATGG

AGCTCTACCGCCAGAAGGTGGAGCCGCTGCGCGCAGAGCTCCAAGAGGGC

GCGCGCCAGAAGCTGCACGAGCTGCAAGAGAAGTTGAGCGCCAGGCTAGC

CGAGTACCACGCCAAGGCCACCGAGCATCTGAGCACGCTCAGCGAGAAGG

CCAAACCCGCGCTCGAGGACCTCCGCCAAGGCCTGCTGCCCGTGCTGGAG

AGCTTCAAGGTCAGCTTCCTGAGCGCTCTCGAGGAGTACACTAAGAAGCT

CAACACCCAG<b>TAA</b><u>AAGCTT</u>GC

Translation start and stop codons are shown in bold type, and restriction endonuclease recognition sites used in cloning are underlined.

TABLE 14

MSP1Db amino acid sequence.

(SEQ ID NO:29)
MGHHHHHHIEGRLKLLDNWDSVTSTFSKLREQLGPVTQEFWDNLEKETEG

LRQEMSKDLEEVKAKVQPYLDDFQKKWQEEMELYRQKVEPLRAELQEGAR

QKLHELQEKLSARLAEYHAKATEHLSTLSEKAKPALEDLRQGLLPVLESF

KVSFLSALEEYTKKLNTQ

Example 2

Construction of Synthetic MSP Gene

A synthetic gene for MSP1 is made using the following overlapping synthetic oligonucleotides which are filled in using PCR. The codon usage has been optimized for expression in *E. coli*, and restriction sites have been introduced for further genetic manipulations of the gene.

Synthetic nucleotide taps1a
(SEQ ID NO:30)
TACCATGGGTCATCATCATCATCATCACATTGAGGGACGTCTGAAGCTGT
TGGACAATTGGGACTCTGTTACGTCTA Synthetic nucleotide taps2a
(SEQ ID NO:31)
AGGAATTCTGGGACAACCTGGAAAAAGAAACCGAGGGACTGCGTCAGGAA
ATGTCCAAAGAT -continued Synthetic nucleotide taps3a (SEQ ID NO:32)
TATCTAGATGACTTTCAGAAAAAATGGCAGGAAGAGATGGAATTATATCG
TCAA Synthetic nucleotide taps4a (SEQ ID NO:33)
ATGAGCTCCAAGAGAAGCTCAGCCCATTAGGCGAAGAAATGCGCGATCGC
GCCCGTGCACATGTTGATGCACT Synthetic nucleotide taps5a (SEQ ID NO:34)
GTCTCGAGGCGCTGAAAGAAAACGGGGGTGCCCGCTTGGCTGAGTACCAC
GCGAAAGCGACAGAA Synthetic nucleotide taps6a (SEQ ID NO:35)
GAAGATCTACGCCAGGGCTTATTGCCTGTTCTTGAGAGCTTTAAAGTCAG
TTTTCT Synthetic nucleotide taps1b (SEQ ID NO:36)
CAGAATTCCTGCGTCACGGGGCCCAGTTGTTCGCGAAGTTTACTGAAGGT
AGACGTAACAG Synthetic nucleotide taps2b (SEQ ID NO:37)
TCATCTAGATATGGCTGAACCTTGGCCTTCACCTCTTCTAAATCTTTGGA
CATTT Synthetic nucleotide taps3b (SEQ ID NO:38)
TGGAGCTCATGGAGTTTTTGGCGTGCCCCCTCTTGCAGTTCCGCACGCAG
CGGTTCCACCTTTTGACGATATAATTCCAT Synthetic nucleotide taps4b (SEQ ID NO:39)
GCCTCGAGACGTGCGGCCAAACGCTGGCGAAGTTCATCCGAATACGGCGC
CAAATGAGTCCGGAGTGCATCAACAT Synthetic nucleotide taps5b (SEQ ID NO:40)
GTAGATCTTCCAGCGCCGGTTTCGCTTTTTCGCTCAAGGTGCTCAGGTGT
TCTGTCGCTTT Synthetic nucleotide taps6b (SEQ ID NO:41)
CCAAGCTTATTACTGGGTATTCAGCTTTTTAGTATATTCTTCCAGAGCTG
ACAGAAAACTGACTTT

TABLE 15

Full synthetic gene sequence for MSP1.

(SEQ ID NO:42)
ACCATGGGTCATCATCATCATCATCACATTGAGGGACGTCTGAAGCTGTT

GGACAATTGGGACTCTGTTACGTCTACCTTCAGTAAACTTCGCGAACAAC

TGGGCCCCGTGACGCAGGAATTCTGGGACAACCTGGAAAAAGAAACCGAG

GGACTGCGTCAGGAAATGTCCAAAGATTTAGAAGAGGTGAAGGCCAAGGT

TCAGCCATATCTAGATGACTTTCAGAAAAAATGGCAGGAAGAGATGGAAT

TATATCGTCAAAAGGTGGAACCGCTGCGTGCGGAACTGCAAGAGGGGCA

CGCCAAAAACTCCATGAGCTCCAAGAGAAGCTCAGCCCATTAGGCGAAGA

AATGCGCGATCGCGCCCGTGCACATGTTGATGCACTCCGGACTCATTTGG

CGCCGTATTCGGATGAACTTCGCCAGCGTTTGGCCGCACGTCTCGAGGCG

CTGAAAGAAAACGGGGGTGCCCGCTTGGCTGAGTACCACGCGAAAGCGAC

AGAACACCTGAGCACCTTGAGCGAAAAAGCGAAACCGGCGCTGGAAGATC

TABLE 15-continued

Full synthetic gene sequence for MSP1.

TACGCCAGGGCTTATTGCCTGTTCTTGAGAGCTTTAAAGTCAGTTTTCTG

TCAGCTCTGGAAGAATATACTAAAAAGCTGAATACCCAGTAA<u>AAGCTT</u>G

G

Restriction sites used in cloning are underlined, and the translation start and stop signals are shown in bold.

The following is the amino acid sequence of a MSP polypeptide in which half repeats are deleted:

TABLE 16

MSP1D3.

(SEQ ID NO:43)
MGHHHHHHIEGRLKLLDNWDSVTSTFSKLREQLGPVTQEFWDNLEKETEG

LRQEMSPYLDDFQKKWQEEMELYRQKVEPLRAAELQEGARQKLHELQEKL

SPLGEEMRDRARAHVDALRTHLAPYSDELRQRLAARLEALKENGGARLAE

YHAKATEHLSTLSEKAKPALEDLRQGLLPVLESFKVSFLSALEEYTKKLN

TQ

TABLE 17

MSP1D9.

(SEQ ID NO:44)
MGHHHHHHIEGRLKLLDNWDSVTSTFSKLREQLGPVTQEFWDNLEKETEG

LRQEMSKDLEEVKAKVQPYLDDFQKKWQEEMELYRQKVEPLRAELQEGAR

QKLHELQEKLSPLGEEMRDRARAHVDALRTHLAPYSDELRQRLAARLEAL

KENGGARLAEYHAKATEHLSTLSEKAKPVLESFKVSFLSALEEYTKKLNT

Q

TABLE 18

MSP tandem repeat with first half-repeats deleted (MSP2delta1)

(SEQ ID NO:45)
MGHHHHHHIEGRLKLLDNWDSVTSTFSKLREQLGPVTQEFWDNLEKETEG

LRQEMSPYLDDFQKKWQEEMELYRQKVEPLRAELQEGARQKLHELQEKLS

PLGEEMRDRARAHVDALRTHLAPYSDELRQRLAARLEALKENGGARLAEY

HAKATEHLSTLSEKAKPALEDLRQGLLPVLESFKVSFLSALEEYTKKLNT

QGTLKLLDNWDSVTSTFSKLREQLGPVTQEFWDNLEKETEGLRQEMSPYL

DDFQKKWQEEMELYRQKVEPLRAELQEGARQKLHELQEKLSPLGEEMRDR

ARAHVDALRTHLAPYSDELRQRLAARLEALKENGGARLAEYHAKATEHLS

TLSEKAKPALEDLRQGLLPVLESFKVSFLSALEEYTKKLNTQ

With reference to the following protein and DNA sequences, the MSPs we have utilized can be summarized as the following linked structures. Note H1, H2 refer to the sequences of Helix #1 etc. His is a (His)6 tag, TEV is the tobacco viral protease, X is the factor ten protease site.

TABLE 19

Amino Acid Sequences of MSP Building Blocks

| | | |
|---|---|---|
| GLOB | DEPPQSPWDRVKDLATVYVDVLKDSGRDYVSQFEGSALGKQLN | (SEQ ID NO:89) |
| HisX | MGHHHHHHIEGR | (SEQ ID NO:47) |
| HisTEV | MGHHHHHHHDYDIPTTENLYFQG | (SEQ ID NO:48) |
| Helix 1 (H1): | LKLLDNWDSVTSTFSKLREQLG | (SEQ ID NO:49) |
| Helix 2 (H2): | PVTQEFWDNLEKETEGLRQEMS | (SEQ ID NO:50) |
| Helix 3 (H3): | KDLEEVKAKVQ | (SEQ ID NO:51) |
| Helix 4 (H4): | PYLDDFQKKWQEEMELYRQKVE | (SEQ ID NO:52) |
| Helix 5 (H5): | PLRAELQEGARQKLHELQEKLS | (SEQ ID NO:53) |
| Helix 6 (H6): | PLGEEMRDRARAHVDALRTHLA | (SEQ ID NO:54) |
| Helix 7 (H7): | PYSDELRQRLAARLEALKENGG | (SEQ ID NO:55) |
| Helix 8 (H8): | ARLAEYHAKATEHLSTLSEKAK | (SEQ ID NO:56) |
| Helix 9 (H9): | PALEDLRQGLL | (SEQ ID NO:57) |
| Helix 10(H10): | PVLESFKVSFLSALEEYTKKLNTQ | (SEQ ID NO:58) |
| Helix 0.5 (H0.5): | STFSKLREQLG | (SEQ ID NO:59) |
| Helix 10.5(H10.5): | SALEEYTKKLNTQ | (SEQ ID NO:87) |

TABLE 20

Sequences encoding the MSP Building Blocks of TABLE 19.

| | | |
|---|---|---|
| HisX | ATGGGTCATCATCATCATCATCACATTGAGGGACGT | (SEQ ID NO:60) |
| HisTEV | ATGGGTCATCATCATCATCATCATCACGATTATGATATTCCTACTACT GAGAATTTGTATTTTCAGGGT | (SEQ ID NO:61) |
| Helix 1 (H1): | CTGAAGCTGTTGGACAATTGGGACTCTGTTACGTCTACCTTCAGTAA ACTTCGCGAACAACTGGGC | (SEQ ID NO:62) |
| Helix 2 (H2): | CCCGTGACGCAGGAATTCTGGGACAACCTGGAAAAAGAAACCGAGG GACTGCGTCAGGAAATGTCC | (SEQ ID NO:63) |
| Helix 3 (H3): | AAAGATTTAGAAGAGGTGAAGGCCAAGGTTCAG | (SEQ ID NO:64) |
| Helix 4 (H4): | CCATATCTCGATGACTTTCAGAAAAAATGGCAGGAAGAGATGGAATT ATATCGTCAAAAGGTGGAA | (SEQ ID NO:65) |
| Helix 5 (H5): | CCGCTGCGTGCGGAACTGCAAGAGGGGCACGCCAAAAACTCCATG AGCTCCAAGAGAAGCTCAGC | (SEQ ID NO:66) |
| Helix 6 (H6): | CCATTAGGCGAAGAAATGCGCGATCGCGCCCGTGCACATGTTGATGC ACTCCGGACTCATTTGGCG | (SEQ ID NO:67) |
| Helix 7(H7): | CCGTATTCGGATGAACTTCGCCAGCGTTTGGCCGCACGTCTCGAGGC GCTGAAAGAAAACGGGGGT | (SEQ ID NO:68) |
| Helix 8 (H8): | GCCCGCTTGGCTGAGTACCACGCGAAAGCGACAGAACACCTGAGCAC CTTGAGCGAAAAAGCGAAA | (SEQ ID NO:69) |
| Helix 9(H9): | CCGGCGCTGGAAGATCTACGCCAGGGCTTATTG | (SEQ ID NO:70) |
| Helix 10(H10): | CCTGTTCTTGAGAGCTTTAAAGTCAGTTTTCTGTCAGCTCTGGAAGAA TATACTAAAAAGCTGAATACCCAG | (SEQ ID NO:71) |
| Helix 0.5 (H0.5): | TCTACCTTCAGTAAACTTCGCGAACAACTGGGC | (SEQ ID NO:72) |
| Helix 10.5 (H10.5): | CAGTTTTCTGTCAGCTCTGGAAGAATATACTAAAAAGCTGAATACCCAG | (SEQ ID NO:88) |

Several particular MSP sequences useful in the present invention are the following combinations of the above sequences, as given in Table 21.

TABLE 21

Engineered MSPs Useful in Nanodisc Preparation.

| | | |
|---|---|---|
| MSP1 | HisX-H1-H2-H3-H4-H5-H6-H7-H8-H9-H10 | (SEQ ID NO:6) |
| MSP1E1 | HisX-H1-H2-H3-H4-H4-H5-H6-H7-H8-H9-H10 | (SEQ ID NO:73) |
| MSP1E2 | HisX-H1-H2-H3-H4-H4-H5-H5-H6-H7-H8-H9-H10 | (SEQ ID NO:74) |
| MSP1E3 | HisX-H1-H2-H3-H4-H4-H5-H6-H5-H6-H7-H8-H9-H10 | (SEQ ID NO:75) |
| MSP1TEV | HisTev-H1-H2-H3-H4-H5-H6-H7-H8-H9-H10 | (SEQ ID NO:76) |
| MSP1NH | H1-H2-H13-H4-H5-H6-H7-H8-H9-H10 | (SEQ ID NO:77) |
| MSP1T2 | HisTev-H1/2-H2-H3-H4-H5-H6-H7-H8-H9-H10 | (SEQ ID NO:78) |
| MSP1T2NH | H1/2-H2-H3-H4-H5-H6-H7-H8-H9-H10 | (SEQ ID NO:79) |
| MSP1T3 | HisTev-H2-H3-H4-H5-H6-H7-H8-H9-H10 | (SEQ ID NO:80) |
| MSP1D3 | HisX-H1-H2-H4-H5-H6-H7-H8-H9-H10 | (SEQ ID NO:43) |
| MSP1D9 | HisX-H1-H2-H3-H4-H5-H6-H7-H8-H10 | (SEQ ID NO:44) |
| MSP1D5D6 | HisX-H1-H2-H3-H4-H7-H8-H9-H10 | (SEQ ID NO:23) |
| MSP1D4D5 | HisX-H1-H2-H3-H6-H7-H8-H9-H10 | (SEQ ID NO:81) |
| MSP1D6D7 | HisX-H1-H2-H3-H4-H5-H8-H9-H10 | (SEQ ID NO:82) |
| MSP1D3D9 | HisX-H1-H2-H4-H5-H6-H7-H8-H10 | (SEQ ID NO:83) |
| MSP1D10.5 | HisX-H1-H2-H3-H4-H5-H6-H7-H8-H9-H10.5 | (SEQ ID NO:84) |
| MSP1D3D10.5 | HisX-H1-H2-H4-H5-H6-H7-H8-H9-H10.5 | (SEQ ID NO:85) |

In addition to these sequences, there are two fusion protein constructs of reference. These are composed of two MSP1 constructs linked by a Gly-Ser linker:
MSP2 (MSP1-Gly-Thr-MSP1, SEQ ID NO:17) and
MSP2D1D1 (MSP1T3-Gly-Thr-H2-H3H4-H5-H6-H7-H8-H9-H10, SEQ ID NO:86).

Other constructs that can be readily produced include permutations of the above, i.e. MSP1 or MSP2 or MSP2a with any combination of the following: hinge deletion, hinge replacement, half-repeat deletion, histidine tag, different linkers for MSP2 analogs.

Example 3

Expression of Recombinant MSPs

To express MSP proteins, the nucleic acid constructs were inserted between the NcoI and HindIII sites in the pET28 expression vector and transformed into *E. coli* BL21(DE3). Transformants were grown on LB plates using kanamycin for selection. Colonies were used to inoculate 5 ml starter cultures grown in LB broth containing 30 µg/ml kanamycin. For overexpression, cultures were inoculated by adding 1 volume overnight culture to 100 volumes LB broth containing 30 µg/ml kanamycin and grown in shaker flasks at 37° C. When the optical density at 600 nm reached 0.6–0.8, isopropyl-β-D-thiogalactopyranoside (IPTG) was added to a concentration of 1 mM to induce expression and cells were grown 3–4 hours longer before harvesting by centrifugation. Cell pellets were flash frozen and stored at −80° C.

Example 4

Purification of Recombinant MSPs

Purification of histidine-tagged MSPs was carried out as follows. A frozen cell pellet from 1 liter of expression culture was resuspended in 25 milliliters of 20 mM Tris HCl pH 7.5 containing 1 mM phenylmethylsulfonyl fluoride. Triton X-100 (t-octylphenoxypolyethoxyethanol) was added from a 10% (w/v) stock in distilled H20 to a final concentration of 1%. The resuspended cells were sonicated on ice at 50% duty cycle at a power setting of 5 for four cycles of 1 minute on, 5 minutes off with a Branson probe sonifier. The resulting lysate was centrifuged for 30 minutes at 30,000 rpm in a Beckman Ti 45 rotor in a ultracentrifuge. The resulting supernatant was filtered through a 0.22 µm nylon syringe filter. The salt concentration was adjusted to 0.5 M from a 4 M NaCl stock in water and applied to a 5 ml Hi-Trap nickel loaded column (Pharmacia, Piscataway, N.J.).

For His-tagged-MSP1, the column is washed with 20 ml buffer (10 mM Tris pH 8, 0.5 M NaCl) containing 1% Triton X-100, followed by 20 ml buffer+50 mM sodium cholate, and then 20 ml buffer and 20 ml 100 mM imidazole in buffer. The His-tagged polypeptide is eluted with 15 ml 0.5 M imidazole in buffer.

For His-tagged-MSP2, the column is washed with 20 ml buffer (10 mM Tris pH 8, 0.5 M NaCl) containing 1% Triton X-100; 20 ml buffer+50 mM cholate; 20 ml buffer; 20 ml 35 mM imidazole in buffer. The His-tagged polypeptide is then eluted with 15 ml 0.5 M imidazole in buffer, and the purified protein is dialyzed against 10 mM Tris pH 8, 0.15 M NaCl using a 10,000 MW cutoff cellulose dialysis membrane.

Example 5

Production of MSP-Containing Nanoscale Particles

To reconstitute MSP proteins of the present invention with lipid, purified MSP was concentrated in a pressurized ultrafiltration device (Amicon) using a 10,000 MW cutoff filter to ~2–6 mg protein/ml. Concentration of protein was determined by bicinchonic acid assay (Pierce Chemical, Rockford, Ill.) or measurement of A280 using theoretical absorption coefficient. Phospholipid (dipalmitoyl phosphatidylcholine in this case, however different phosphatidylcholines and mixtures of phosphatidylcholine and other lipids can be used) in chloroform stock solution was dried under a stream of nitrogen and placed in vacuo overnight. Phosphate analysis was performed to determine the concentration of chloroform stock solutions. The dried lipid film was resuspended in buffer 10 mM Tris HCl pH 8.0 or pH 7.5 containing 0.15 M NaCl and 50 mM sodium cholate to give a final lipid concentration of 25 mM. The suspension was vortexed and heated to 50° C. to obtain a clear solution. Phospholipid solution was added to solution of MSP (2–6 mg/ml protein) to give molar ratios for MSP1:lipid of 2:200 and for MSP2 of 1:200. The mixture was incubated overnight at 37° C. and then dialyzed against 1000 volumes of buffer without cholate with 4 changes of buffer over 2–3 days.

Example 6

Tethered Membrane Protein Incorporation

Tissue Factor (TF) is a representative tethered membrane protein. In order to demonstrate the value of MSP technology for a tethered membrane protein, recombinant human TF was incorporated into MSP-supported Nanodiscs. The recombinant protein consists of an extracellular domain, the transmembrane anchor and a truncated cytosolic domain. The truncation increases the homogeneity of the protein by removing the C-terminal portions of the protein which are subject to proteolysis by bacterial enzymes. This modification does not affect TF activity. Additional modifications to the protein include an N-terminal trafficking peptide and an HPC4 epitope tag. The trafficking peptide directs the expressed protein to the intermembrane space of the recombinant E. coli host cell, in which space the peptide sequence is cleaved. The HPC4 epitope allows for affinity purification with $Ca^{2+}$ dependent antibody (Rezaie et al., 1992) and does not affect TF activity.

A 25 mM lipid mixture containing 80% phosphatidyl choline and 20% phosphatidyl serine was solubilized with 50 mM cholate in 10 mM Tris Cl, 150 mM NaCl at pH 8.0. TF, MSP1 and lipid (in a ratio of 1:10:1000) were combined and incubated overnight at 37° C. The sample was then dialyzed at 37° C. (10,000 dalton molecular weight cutoff membrane) against buffer containing 10 mM Tris Cl, 150 mM NaCl at pH 8.0 (lacking cholate) for 2 hours. Dialysis was then continued at 4° C. for an additional 6 hours with buffer changes every 2 hours. The approximately 1 ml sample was then concentrated to <250 µl using a YM-10 centrifuge concentrator and injected into a Pharmacia 10/30 Superdex 200 HR gel filtration column. Samples were eluted with buffer identical to that described above (no cholate) at 0.5 ml per minute. Fractions from chromatography were run on an 8–25% gradient SDS polyacrylamide gel to determine apparent size and then checked for coagulation activity. The chromatogram showing elution of TF incorporated into an excess population of MSP1 Nanodiscs is shown in FIGS. 16A–16B.

The activity of TF in several disk fractions was determined by coagulation assays with human serum. Activity was monitored in fractions 25–28 as the inverse of coagulation time. Activity was highest in fraction 25 at 40 $hr^{-1}$ and decreased through fraction 28 at 30 $hr^{-1}$. This is expected from the size chromatogram in that the leading edge of the Nanodisc peak has a larger effective mass due to the incorporation of TF in the MSP-supported bilayer. This assay thus demonstrates that TF is incorporated into Nanodiscs in an active conformation and that the membrane environment of the Nanodisc closely mimics that of the native membrane system.

Cytochrome b5 is a membrane anchored heme protein having a single membrane anchor domain that penetrates the membrane bilayer. Cytochrome b5 solubilized from its native membrane exists as large aggregates in the absence of detergent and appears as a smear rather than a discrete band on native polyacrylamide gel electrophoresis. Formation of Nanodiscs through a self-assembly process wherein cytochrome b5 is added to the preparation of MSP and phospholipid results in the incorporation of cytochrome b5 into Nanodisc structures. This is verified by the intense heme staining of the band corresponding to Nanodiscs. The data show that cytochrome b5 can be successfully solubilized using MSP technology and that disc complexes containing cytochrome b5 can be chromatographically separated and purified away from the undesired aggregated material. The optical absorption properties of the heme chromophore of the purified material demonstrate that the heme active site in a native conformation.

Nanodiscs can also be formed by mixing 20 µl of apo A-I (10 mg/ml), 6.6 µl cytochrome b5 (0.5 mM) and 50 µl egg phosphatidylcholine/sodium cholate (11.2 egg PC, 6.2 mg/ml sodium cholate), incubating overnight at 4° C., followed by dialysis to remove cholate. Purification was accomplished using a Pharmacia MonoQ FPLC anion exchange column equilibrated in 25 mM Tris Cl, pH 8.0. A linear gradient was run at 0.5 ml/min from 0–1 M NaCl in 20 min.

As an alternative to incorporating tethered membrane proteins into Nanodiscs from solubilized, purified proteins, the tethered membrane proteins can be incorporated into Nanodiscs with MSPs using membrane or membrane fragment preparations containing those tethered membrane proteins of interest.

Example 7

Embedded Membrane Protein Incorporation

Cytochrome P450 2B4 from rabbit liver microsomes, cytochrome P450 3A4 found in nature in human liver microsomes and cytochrome P450 6B1 from insect microsomes are representative of embedded membrane proteins.

Cytochrome P450 2B4 was isolated from rabbit liver microsomes after induction with phenobarbital. Formation of 2B4 Nanodiscs is as follows. Cytochrome P450 2B4 was reconstituted into disks by the detergent dialysis method. The buffer consisted of 10 mM Tris-HCl pH 8.0, 0.1 M NaCl, 10% (v/v) glycerol. The mixture of apo A-I, cholate and phospholipid (1:220:110 mole ratio) was incubated for 8 hours at 37° C. followed by addition of P450 (1:0.5, apo A-I:P450 mole ratio) and incubation overnight at room temperature. The mixture was dialyzed using a 10,000 MW cutoff slide-a-lyzer (Pierce Chemical Co., Rockford, Ill.) at room temperature for two hours followed by a change of buffer and continued dialysis at 4° C. It was found that 82% of the P450 content could be recovered under these conditions. After dialysis, the mixture was injected onto a Superdex 200 HR10/30 gel filtration column (Pharmacia, Uppsala, SE) equilibrated in reconstitution buffer at room temperature at a flow rate of 0.25 ml/minute with collection of 0.5 ml fractions. Fractions were assayed using native polyacrylamide gradient gel electrophoresis on 8–25% gradient native gels and Coomassie staining using the Phastgel system (Pharmacia, Uppsala, Sweden).

Human cytochrome P450 3A4, normally from liver microsomes, has also been cloned, expressed in *E. coli*, purified and incorporated into MSP-supported bilayer Nanodiscs. Ten nanomoles of MSP2, one micromole of lipid, five nanomoles of cytochrome P450 3A4 protein and two micromoles cholic acid were incubated together at 37° C. for 2 hours. The incubated mixture was then dialyzed in a 10K Slide-A-lyzer Dialysis Cassette (Pierce Chemical Co., Rockford, Ill.). The dialysis was carried out with 10 mM potassium phosphate (pH 7.4) 150 mM NaCl buffer. The sample was dialyzed at 37° C. for 6 hours followed by a buffer change, and dialysis continued at 4° C. with two buffer changes at 12 hour intervals. The samples were then fractionated on a Superdex 200 HR 10/30 column (Pharmacia, Uppsala, SE) equilibrated in dialysis buffer at room temperature at a flow rate of 0.5 ml/min.

Cytochrome P450 6B1 is another model embedded membrane protein; it has been isolated from Papilio polyxenes, the black swallowtail. These butterflies feed exclusively on plants producing furanocoumarins, plant metabolites that are phototoxic to most organisms. Cytochrome 6B1 catalyzes the detoxification of furanocoumarins.

In order to show the utility of the MSP methodology of the present invention, we demonstrated that isolated membranes containing their repertoire of membrane proteins and natural lipids could be used as a source for incorporating membrane proteins into Nanodiscs. An important illustrative embodiment is the use of the common insect cell (Sf9)-baculovirus expression system which is used widely as a heterologous expression system. Thus, we used an insect cell line co-infected such that a microsomal preparation containing overexpressed insect CYP6B1 and also overexpressed insect NADPH cytochrome P450 reductase. In these experiments we not only demonstrate that MSP Nanodiscs can be used to incorporate another cytochrome P450 system into soluble monodisperse particles but also that the source of this P450 could be simply whole membranes containing this protein.

A standard baculovirus expression system was used to obtain microsomal preparations with overexpressed insect cytochrome CYP6B1 and insect NADPH P450 reductase. Construction of the recombinant CYP6B1 baculovirus expression vector and infection of *Spodoptera frugiperda* (Sf9) was performed as previously described (Chen et al., 2002). Typically, 32 plates containing $6 \times 10^7$ baculovirus-infected cells each (MOI of 2) were collected 72 hours post-infection. Microsomal membranes were homogenized in 2 ml grinding buffer (pH 7.8) composed of 0.1 M sodium phosphate buffer (pH 7.8), 1.1 mM EDTA, 20% glycerol, 0.5 mM PMSF, 0,1 mM DTT, and 5 μg/ml (w/v) leupeptin. Membranes were frozen in liquid nitrogen and stored at −80° C.

To assemble Nanodiscs comprising CYP6B1 from the microsomal membrane preparation, the protein concentration of the membranes was determined using a BCA™ protein assay kit from Pierce (Rockford, Ill.). We assumed a 1:1 mass relationship of protein: lipid in the membranes and an average molecular weight of phospholipids of 750 grams/mole. The membranes were detergent solubilized with 0.5 M cholic acid and mixed with MSP in the approximate ratio of 1:25:50 to 1:500:1000, preferably 1:75:150, for MSP:lipid:detergent. Typically, reconstitution samples include approximately 100 nmol scaffold protein, 10 μmol lipid, and 20 μmol cholate and were pre-incubated for 1.5 hours at 4° C. The temperature chosen is higher than the phase transition temperature for the lipids. Detergent was removed by incubating with Biobeads® SM-2 Adsorbent from BioRad Laboratories (Hercules, Calif.) (0.4 grams Biobeads per 1 ml of reconstitution mixture) for 1.5 hours at 4° C. followed by centrifugation at 11,750×g for 5 minutes. His6-tagged MSP particles were purified by incubating with 1 ml of Ni-NTA agarose from QIAGEN, Inc. (Valencia, Calif.) per 7.5 grams of His6-tagged MSP for 1 hour at 4° C., followed by centrifugation at 11,750×g for 5 minutes. MSP particles bound to the Ni-NTA agarose were washed with three sequential resin volumes of 0.1 M sodium phosphate buffer (pH 7.4) containing 0.3 M NaCl, 0.15 M NaCl, and no NaCl, respectively. To maintain the integrity of the CYP6B1 protein, MSP particles were eluted with 0.1 M sodium phosphate buffer (pH 7.4) containing 0.25 M EDTA (to chelate trace metal ions) rather than the 50 mM imidazole used in previous MSP purifications.

Figure 9:
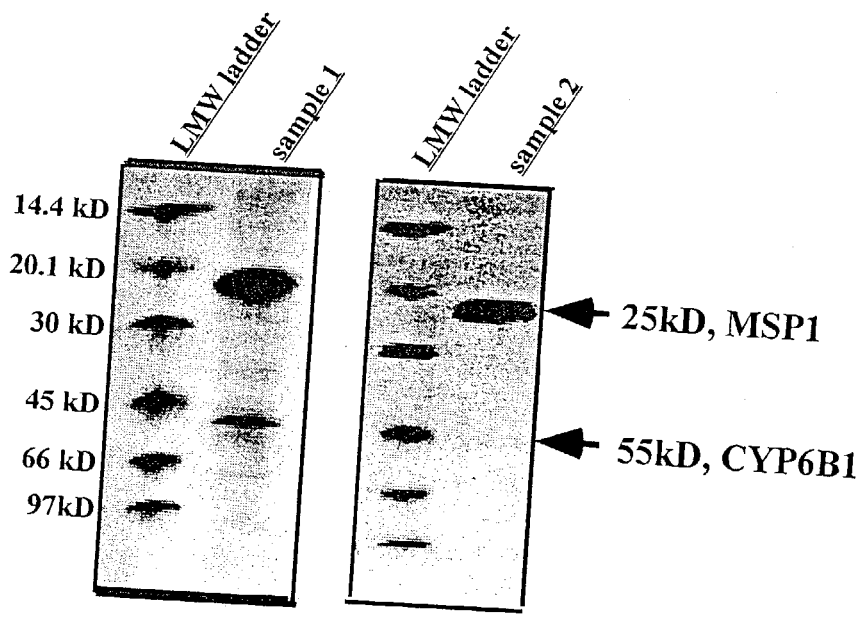
FIG. 9 illustrates the results of PAGE with sample 1 (Nanodiscs prepared with microsomal membranes from cells coexpressing cytochrome P450 6B1 and NADPH P450 reductase). Sample 2 contains control microsomes.
Figure 10:
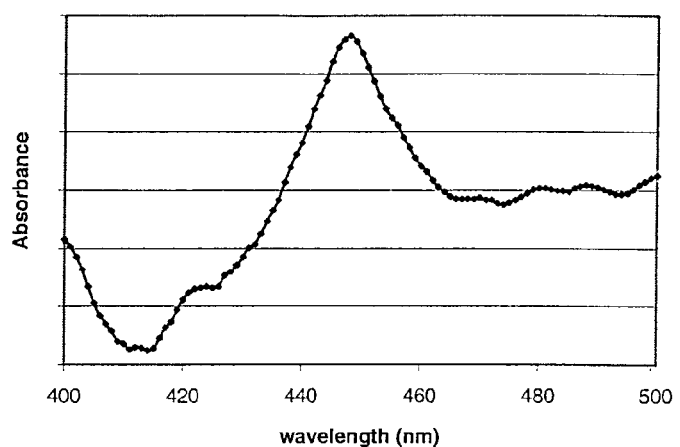
FIG. 10 provides a characteristic optical spectrum of active cytochrome P450 6B1 incorporated within Nanodiscs; the characteristic peak is at 450 nm. Such spectra indicate a correct thiolate heme ligation and no evidence for the presence of an inactive "P420" form of the cytochrome in the solubilized membrane bilayer system.
Figure 11:
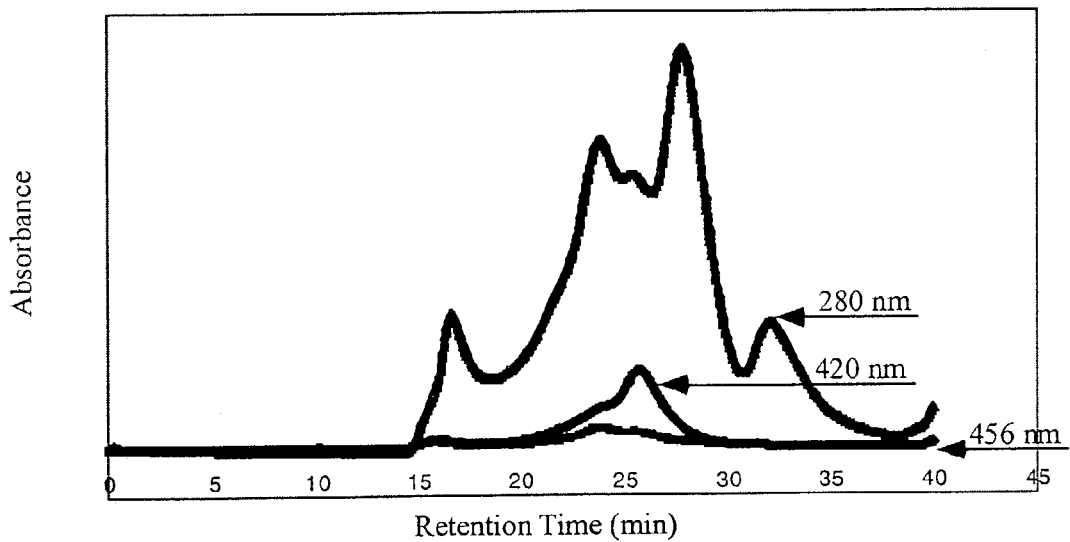
FIG. 11 depicts a chromatogram of sample separated by a Superdex sizing column. Retention times indicated rHDL particles 10 nm in size.
Figure 12:
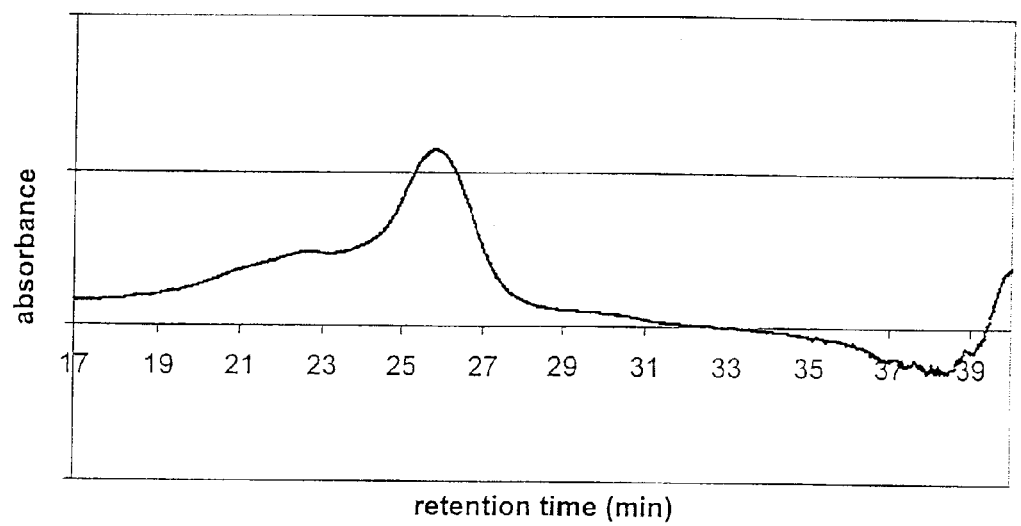
FIG. 12 illustrates co-incorporation of cytochrome P450 reductase and cytochrome P450 6B1 in MSP Nanodiscs. The ratio of absorbances at 456 nm (predominantly reductase) to that at 420 nm (predominantly P450) is plotted as a function of retention time. The peak at about 26 min indicates a Nanodisc population containing both reductase and cytochrome.

Based on the lipid concentration contained in the microsomal preparations, MSP technology was used to assemble microsomal proteins into nanoparticle discs using a ratio of 110:1:220 lipid:MSP1:cholate. The microsomal sample was detergent solubilized with cholate and mixed with MSP1. The sample was incubated at 4° C. for 2 hours. The detergent can be removed by dialysis or hydrophobic beads. In this experiment Biobeads (hydrophobic beads, trademark of BioRad, Hercules, Calif.) were added in excess (0.25 g per 1 ml disc mixture) and incubated for 2 hours at 4° C. for 2 hours to remove detergent. The sample was removed from the beads and the His6-tagged MSP was isolated by using a batch purification method with $Ni^{2+}$ resin. The MSP disks were then isolated by Superdex sizing column chromatography (FIG. 9). Incorporation of P450 into the $His_6$-tagged discs was followed by CO difference spectroscopy of nickel affinity column purified and sizing column-purified fractions (FIG. 10). SDS-PAGE was performed using 8–25% gradient gels stained with Coomassie blue to verify incorporation of cytochrome P450 6B1 into discs (FIG. 10).

The endogenous (natural) ratio of cytochrome P450 to reductase is about 10–20. To obtain activity of the cytochrome P450 6B1 after reconstitution into discs, it is preferred that an excess of reductase be added to the reconstitution mixture, such that a P450 molecule and reductase molecule both partition into a single disc. Supplementation of the microsomal preparation with exogenously added reductase has been successfully demonstrated.

Figure 13:
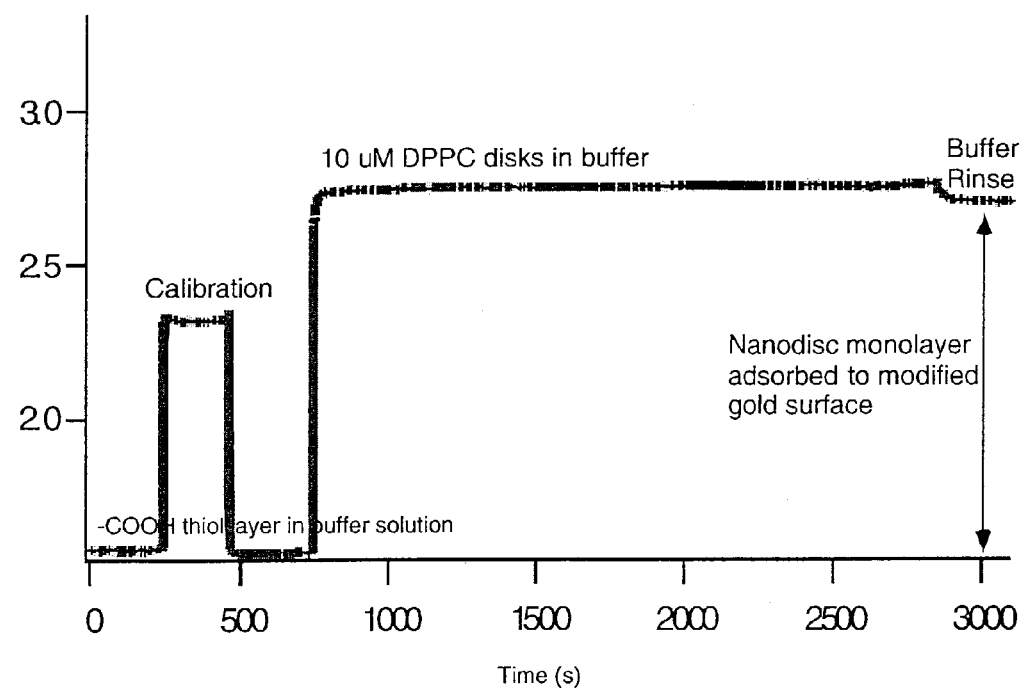
FIG. 13 illustrates the binding of DPPC Nanodiscs containing carboxyl terminated thiols to a gold surface, as monitored by surface plasmon resonance.

The protocol for making discs using microsomal preparations was used with one modification. Exogenous rat reductase was added after the solubilization step of the microsomal preparation with cholate and before the addition of MSP1. Otherwise identical disc assembly and purification procedures were followed. The sample was separated by a Superdex sizing column, where absorbance at 280 nm indicates the presence of MSP1, absorbance at 420 and 456 nm indicates the presence of ferric species, and absorbance at 456 nm also indicates presence of reductase. A ratio plot of 456 to 420 nm was made; it showed positions on the chromatogram where the absorbance at 456 nm was above that associated with cytochrome P450 6B1 and, therefore, could be attributed to absorbance by reductase. Retention times reflected the presence of 10 nm particles containing cytochrome P450 6B1 and reductase (FIG. 13).

MSP-supported Nanodiscs with purified proteins, membrane fragments or disrupted membranes can be used in high throughput screening ventures, for example, to identify new pharmaceuticals and other biologically active molecules.

Example 8

Integral Membrane Protein Incorporation

Bacteriorhodopsin is a model integral membrane protein. Bacteriorhodopsin was incorporated into nanoscale structures using the following procedure, which is a protocol useful for other proteins as well. Bacteriorhodopsin was obtained as lyophilized purple membrane from Sigma (St. Louis, Mo.). 1 mg BR was suspended in 1 ml 25 mM potassium phosphate pH 6.9. 1 ml 90 mM n-octyl B-D-glucopyranoside in the same buffer was added and the sample placed in the dark at 24° C. overnight. This treatment produces a detergent-solubilized monomeric form (Dencher et al., 1982). BR was quantitated assuming a molar extinction coefficient at 550 nm of 63,000. BR (7.8 µM) was mixed with MSP1 (97 mM) or MSP2 (110 mM) and cholate (50 mM) to give final molar ratios of MSP1:BR of 10:1 or MSP2:BR of 5:1 and a cholate concentration of approximately 8 mM. For reconstitution with phospholipid, the lipid is solubilized as above in the presence of 50 mM cholate and mixed with MSP1 at a mole ratio of 1 MSP1:110 lipids:0.1 BR. The mixture was incubated at room temperature for ~3 hours followed by dialysis overnight against 1000 volumes of buffer using 10,000 MW cutoff dialysis devices (Slide-a-lyzer, Pierce Chemical). Dialysis was continued at 4 degrees for 2 days with several changes of buffer. 10 mM HEPES, pH 7.5, 0.15 M NaCl buffer can be used. Tris buffer pH 7.5 or pH 8 has also been used successfully.

The 5-hydroxytryptamine 1A G protein coupled receptor from human has been incorporated into MSP-containing nanoparticles. A commercially available insect cell expression system that provides a membrane fraction containing the human 5-hydroxytryptamine 1A GPCR was supported using MSP compositions. Briefly, the 5-HT receptor containing membrane preparation was mixed with phospholipids (phosphatidyl choline, phosphatidylethanolamine, phosphatidyl serine) at a ratio of 45:45:10, MSP1 and cholate. 5-HT1A receptors overexpressed in a commercially available Sf9 insect cell membrane preparation (Sigma Chemical Co., St. Louis, Mo.) were solubilized using the following protocol. POPC, POPS and POPE (Avanti Phospholipids) in chloroform were mixed in a 45:10:45 mole ratio and dried down under a stream of nitrogen, then placed under vacuum for several hours to remove residual solvent. The phospholipids were dispersed in 50 mM Tris pH 7.4, 0.2 M NaCl, 50 mM sodium cholate buffer at a concentration of 25 mM phospholipid. Five microliters of the Sf9 membrane preparation (0.2 mg/ml protein), 1.62 microliters of phospholipid in buffer, 2.4 microliters of MSP1 (4.2 mg/ml) and 0.28 microliters 4 M NaCl were mixed and left for 1 hour on ice. The mixture was diluted to 100 microliters total volume with 50 mM Tris pH 7.4 and dialyzed in a mini slide-a-lyzer (Pierce Chemical) against 50 mM Tris pH 7.4 at 4° C. (two one-liter changes of buffer). To determine the amount of 5HT1A receptor associated with Nanodiscs, a radiolabeled ligand was bound to the receptor and disk-receptor-ligand complexes were isolated using the 6-histidine tag present in the MSP1 according to the following protocol. After dialysis, the mixture was diluted to 200 microliters total volume with 50 mM Tris pH 7.4. Ninety-five microliters of the diluted mixture were placed into each of two tubes. One hundred five microliters of stock reagent were added to give final concentrations of 50 mM Tris pH 7.4, 10 mM MgSO$_4$, 0.5 mM EDTA, 0.1% ascorbic acid in a final volume of 200 microliters. Tritium-labeled 8-hydroxy-DPAT (specific activity 135000 Ci/mole) was added to each tube to give a concentration of 1.5 nM. As a control, unlabeled metergoline (final concentration 100 micromolar) was added to one of the tubes as a competitive ligand. After 1 hour on ice, the mixture was applied to 200 microliters of Ni-chelating resin to specifically bind receptor associated with His-tagged MSP1 disks. The resin was washed three times with 0.5 ml of cold 50 mM Tris pH 7.4 to remove non-specifically bound ligand. Specifically bound radiolabeled 8-hydroxy-DPAT bound to receptor/disk complexes was eluted with 0.5 ml 0.5 Molar imidazole in 10 mM Tris pH 7.4, 0.5 M NaCl. Scintillation cocktail was mixed with the eluate and specifically bound radioligand was determined by scintillation counting. Between five and fifteen percent of the receptor initially present in the Sf9 membrane was found to bind ligand in receptor associated with MSP1 Nanodiscs.

The particles into which the 5-HT GPCR had incorporated were dialyzed. Functionality (in terms of ligand binding) was tested using dialysis against buffer containing tritiated 8-OH-DPAT, an agonist of this receptor. The particles were then run over a Ni-NTA column to bind via the histidine tag on the MSP1 and to separate the particles from 8-OH-DPAT which had not bound to the particles, and the material bound to the column was then eluted. Association of the tritium labeled agonist was demonstrated, showing that the incorporated GPCR retained its ability to bind agonist.

As discussed above for the tethered membrane proteins, the integral and embedded membrane proteins can be incorporated into Nanodiscs using MSPs and solubilized membrane preparations, rather than purified, solubilized proteins. The naturalistic presentation of the proteins within the Nanodiscs is maintained, regardless of whether the proteins were purified or whether they were directly derived from membrane preparations.

Example 9

Analysis of MSP-Supported Nanodisc Phospholipid Assemblies

The particles resulting from self-assembly of membrane scaffold proteins and phospholipids, either with or without an additional target protein, were analyzed as follows.

Bacteriorhodopsin-containing particles were dialyzed, and the resulting mixture was injected onto a Superdex 200 HR10/30 gel filtration column (Pharmacia) and eluted with buffer at 0.5 ml/min at room temperature. Absorbance was monitored at 280 nm for protein and 550 nm for BR. 0.5 ml fractions were collected. The column was calibrated using a mixture of thyroglobulin (669 kDa, Stoke's diameter 170 A), ferritin (440 kDa, Stoke's diameter 122 A), catalase (232 kDa, Stoke's diameter 92 A), lactate dehydrogenase (140 kDa, Stoke's diameter 82 A), bovine serum albumin (66 kDa, Stoke's diameter 71 A), and horse heart cytochrome c (12.4 kDa, Stoke's diameter 35.6 A).

Atomic Force Microscopy (AFM) was performed with a Digital Instruments Nanoscope IIIa in contact mode with sharpened silicon nitride probes under buffer. MSP1 and MSP2 dipalmitoyl phosphatidylcholine particles were treated with 1:50 Factor Xa:MSP protein by mass in 10 mM Tris pH 8, 0.15 M NaCl, 2 mM $CaCl_2$ for 8 hours. 2–10 ml sample was placed on a freshly cleaved mica surface along with 20 ml imaging buffer (10 mM Tris pH 8, 0.15 M NaCl, 10 mM $MgCl_2$) and incubated for 30 minutes or longer before mounting sample in the fluid cell. Several milliliters of buffer were flushed through the fluid cell to remove unadsorbed material.

Phosphate analysis of the nanoscale particles was carried out as follows. Phosphate assay procedures were adapted from Chen et al. (1956) and Fiske and Subbarow (1925). Samples containing roughly 40 nmoles lipid phosphate were dried down in glass tubes. 75 ml 8.9 N $H_2SO_4$ was added to each tube and heated to 210° C. for 30 minutes. 1 drop 30% $H_2O_2$ was added to each tube and heated for 30 minutes. Tubes were cooled, 0.65 ml $H_2O$ was added followed by 83.3 ml 2.5% w/v ammonium molybdate tetrahydrate followed by vortexing and the addition of 83.3 ml 10% w/v ascorbic acid. After mixing, the tubes were placed in a boiling water bath for 7 minutes. Absorbance was read at 820 nm. Absorbance was calibrated using potassium phosphate standards from 0 to 100 nmol phosphate. Buffer blanks from column chromatography were included for MSP proteins.

Example 10

MSP-Supported Structures on Surfaces

Nanodiscs comprising MSPs and a protein of interest can be assembled onto a gold surface. The utility of this relates to the resulting epitaxial presentation of a target incorporated into a Nanodisc assembly to the solution. This offers an ideal system for quantitating binding of other macromolecules or small molecules tagged with dielectric contrast agents to the target protein. A common methods of accomplishing such measurements uses surface plasmon resonance (SPR) technology. SPR is a common technique used to monitor biomolecular interactions at surfaces. The ability of SPR to rapidly detect and quantitate unlabeled protein interactions on gold surfaces is useful for creating high through put chip assays for diverse membrane proteins (embedded and solubilized) on discs.

Discs consisting of the phospholipid DPPC either with or without an additional thiolated lipid and MSP1 protein were prepared as follows. A 25 mM lipid mixture containing phosphatidylcholine was solubilized with 50 mM cholate in 10 mM Tris Cl, 150 mM NaCl at pH 8.0 were combined and incubated overnight at 37° C. For thiolated discs, 90% phosphatidylcholine and 10% thiolated lipid (ATA-TEG-DSPA, Northern Lipids, Vancouver, BC, CA) was solubilized in 3.3 mM Tris Cl, 66.7 mM borate, 150 mM NaCl at pH 9.0 in order to unmask the thiols in the thiolated lipids. MSP1 and lipid (1:100) were combined and incubated overnight at 37° C. The sample was then dialyzed at 37° C. (10,000 MW cutoff membrane) against buffer containing 10 mM Tris Cl, 150 mM NaCl at pH 8.0 without cholate for 2 hours. Dialysis was then continued at 4° C. for an additional 6 hours with buffer changes every 2 hours. The approximately 1 ml sample was concentrated to <250 µl using a YM-10 centrifuge concentrator and injected onto a Pharmacia 10/30 Superdex 200 HR gel filtration column. Samples were eluted from the column using the stated buffer without cholate at flow rates of 0.5 ml/min. Fractions from chromatography were analyzed by polyacrylamide gel electrophoresis using 8–25% gradient polyacrylamide gel to determine apparent size.

The Nanodisc samples (3–20 µM) prepared as described were injected into an SPR instrument to determine if the discs would bind to the gold surface. Both the DPPC and 10% thiolated lipid discs adsorbed to a gold surface and a modified gold surface covered with a monolayer of methyl terminated thiol (nonanethiol) or carboxyl terminated thiol (11-mercaptoundecanoic acid). Thiolated discs were injected using a buffer consisting of 3.3 mM Tris, 66.7 mM borate, 150 mM NaCl, pH 9.0. DPPC discs were injected using a buffer of 10 mM Tris, 150 mM NaCl, pH 7.5 or pH 8.0. In all cases, the discs could not be removed even under harsh conditions (0.5 M HCl). Surface coverage was shown to increase with increasing concentration of discs injected (3 µM vs. 19 µM). Discs do not form perfectly packed monolayers; accordingly, surface coverage is limited by the jamming limit (theoretical maximum coverage based on random sequential absorption to the surface modeling discs as identical non-overlapping hard spheres) of 0.547. The coverage for a full monolayer of discs was calculated based on an assumption of disc height of 5.5 nm and a refractive index between 1.45 and 1.5. The full monolayer values were multiplied by the jamming limit to determine the maximum coverage that was then used to determine percent coverage based on experimental values. When the disc concentration was at least 10 µM, the estimated coverages were between about 62 and about 103%. The resultant SPR trace demonstrating association of the Nanodiscs to the gold surface is shown in FIG. 14.

Nanodiscs comprising MSPs and a protein of interest can be attached to a solid support via the His tag on the MSP where the support is coated with Ni-NTA or a His tag-specific antibody, commercially available from BD Biosciences Clontech, Palo Alto, Calif., for example, or to Ni-NTA agarose beads, commercially available from Qiagen, Valencia, Calif., for example, or other solid support, including beads, chips, plates and microtiter dishes.

Example 12

General Techniques

For SDS-PAGE, microliter samples were separated on 8–25% gradient polyacrylamide gels (Pharmacia) and stained with Coomassie blue.

Sizing column chromatography purification was carried out as follows. The nickel affinity-purified sample mixture was injected onto a Superdex (Trademark of Pharmacia, Piscataway, N.J.) 200 HR10/30 gel filtration column (Pharmacia) equilibrated in 0.1M sodium phosphate buffer (pH 7.4) at a flow rate of 0.5 ml/min. Fractions containing CYP6B1 were concentrated using a Centricon YM-30 centrifugal filter device (Millipore Corporation, Billerica, Mass.) and re-injected onto the Superdex 200 HR10/30 gel filtration column under the same buffer conditions.

Lipids were extracted by the Folch method (Folch-Pi et al. (1957)), where the sample was homogenized with 2:1 chloroform-methanol (v/v) and washed with ¼ volume 0.88% KCl in water. The solution was mixed vigorously and the phases were completely separated by centrifugation (3,000× g) for 5 minutes. The organic layer was dried using 8 and 5 μg/ml (w/v) leupeptin. Membranes were frozen in liquid nitrogen and stored at −80° C.

Nanodisc assembly is generally carried out as follows. The protein concentration of the membranes was determined using a BCA™ protein assay kit from Pierce (Rockford, Ill.). We assumed a 1:1 mass relationship of protein:lipid in the membranes with an average molecular weight of phospholipids of 750 grams/mole. The membranes were detergent solubilized with 0.5 M cholic acid and mixed with MSP in the approximate ratio of 1:25:50 to 1:500:1000 with 1:75:150 preferable. The membranes were detergent solubilized with 0.5 M cholic acid and mixed with MSP in the approximate ratio of 1:100:200 for MSP:lipid:detergent. Typically, reconstitution samples include approximately 100 nmol membrane scaffold protein, 10 μmol lipid, and 20 μmol cholate and were pre-incubated for 1.5 hours at 4° C. Detergent was removed by incubating with Biobeads® SM-2 Adsorbent from BioRad Laboratories (Hercules, Calif.) (0.4 grams Biobeads per 1 ml of reconstitution mixture) for 1.5 hours at 4° C. followed by centrifugation at 11,750×g for 5 minutes. His6-tagged MSP particles were purified by incubating with 1 ml of Ni-NTA agarose from QIAGEN, Inc. (Valencia, Calif.) per 7.5 grams of His6-tagged MSP for 1 hour at 4° C., followed by centrifugation at 11,750×g for 5 minutes. MSP particles bound to the Ni-NTA agarose were washed with three sequential resin volumes of 0.1 M sodium phosphate buffer (pH 7.4) containing 0.3 M NaCl, 0.15 M NaCl, and no NaCl, respectively. To maintain the integrity of the CYP6B1 protein, MSP particles were eluted with 0.1 M sodium phosphate buffer (pH 7.4) containing 0.25 M EDTA rather than the 50 mM imidazole used in previous MSP purifications.

Thin-Layer Chromatography (TLC) is carried out as follows. Samples were spotted onto preparative silica gel stationary phase TLC plates purchased from EM Science (Hawthorne, N.Y.) alongside phospholipid standards purchased from Avanti (Alabaster, Ala.) and developed using a mobile phase of chloroform/methanol/ammonium hydroxide (65:25:4). TLC plates were exposed to iodine vapor for visualization, scanned using a Hewlett Packard ScanJet, and quantified on a Macintosh computer using the public domain NIH Image program developed at the U.S. National Institutes of Health (available on the internet at the website entitled rsb.info.nih.gov/nih-image/).

Example 13

Substrate Binding

The CYP6B1-containing population of Nanodiscs collected after Superdex size fractionation was concentrated to an enzyme concentration of 50 nM. A microtiter plate was arranged with wells A1–A5 and wells B1–B5 each containing 200 μl Nanodisc samples and wells C1–C5 each containing 200 μl buffer (0.1 M sodium phosphate, pH 7.4). To rows A and C, a 20 mM stock concentration of xanthotoxin (Sigma Chemical Co.) in methanol was added to yield final concentrations of 0 μM (column 1), 10 μM (column 2), 20 μM (column 3), 50 μM (column 4), and 150 μM (column 5). This dilution was such that the total organic solvent content did not exceed 1% when added to the Nanodisc samples. To row B, 0 μl, 0.1 μl, 0.2 μl, 0.5 μl, and 1.5 μl methanol were added.

The contents of each microtiter well were scanned at 1 nm increments using a SpectraMAX® Plus microplate spectrophotometer (Molecular Devices, Sunnyvale, Calif.) and were corrected for the background buffer absorbance (defined in row C) and Nanodisc absorbance (well A1).

LITERATURE CITED

Angrand, M. et al. (1997) *Eur. J. Biochem.* 250:168–76.
Atkinson, D. and Small, D. M. (1986) *Ann. Rev. Biophys. Chem.* 15: 403–456.
Bayburt, T. H. et al. (1998) *J. Struct. Biol.* 123: 37–44.
Bayburt, T. H. et al. (2000) *Langmuir* 16: 5993–5997.
Bayburt, T. H. et al. (2002) *Nano Letters* 2:853–856.
Boguski, M. S. et al. (1986) *J. of Lipid Research* 27: 1011–1034.
Borhani, D. W. et al. (1997) *Proc. Natl. Acad. Sci USA* 94: 12291–12296.
Brouillette, C. G. et al. (1984) *Biochemistry* 23: 359–367.
Brouillette, C. et al. (2001) *Biochim. Biophys. Acta* 1531: 4–46.
Carlson, J. W. et al. (2000) *Langmuir* 16: 3927–3931.
Carlson, J. W. et al. (1997) *Biophys. J.* 73: 1184–1189.
Chen et al. (1956) *Anal. Chem.* 28:1756–1758.
Chen, J. S. et al. (2002) *Insect Molecular Biology* 11:175–186.
Dalton, M. B. and Swaney, J. B. (1993) *J. Biol. Chem.* 268: 19274–19283.
Dencher, N. A. and Heyn, M. P. (1982) *Methods Enz.* 88:, 5–10.
Drake et al. (1989) *Am. J. Pathol.* 134: 1087–1097.
Durbin, D. M. and Jonas, A. (1999) *J. Lipid Research* 40: 2293–2302.
Estabrook, R. W., and J. Werringloer. (1978) *Meth. Enzymol.* 52:212–20.
Fidge, N. H. (1999) *J. Lipid Research* 40: 187–201.
Fielding, P. E. and Fielding, C. J. (1991) *Biochemistry of Lipids, Lipoproteins, and Membranes*. D. E. Vance and J. Vance. Amsterdam, Elsevier Press: 427–459.
Fiske and Subbarow (1925) *J. Biol. Chem.* 66:374–389.
Folch-Pi, J. et al. (1957) *J. Biol. Chem.* 226:497–509.
Forte, T. M. et al. (1971) *Biochim. Biophys. Acta* 248: 381–386.
Frank, P. G. et al. (1997) *Biochemistry* 36: 1798–1806.
Friis, E. P. et al. (1999) *Proc. Nati Acad. Sci. USA* 96: 1379–84.
Glomset, J. A. (1968) *J. Lipid Research* 9: 155–167.
Higuchi, R. et al. (1988) *Nucl. Acids Res.* 16: 7351.
Holvoet, P. et al. (1995) *Biochemistry* 34: 13334–13342.
Imaoka, S. et al. (1992) *Biochemistry* 31:6063–9.
Jonas, A. (1986) *Methods Enzymol.* 128: 553–582.
Jonas, A. (1991) *Biochim. Biophys. Acta* 1084: 205–220.
Jonas, A. et al. (1989) *J. Biol. Chem.* 264: 4818–4824.
Kirilovsky, J. et al. (1985) *Febs Letters* 183:75–80.
Koppaka, V. et al. (1999) *J. Biol. Chem.* 274: 14541–14544.
Ma, R. et al. (1994) *Arch. Biochem. Biophys.* 310:332–40.
Marheineke, K. er al. (1998) *Febs Letters* 441:49–52.
Miller, J. P. et al. (1996) *Biochemistry* 35: 1466–1474.
Mukhopadhyay, R. et al. (2000) *J. Inorg. Biochem.* 78: 251–254.
Nemerson, Y. and Repke, D. (1985) *Thromb. Res.* 40:350–358.
Omura, T., and R. Sato. (1964) *J. Biol. Chem.* 239:2370–8.
Phillips, J. C. et al. (1997) *Biophysics Journal* 73: 2337–2346.
Rezaie et al. (1992) *Protein Expression and Purification* 3: 453–460.
Robinson, C. R. and Sauer, R. T. (1998) *Proc. Natl Acad. Sci. USA* 95(11):5929–34].
Rogers, D. P. et al. (1998) *Biochemistry* 37: 945–955.

Rogers, D. P. et al. (1998) *Biochemistry* 37: 11714–11725.
Savelli, G. et al. (2000) *Curr. Opin. Colloid & Interface Science* 5:111–117.
Segrest, J. P. et al. (1999) *J. Biol. Chem.* 274: 31755–31758.
Tocanne, J.-F. et al. (1994) *Chemistry and Physics of Lipids* 73: 139–158.
Wald, J. H. et al. (1990) *J. Biol. Chem.* 265: 20044–20050.
Wald, J. H. et al. (1990) *J. Biol. Chem.* 265: 20037–20043.
Wang, M. et al. (1997) *Proc. Natl. Acad. Sci. USA* 94: 8411–8416.
Wlodawer, A. et al. (1979) *FEBS Lett.* 104: 231–2 Segr35.

---

What is claimed is:

1. A method for incorporating at least one hydrophobic or partially hydrophobic protein associated with a membrane or membrane fragment into a nanoscale particle which is stable and soluble in aqueous solution, said method comprising the steps of:
   (a) providing a solubilized membrane or membrane fragment preparation comprising at least one hydrophobic or partially hydrophobic protein of interest and a solubilizing agent in an aqueous solution;
   (b) contacting a membrane scaffold protein with the solubilized membrane or membrane fragment preparation of step (a); and
   (c) removing the solubilizing agent,
   whereby said at least one hydrophobic or partially hydrophobic protein and said membrane scaffold protein self-assemble into nanoscale particles in an aqueous solution.

2. The method of claim 1, wherein said at least one hydrophobic or partially hydrophobic protein is a tethered membrane protein, an embedded membrane protein or an integral membrane protein.

3. The method of claim 2, wherein the protein is a cytochrome P450.

4. The method of claim 2, wherein the protein is a cytochrome P450 reductase.

5. The method of claim 3, wherein the protein further includes cytochrome P450 reductase.

6. The method of claim 2, wherein said membrane protein is tissue factor.

7. The method of claim 2, wherein said membrane protein is a receptor protein.

8. The method of claim 7, wherein said receptor protein is a G-protein coupled receptor.

9. The method of claim 8, wherein said G-protein coupled receptor is a 5-hydroxytryptamine receptor.

10. The method of claim 1, wherein said membrane scaffold protein comprises an amino acid sequence selected from the group consisting of amino acids 13 to 212 of SEQ ID NO:6, SEQ ID NO:9, amino acids 12 to 414 of SEQ ID NO:17, amino acids 13 to 422 of SEQ ID NO:19, amino acids 13 to 168 of SEQ ID NO:23, amino acids 13 to 169 of SEQ ID NO:29, amino acids 13 to 201 of SEQ ID NO:43, amino acids 13 to 201 of SEQ ID NO:44, amino acids 13 to 392 of SEQ ID NO:45, amino acids 13 to 234 of SEQ ID NO:73, amino acids 13 to 256 of SEQ ID NO:74, amino acids 13 to 278 of SEQ ID NO:75, amino acids 24 to 223 of SEQ ID NO:76, SEQ ID NO:77, amino acids 24 to 212 of SEQ ID NO:78, SEQ ID NO:79, amino acids 24 to 201 of SEQ ID NO:80, amino acids 13 to 168 of SEQ ID NO:81, amino acids 13 to 168 of SEQ ID NO:82, amino acids 13 to 190 of SEQ ID NO:83, amino acids 13 to 201 of SEQ ID NO:84, amino acids 13 to 190 of SEQ ID NO:85, and amino acids 24 to 281 of SEQ ID NO:86.

11. The method of claim 1, wherein said solubilizing agent is a detergent.

12. The method of claim 1, wherein the solubilizing agent is cholate.

13. The method of claim 1, wherein the solubilizing agent is removed by dialysis or by adsorption.

14. The method of claim 1, wherein the molar ratio of MSP:solubilizing agent:membrane lipid is from 1:25:50 to 1:500:1000.

15. The method of claim 14, wherein the molar ratio of MSP:solubilizing agent:membrane lipid is 1:75:150.

16. The method of claim 10, wherein said membrane scaffold protein comprises an amino acid sequence selected from the group consisting of SEQ ID NO:6, SEQ ID NO:9, SEQ ID NO:17, SEQ ID NO:19, SEQ ID NO:23, SEQ ID NO:29, SEQ ID NO:43, SEQ ID NO:44, SEQ ID NO:45, SEQ ID NO:73, SEQ ID NO:74, SEQ ID NO:75, SEQ ID NO:76, SEQ ID NO:77, SEQ ID NO:78, SEQ ID NO:79, SEQ ID NO:80 SEQ ID NO:81, SEQ ID NO:82, SEQ ID NO:83, SEQ ID NO:84, SEQ ID NO:85, and SEQ ID NO:86.

17. The method of claim 1, wherein at least one phospholipid is added prior to step (c).

* * * * *